(12) United States Patent
Bot et al.

(10) Patent No.: US 6,630,169 B1
(45) Date of Patent: Oct. 7, 2003

(54) PARTICULATE DELIVERY SYSTEMS AND METHODS OF USE

(75) Inventors: Adrian I. Bot, San Diego, CA (US); Thomas E. Tarara, San Diego, CA (US); Jeffry G. Weers, San Diego, CA (US); Alexev Kabalnov, Corvalis, OR (US); Ernest G. Schutt, San Diego, CA (US); Luis A. Dellamary, San Marcos, CA (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 09/720,536

(22) PCT Filed: Mar. 31, 1999

(86) PCT No.: PCT/US99/06855
§ 371 (c)(1),
(2), (4) Date: Feb. 28, 2001

(87) PCT Pub. No.: WO00/00215
PCT Pub. Date: Jan. 6, 2000

(51) Int. Cl.⁷ ............................ A61K 9/14; A61K 9/16; A61K 9/127; A61E 2/00
(52) U.S. Cl. ................. 424/489; 424/426; 424/434; 424/450; 424/490
(58) Field of Search ............................. 424/426, 434, 424/489, 490, 450, 484

(56) References Cited

U.S. PATENT DOCUMENTS

| 5,043,158 A | 8/1991 | Sleytr et al. |
| 5,308,620 A | 5/1994 | Yen |
| 5,616,311 A | 4/1997 | Yen |
| 5,807,552 A | 9/1998 | Stanton et al. |
| 5,855,913 A | 1/1999 | Hanes et al. |
| 5,985,309 A | * 11/1999 | Edwards et al. ............ 424/426 |
| 6,071,497 A | 6/2000 | Steiner et al. |

FOREIGN PATENT DOCUMENTS

| EP | 0 274 431 B1 | 7/1988 |
| EP | 0 372 777 B1 | 6/1990 |
| EP | 0 611 567 A1 | 8/1994 |
| WO | wo 88/01862 | * 3/1988 |
| WO | 88/01862 | 3/1988 |
| WO | 99/16419 | 4/1999 |
| WO | 99/16420 | 4/1999 |
| WO | 99/16421 | 4/1999 |
| WO | wo 99/16421 | * 4/1999 |
| WO | 99/16422 | 4/1999 |
| WO | wo 9916422 | * 4/1999 |

OTHER PUBLICATIONS

International Search Report, PCT/US02/13145, dated Aug. 20, 2002.

* cited by examiner

Primary Examiner—Thurman K. Page
Assistant Examiner—S. Tran
(74) Attorney, Agent, or Firm—Felissa H. Cagan; Susan T. Evans; Guy V. Tucker

(57) ABSTRACT

Compositions and methods are provided for the administration of particulates comprising at least one bioactive agent which, in selected embodiments, may comprise and immunoactive agent. In this respect, the invention provides for both topical and systemic delivery of the bioactive agent using, for example, the respiratory, gastrointestinal or urogenital tracts. The particulates may be in the form of dry powders or combined with a non-aqueous suspension medium to provide stabilized dispersions. In preferred embodiments, the disclosed compositions will be used in conjunction with inhalation devices such as metered dose inhalers, dry powder inhalers, atomizers or nebulizers for targeted delivery of the agent to mucosal surfaces.

52 Claims, 15 Drawing Sheets

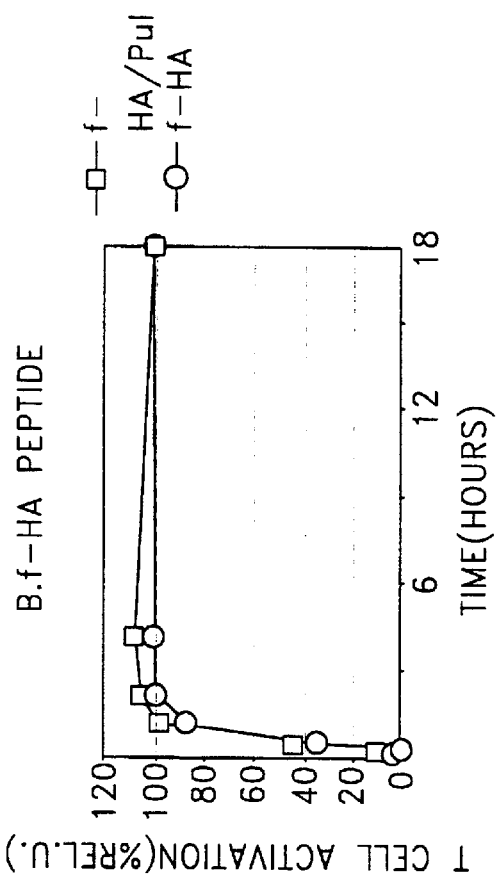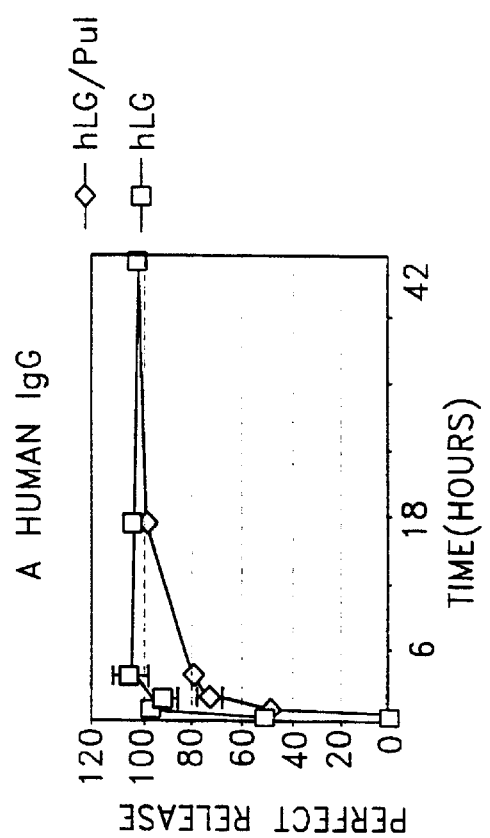
FIG.5A
FIG.5B

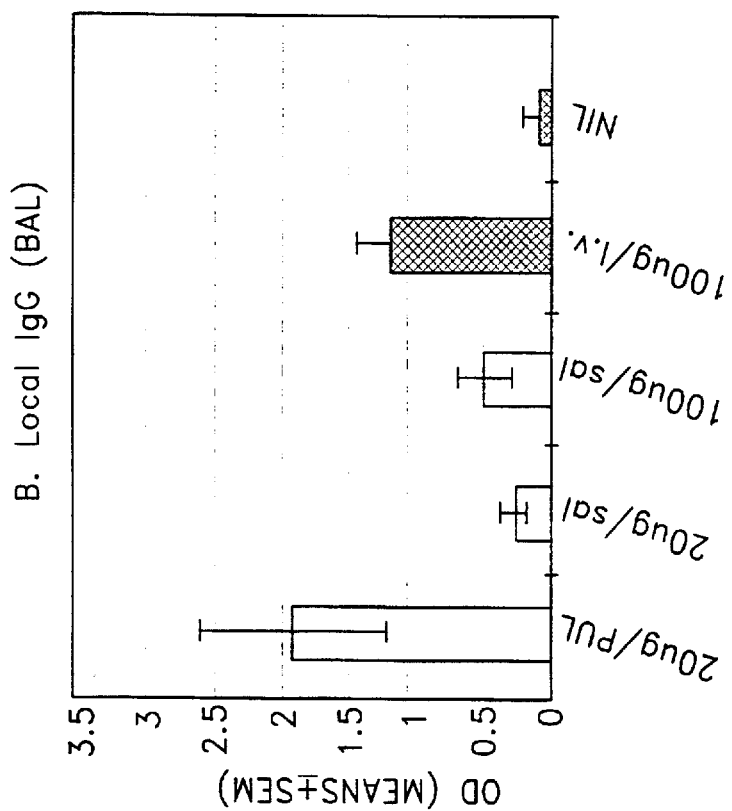
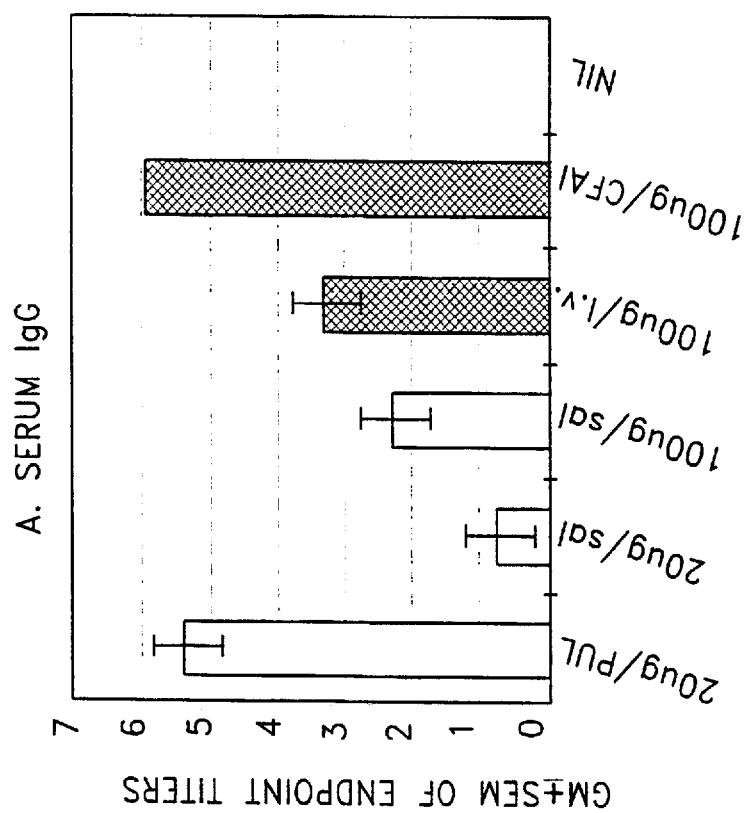
FIG. 7A
FIG. 7B

PARTICULATE DELIVERY SYSTEMS AND METHODS OF USE

This application is a 371 of PCT/US 99/06855 filed Mar. 31, 1999.

FIELD OF THE INVENTION

The present invention generally relates to compositions and methods for the administration of particulates comprising at least one bioactive agent which, in selected embodiments, may comprise an immunoactive agent. In this respect, the invention provides for both topical and systemic delivery of the bioactive agent using, for example, the respiratory, gastrointestinal or urogenital tracts. In particularly preferred embodiments, the disclosed compositions will be used in conjunction with inhalation devices such as metered dose inhalers, dry powder inhalers, atomizers or nebulizers for targeted delivery to mucosal surfaces.

BACKGROUND OF THE INVENTION

Vertebrates possess the ability to mount an immune response as a defense against pathogens from the environment as well as against aberrant cells, such as tumor cells, which develop internally. This can take the form of innate or passive immunity, which is mediated by neutrophils and cells of the monocyte/macrophage lineage, or the form of acquired or active immunity mediated by lymphocytes against a specific antigenic sequence. Active immune responses can themselves be further subdivided into two arms, the humoral response which entails the production of specific antibodies which serve to neutralize antigens exposed to the systemic circulation and aid in their uptake by professional phagocytic cells, and the cellular arm which is required for recognition of infected or aberrant cells within the body.

In both cases the specific response is triggered by the intracellular processing of antigen. When the antigen is processed through the cytoplasmic route, the resultant peptides are bound to nascent MHC class I molecules which facilitates appropriate presentation to effector T-cells. MHC class I presentation favors recognition by cytotoxic T lymphocytes. In contrast, intracellular processing via the endocytic route results in presentation on MHC class II molecules which favors T helper responses involved in stimulation of the humoral arm. The goal of vaccination is to prime both responses and generate memory T cells, such that the immune system is primed to react to a pathogenic infection. Such a response is promoted by the coadministration of signals that promote costimulatory molecule expression, so called "adjuvants." Engagement of both the humoral and cellular immune responses leads to broad based immunity and is the preferred goal for intracellular pathogens. The absence of appropriate costimulatory molecule expression can lead to a state of T cell unresponsiveness.

In this regard, modulation of an immune response can take one of two directions; either to elicit an immune response directed against a foreign pathogenic agent or antigen thereof, or to suppress an inappropriate reaction mounted against a self-epitope that leads to chronic inflammation. Such chronic reactions against self-epitopes are associated with various autoimmune diseases such as diabetes, typically type I, multiple sclerosis, rheumatoid arthritis or lupus erythrematosis. In either case, the active agent frequently takes the form of a relatively complex peptide, protein, RNA or DNA-based entity or other macromolecular structure rather than small chemical entities typical of classical pharmaceutical agents. These complex bioactive agents generally exhibit poor bioavailability when administered orally, and therefore have traditionally been administered by invasive parenteral injection. Recently however, it has been suggested that relatively large biomolecules may be delivered via mucosal routes, e.g. by inhalation. Delivery of these agents into systemic circulation through inhalation is particularly attractive since administration via the respiratory mucosa bypasses the digestive enzymes of the GI tract. Furthermore, it offers the potential for increased bioavailability for peptides and proteins because of the large surface area available for exchange with systemic circulation. While the molecular weight cut-off for oral bioavailability is generally regarded to be in the range of 500 Daltons, peptide hormones or analogues of larger molecular weight (e.g., 1.8 kD desmopressin, 5.8 kD insulin, 9.5 kD parathyroid hormone), have been shown to be absorbed across the nasal or pulmonary mucosa intact into the systemic circulation.

Besides allowing for the effective delivery of protein, peptide, viral and DNA formulations without degradation, targeted delivery to the mucosal surface itself may offer a benefit if it elicits a local immune response within the MALT (mucosa-associated lymphoid tissue) lymphoid system. Mucosal vaccination is of particular interest for vaccines designed against pathogens whose port of entry is typically at one of the mucosal surfaces interfacing the body with the external environment. The MALT lymphoid system resides within the lamina propria of the mucosa. When foreign antigen is presented to local dendritic cells, there is a local amplification and maturation of B-cell precursors, which produce IgA and IgM antibodies in addition to the IgG antibodies typically induced by systemic delivery of antigen. The former are secreted through specialized transport receptors by a process known as transcytosis across the mucosal surface into the lumen. There, they provide a first line of defense against invading pathogens at the mucosal surface. Recent evidence indicates that, in addition to binding pathogenic antigens, the resultant formation of immune complexes may in and of itself inhibit viral transmission occurring via the transcytotic route. By priming this first line immune response to antigens derived from pathogens, mucosal immunization should greatly enhance the efficiency with which the organism first intercepts an invading pathogen.

Several previous attempts have been made to exploit this uptake mechanism and provide for the effective delivery of peptides or proteins. For example, U.S. Pat. No. 5,756,104 describes the use of liposome formulations for intranasal vaccine formulations. These formulations appear to comprise aqueous carriers having liposomes and free antigenic material dispersed therein. While the compositions were found to elicit an immune response, they appear to be extremely labile and susceptible to degradation over time. In a practical sense this is a substantial drawback.

Attempts to overcome such limitations and further increase delivery efficiency have resulted in the development of dry powders for the administration of relatively large biomolecules. Unfortunately, conventional powdered preparations (i.e. micronized) often fail to provide accurate, reproducible dosing over extended periods. In part, this is because the powders tend to aggregate due to hydrophobic or electrostatic interactions between the fine particles. Such cohesion may be partially overcome through the use of larger carrier particles (i.e. lactose) to inhibit aggregation. However, these larger particles and associated drug often fail to reach the targeted cells resulting in uneven delivery profiles. Further, crude mixtures comprising carrier molecules provide little, if any, protection for the incorporated biomolecule. Accordingly, as with the aqueous compositions described above, such preparations are subject to degradation and loss of activity over time.

More recently, improved formulation methods have been undertaken in order to overcome the limitations associated with conventional prior art powders and aqueous preparations. In this regard, U.S. patent applications Ser. Nos. 09/218,209 and 09/219,736, incorporated herein by reference, describe methods and processes for generating preparations comprising bioactive agents in microparticulate form. The resultant powders, which preferably exhibit a hollow, porous morphology, are suitable for use in inhalation devices such as dry powder inhalers (DPIs) or, when suspended in a nonaqueous liquid (i.e. a hydrofluoroalkane or fluorocarbon), metered dose inhalers (MDIs) and nebulizers. Moreover, the mild conditions used during the formulation process support retention of biological activity making the preparations particularly compatible for use with proteins and peptides as well as more complex macromolecular structures such as viruses. Additionally, since the resultant powders have very low residual water content, which can be further maintained by formulation in short-chain fluorocarbons or fluorochemicals such as propellants or the longer chain fluorochemicals such as perfluorooctyl bromide (PFOB), these formulations provide a stable means for storage of labile bioactive agents.

Besides enhanced stability, the preferred hollow, porous morphology of the microparticulates provides aerodynamic characteristics that are particularly compatible with inhalation therapies. Further, the particulate characteristics allows for the formation of exceptionally stable dispersions and makes them especially compatible with hydrofluoroalkane propellants such as HFA-134a as well as other fluorocarbon liquid vehicles like PFOB. Thus, whether used in a dry form or as a nonaqueous dispersion, the microparticulates provide for good dose reproducibility, excellent plume characteristics (a measure of the uniformity of a propellant or dry powder spray) and a high percentage of the dose delivered as the respirable fraction (as opposed to deposition in the device or throat). These properties suggest that the disclosed microparticles offer substantial theoretical advantages as far as delivery deep into the lung. Such deep deposition is preferred where delivery into the systemic circulation is desired since uptake of large macromolecules like proteins and peptides is optimal at the level of the alveoli.

While the use of such microparticulate preparations is a substantial improvement over conventional prior art delivery methods, there still remains a need to provide for the targeted delivery of bioactive, immunomodulating or immunoactive agents that results in an enhanced physiological response.

Accordingly, it is an object of the present invention to provide compositions, systems and methods that provide for the generation of an enhanced immune response.

It is another object to provide for the effective delivery of immunoactive agents, including vaccines and immunomodulating agents, to the mucosal surfaces of a patient in need thereof.

It is yet a further object of the present invention to provide vaccine or other bioactive formulations that do not require refrigeration or freezing to maintain activity.

It is still a further object of the present invention to provide for the establishment of passive and active immunity via inhalation therapies.

It is yet another object of the present invention to provide for stable preparations of immunoactive agents that may be used to confer immunity or down regulate the immune system of a patient in need thereof.

SUMMARY OF THE INVENTION

These and other objects are provided for by the invention disclosed and claimed herein. To that end, the methods and associated compositions of the present invention allow, in a broad aspect, for the improved delivery of bioactive agents to selected target sites in a powdered or particulate form. More particularly, it has been surprisingly been found that the disclosed methods and compositions may be used to enhance or increase the activity of an incorporated bioactive agent, which preferably comprises an immunoactive agent, following administration. In this regard, the vaccines of the instant invention appear to exhibit an "adjuvant effect" that may provoke an enhanced immune response an order of magnitude or more greater than that provoked by a comparable prior art vaccine formulation. Besides this unexpected improvement in potency, relatively gentle formulation techniques may be combined with particulate morphology and composition to protect and enhance the activity of any incorporated agents. This allows for the formation of relatively efficacious preparations that retain their biological activity without the need for refrigeration or freezing. Further, unlike prior art powders or dispersions for drug delivery, the present invention preferably employs novel techniques to reduce attractive forces between the particles, resulting in improved flowability and dispersibility. When these powders are incorporated in a nonaqueous suspension medium (e.g. a liquid fluorochemical) these same characteristics provide for reduced flocculation, sedimentation or creaming that may further reduce the rate of agent degradation. Finally, administration of the disclosed particulates or dispersions to selected target sites such as mucosal surfaces may further serve to optimize or enhance bioactivity. As such, the dispersions or powders of the present invention may be used to effectively deliver bioactive agents in conjunction with metered dose inhalers, dry powder inhalers, atomizers, aerosolizers, nasal pumps, spray bottles, nebulizers or liquid dose instillation (LDI) techniques.

A particularly beneficial feature of the disclosed particulate formulation technology is that a wide range of bioactive structures can be incorporated in the stabilized dispersions or powders irrespective of their hydrophobicity or hydrophilicity. In preferred embodiments, the bioactive powders will be produced using relatively mild spray drying methodology. Due to such compatible particulate formulation techniques, larger, more labile biomolecules such as peptides, proteins or genetic material may readily be incorporated in the disclosed compositions without adverse effects or undue loss of activity. These same formulation techniques and resulting particulates further provide for the incorporation and delivery of relatively high doses (ca. 10 mg) of bioactive agents using conventional administration techniques and systems. Thus, whether administered in the form of a dry powder or stabilized dispersion, the novel particulate fabrication techniques and enhanced response afforded by the disclosed preparations lead to the effective delivery of bioactive agents to targeted sites such as the mucosa.

In connection with the present invention, the term "bioactive agent" refers to any active peptide or protein, such as a hormone, cytokine or chemokine or an immunoactive agent. That is, while the disclosed compositions and methods are compatible with almost any bioactive agent, they have been discovered to be surprisingly effective for the delivery or administration of immunoactive agents designed to modulate immune responses such as, for example, eliciting an immune response to a foreign antigen or pathogen or down regulating an active immune reaction. Accordingly, as used herein, the terms "immunoactive agents," or "immunologically active agents," will comprise any molecule that may be used to elicit a physiological or immune response or modulate pre-existing responses in a subject. Such immunoactive agents or biologics may comprise peptides, polypeptides, proteins, carbohydrates, genetic material including DNA, RNA and antisense constructs, as well as microbes including viruses, phages and bacteria.

In addition, molecules that may function as cofactors, potentiators or penetration enhancers can be readily co-formulated in the particulates described herein. Those skilled in the art will appreciate that any compound which acts to improve the uptake, presentation or bioavailability may function as a potentiator or penetration enhancer in accordance with the teachings herein. For instance, compounds that can alter or increase the membrane permeability of a cell may function as potentiators or penetration enhancers. Exemplary potentiators or penetration enhancers may include chelating agents (e.g. EDTA, citric acid), detergents or surfactants (e.g. 9-lauryl ether), fatty acids (e.g. oleic acid) and bile salts (e.g. sodium glycocholate). Particularly preferred penetration enhancers comprise relatively short chain phospholipids having chain lengths of less than about 10 carbons. As with the bioactive agents, and as will be discussed in more detail below, the selected potentiators or penetration enhancers may be incorporated in, or associated with, particulates in varying concentrations.

With regard to the particulates, microparticulates or perforated microstructures of the present invention, those skilled in the art will appreciate that they may be formed of any biocompatible material providing the desired physical characteristics or morphology. In this respect, perforated microstructures will preferably comprise pores, voids, defects or other interstitial spaces that act to reduce attractive forces by minimizing surface interactions and decreasing shear forces. This morphology acts to reduce aggregation and improve dispersability. Yet, given these constraints, it will be appreciated that any biocompatible material or configuration may be used to form the microstructure matrix. As to the selected materials, it is desirable that the microstructure incorporates at least one surfactant which, in preferred embodiments, will act as a penetration enhancer. Preferably, this surfactant will comprise a phospholipid or other surfactant or amphiphile approved for pharmaceutical use. Similarly, it is preferred that the microstructures incorporate at least one bioactive agent or biologic. As to the configuration, selected embodiments of the invention comprise spray dried, hollow microspheres having a relatively thin porous wall defining a large internal void, although, other void containing or perforated structures are contemplated as well.

It has unexpectedly been found that the use of hollow and/or porous perforated microstructures may substantially reduce attractive molecular forces, such as van der Waals forces, which dominate prior art powdered preparations and dispersions. In this respect, the powdered compositions typically have relatively low bulk densities that contribute to the flowability of the preparations while providing the desired characteristics for inhalation therapies. More particularly, the use of relatively low density perforated (or porous) microstructures or microparticulates significantly reduces attractive forces between the particles thereby lowering the shear forces required to achieve flowability of the resulting powders. The relatively low density of the perforated microstructures also provides for superior aerodynamic performance when used in inhalation therapy. In dispersions, the physical characteristics of these powders provide for the formation of stable preparations. Moreover, by selecting dispersion components in accordance with the teachings herein, interparticle attractive forces may further be reduced to provide formulations or preparations having enhanced stability.

While preferred embodiments of the invention comprise perforated microstructures or porous particulates, relatively nonporous or solid particulates may also be used to prepare powders or dispersions that are compatible with the teachings herein. That is, powders or dispersions comprising suspensions of relatively nonporous or solid particulates are also contemplated as being within the scope of the present invention. In this respect, such relatively nonporous particulates may comprise micronized particles, milled particles or nanocrystals. Accordingly, as used herein the term "particulate" shall be interpreted broadly and held to comprise particles of any porosity and or density, including both perforated microstructures and relatively nonporous particles.

As previously alluded to, the disclosed powders may be dispersed in an appropriate nonaqueous suspension medium to provide stabilized dispersions comprising a selected bioactive agent. Such dispersions are particularly useful in metered dose inhalers, atomizers nasal pumps, spray bottles and nebulizers. Other embodiments of the invention comprise stabilized dispersions that may be administered directly to the lung or nasal cavity using direct instillation techniques. In any case, particularly preferred suspension mediums comprise fluorochemicals (i.e. perfluorocarbons or fluorocarbons) that are liquid at room temperature or fluorinated propellants (i.e. hydrofluoroalkanes or chlorofluorocarbons). Because of their beneficial wetting characteristics, some fluorochemicals may be able to provide for the dispersion of particles deeper into the lung or other mucosal surface, thereby improving systemic delivery. Moreover, such suspension media tend to be anhydrous thereby retarding hydrolytic degradation of the incorporated bioactive agents. Finally, fluorochemicals are generally bacteriostatic thus decreasing the potential for microbial growth and associated proteolytic decay in compatible preparations.

With regard to the delivery of the disclosed powders or stabilized dispersions, another aspect of the present invention is directed to inhalation systems for the administration of one or more bioactive agents or biologics to a patient. As alluded to above, exemplary inhalation devices compatible with the present invention may comprise an atomizer, a nasal pump, a sprayer or spray bottle, a dry powder inhaler, a metered dose inhaler or a nebulizer. In preferred embodiments, these inhalation systems will deliver the bioactive agent to the desired physiological site (e.g. a mucosal surface) as an aerosol. For the purposes of the instant application the term "aerosolized" shall be held to mean a gaseous suspension of fine solid or liquid particles unless otherwise dictated by contextual restraints. That is, an aerosol or aerosolized medicament may be generated, for example, by a dry powder inhaler, a metered dose inhaler, an atomizer, a spray bottle or a nebulizer. Of course, as explained in more detail below, the compositions of the present invention may also be delivered directly (e.g. by conventional injection or needleless injection) or using such techniques as liquid dose instillation. In especially preferred embodiments the compositions of the present invention are contacted with a mucosal surface (e.g. via inhalation) to elicit both mucosal and systemic immunity.

While the powders or stabilized dispersions of the present invention are particularly suitable for administration of bioactive agents to mucosal surfaces, it will be appreciated that they may also be used for the localized or systemic administration of compounds to any location of the body. Accordingly, it should be emphasized that, in preferred embodiments, the formulations may be administered using a number of different routes including, but not limited to, the gastrointestinal tract, the respiratory tract, topically, intramuscularly, parenterally, intradermally, transdermally, intraperitoneally, nasally, vaginally, rectally, aurally, buccally, orally or ocularly. In this respect those skilled in the art will appreciate that the selected route of administration will largely be determined by the choice of bioactive agent and the desired response of the subject.

Other objects, features and advantages of the present invention will be apparent to those skilled in the art from a consideration of the following detailed description of preferred exemplary embodiments thereof.

BRIEF DESCRIPTION OF THE DRAWINGS

FIGS. 5A and 5B graphically illustrate release kinetics for IgG formulated microparticulates and HA peptide formulated microparticulates respectively;

FIGS. 7A and 7B show, respectively, systemic and localized antibody responses to IgG administered intratracheally as formulated microparticulates in accordance with the present invention;

DETAILED DESCRIPTION OF PREFERRED EMBODIMENTS

A. Introduction

Figure 1:
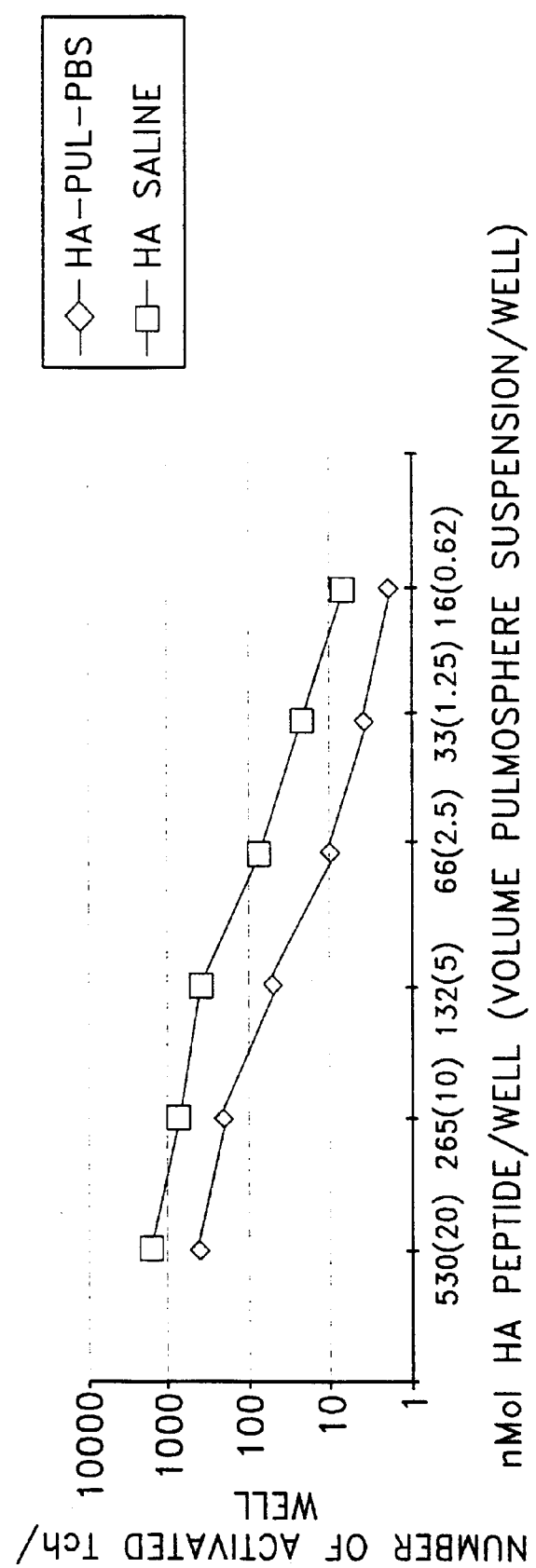
FIG. 1 is a graphical representation of levels of functional HA peptide (residues 110–120 of the hemagglutinin of the influenza virus) following formulation in microstructures according to the present invention.

While the present invention may be embodied in many different forms, disclosed herein are specific illustrative embodiments thereof that exemplify the principles of the invention. It should be emphasized that the present invention is not limited to the specific embodiments as illustrated.

As discussed above, the present invention provides methods, systems and compositions comprising powders or microparticulates that may advantageously be used for the delivery of bioactive agents. Preferably the bioactive agent will comprise active peptides or proteins or an immunoactive agent. In the context of the present invention, immunoactive agents may comprise any molecule that may be used to elicit an immune response or modulate pre-existing responses such as vaccines, immunoglobulins or autoantigens. Those skilled in the art will appreciate that the disclosed powders may advantageously be used to deliver bioactive agents in a dry state (e.g. with a DPI or gas driven powder injector) or in the form of a stabilized dispersion (e.g. with an atomizer, spray bottle, MDI, LDI, needleless injector, syringe, nasal pump or nebulizer). In particularly preferred embodiments, the powders or microparticulates will comprise perforated microstructures which, as disclosed herein, comprise a structural matrix that exhibits, defines or comprises voids, pores, defects, hollows, spaces, interstitial spaces, apertures, perforations or holes. These perforated microstructure powders have aerodynamic characteristics that make them particularly useful for inhalation therapy and exhibit morphologies that allow for the formation of stabilized dispersions in propellants or nonaqueous delivery vehicles. More generally, the relatively mild conditions employed during the formation of the disclosed bioactive powders and advantages associated with compatible delivery methods allow for the efficient administration of comparatively fragile biologic agents.

While not wishing to be bound by any particular theory, it is believed that the relatively gentle methods used to form, store and administer the disclosed compositions provide for the effective retention of biological activity in generally unstable agents. In this respect, preferred formulations do not require refrigeration to maintain their activity. Moreover, selection of appropriate compounds for use in the disclosed powders and delivery to selected physiological sites (e.g. mucosal surfaces) may promote the uptake of the incorporated agent or agents as well as enhancing the activity thereof. In addition, the compositions and/or delivery techniques of the present invention appear to generate an unexpected "adjuvant effect" that may provide for an enhanced immune response or bioactivity following administration of the selected agent. More specifically, as will be discussed below and seen in the Examples, the present invention may be used to elicit an immune response comparable to that achieved by administering an antigen in complete Freund's adjuvant (i.e. an order of magnitude or more higher than conventional pharmaceutical formulations). Accordingly, the present invention provides for the effective delivery of active peptides, proteins, genetic material, or pathogenic particles (either live or inactivated) to induce active localized or systemic immunization or to achieve passive immunization, immune modulation, hormonal regulation or gene therapy.

B. Bioactive Agents

In a broad aspect, the powdered or microparticulate compositions of the present invention, including dispersions incorporating such powders, will preferably comprise at least one bioactive agent. As used herein, the term "bioactive agent" shall be held to comprise any active peptide or protein or any immunoactive agent. With respect to the latter, particularly preferred embodiments of the present invention will comprise an immunoactive agent designed capable of modulating an immune response. In accordance with the teachings herein, modulation of a subject's immune response shall comprise eliciting a response against a potential pathogenic infection or foreign antigen, stimulating an existing immune response, inducing localized or systemic passive immunity or suppressing an autoimmune response or allergenic response. For the purposes of the instant application the terms "bioactive agent" or immunoactive agent" shall be broadly construed to comprise any molecule or organism, or analog, homologue or derivative thereof, that provides a desired physiological or immune response in a subject. It will be appreciated that the term "bioactive agent" shall be held inclusive of the term "immunoactive agent" and its equivalents unless otherwise dictated by contextual restraints. Exemplary bioactive agents that may be used in conjunction with the invention comprise peptides, polypeptides, proteins, fusion or chimeric proteins, immunoglobulins, genetic material including DNA, RNA, recombinant and antisense constructs, microbes including viruses, phages, bacterial carbohydrates and bacteria as well as smaller molecules that may function as potentiators, cofactors or penetration enhancers. The bioactive compositions according to the present invention find use as vaccines, immunomodulators, effectors or replicons for gene therapy applications.

It will be appreciated that the powders or microparticulate compositions of the present invention may exclusively comprise one or more bioactive agent(s) (i.e. up to 100% w/w). However, in selected embodiments the perforated microstructures may incorporate much less bioactive agent depending on the activity thereof. Accordingly, for highly active materials the particulates, microparticulates or perforated microstructures may incorporate as little as 0.001% by weight although a concentration of greater than about 0.1% w/w is preferred. Other embodiments of the invention may comprise greater than about 5%, 10%, 15%, 20%, 25%, 30% or even 40% w/w active or bioactive agent or biologic. Still more preferably the disclosed powders may comprise greater than about 50%, 60%, 70%, 75%, 80% or even 90% w/w of a bioactive agent. The precise amount of bioactive agent incorporated in the powders or perforated microstructures of the present invention is dependent upon the agent of choice, the required dose, method of administration and the form of the agent actually used. Those skilled in the art will appreciate that such determinations may be made by using well-known pharmacological techniques in combination with the teachings of the present invention.

With regard to pharmaceutical preparations, any bioactive agent that may be formulated in the disclosed powders or perforated microstructures for the purpose of eliciting a physiological response, including an immune response, is expressly held to be within the scope of the present invention. In accordance with the teachings herein the selected bioactive agent(s) may be associated with, or incorporated in, the powders or perforated microstructures in any form that provides the desired efficacy and is compatible with the chosen production techniques. As used herein, the terms "associate" or "associating" mean that the particulate, microparticulate, structural matrix or perforated microstructure may comprise, incorporate, adsorb, absorb, be coated with or be formed by the bioactive agent. Where appropriate, the agent may be used in the form of salts (e.g. alkali metal or amine salts or as acid addition salts) or as esters or as solvates (hydrates). In this regard the form of the bioactive agent may be selected to optimize the activity and/or stability of the compound and/or to minimize the solubility of the agent in the suspension medium and/or to minimize particle aggregation.

At least to some extent, the advantages provided by the instant invention reside in the unique formulation, storage and delivery aspects afforded by the disclosed powders and dispersions. In this respect, and as will be discussed in more detail below, the conditions under which the disclosed powders or perforated microstructures may be formed are relatively mild. That is, particulates comprising bioactive agents may be formed according to the present invention without subjecting the active compound or agent to extreme physical or chemical conditions. This is of extreme importance with regard to relatively large macromolecules or agents such as proteins, genetic material or attenuated viruses that may easily be degraded or inactivated. Moreover, selected embodiments of the present invention further serve to maintain the biological activity of incorporated agents by forming relatively stable dispersions comprising nonaqueous suspension media. These dispersions of active powder in suspension medium (preferably a liquid fluorochemical or fluorochemical propellant) tend to be both bacteriostatic and anhydrous, thereby inhibiting hydrolysis or proteolytic decay of the incorporated agent. It will be appreciated that such compositions have been found to maintain comparatively high levels of activity over prolonged storage periods. Finally, it has been found surprisingly that both the composition of the disclosed powders and delivery techniques thereof can be adjusted to potentiate or enhance the activity of the associated bioactive agent. Taken together, these advantages of the present invention provide for the efficient delivery and efficacy of highly active agents to the selected physiological site.

As indicated above the compositions, methods and systems of the instant invention are useful for the delivery of bioactive agents such as peptides, polypeptides, bacterial carbohydrates, viruses and genetic material. In this respect, the disclosed invention is particularly useful for the administration of vaccines for active immunization (e.g. mucosal and systemic vaccination), immunoglobulins for passive immunization, immunomodulators for the treatment of autoimmune diseases, active peptides or proteins, and effectors and expression vectors for gene therapy or vaccination. As will be explained in more detail below, powders comprising the selected agent may be formed through a variety of different means. Preferably, the powders or microparticulates will be in the form of perforated microstructures and will comprise additional components to enhance the stability and/or efficacy of the incorporated bioactive agent. Optionally, the powders may be formulated in a suspension medium to provide stabilized dispersions.

Particularly preferred classes of bioactive agents will be discussed in more detail immediately below.

B(i). Antigens and Vaccines (for Active Immunization)

In accordance with the teachings herein, particularly preferred bioactive agents will comprise vaccines. As discussed throughout the instant specification and accompanying examples, compatible vaccines may comprise inactivated or killed microbes (e.g. viruses), live attenuated microbes, phages, subunit vaccines such as proteins, peptides or carbohydrates (e.g. bacterial carbohydrates), genetic material including replicons, viral vectors, and plasmids and recombinant molecules such as fusion proteins or chimeric antibodies. Regardless of which type of agent or biologic is selected, the resulting powdered compositions may be used to immunize a subject against one or more target antigens. Further, the adjuvant effect or enhanced immunity associated with the disclosed invention provides for particularly effective immunization.

As defined herein a "target antigen" refers to an antigen, typically a portion of a protein or a peptide, toward which it is desirable to induce an immune response. Such an antigen may be comprised in a pathogen, such as a viral, bacterial, protozoan, fungal, yeast, or parasitic antigen, or may be comprised in a cell, such as a cancer cell. Tumor antigens and viral antigens are especially preferred target antigens. In the case of genetic vaccines, one or more target antigens will be expressed by the host following transfection or transformation of autologous cells with the administered genetic material. Conversely, in protein or peptide based vaccines, including those comprising chimeric or fusion proteins or killed or attenuated microbes, the target antigen or antigens will be presented directly to the immune system. In either case, presentation of the target antigens using the powders or dispersions of the instant invention will provoke the desired immune response. Interestingly, it has been found that when live viruses, or combinations of live and killed viruses have been used as vaccines in accordance with the teachings herein, a particularly vigorous immune response is generated by the subject.

Those skilled in the art will appreciate that, in general, an effective anti-viral immune response comprises both a cell-mediated response, typically involving Th1/CTL cell response and a B cell-mediated humoral response. Whereas a purified protein or killed microbe usually elicit B, Th2 without CTL responses, certain formulations of subunit or killed vaccines, as well as live vaccines can elicit B, Th1 associated with CTL responses. Preferably, the vaccine compositions of the present invention will induce a broad range of immune responses upon administration, including B, Th1 and CTL responses. However, infection with live virus during vaccination can lead to unacceptable side effects. Therefore the goal of a successful vaccination strategy is to engage both the cellular and humoral branches of immunity without incurring undue adverse effects. As will be disclosed below, the compositions of the present invention may be used to induce both types of response upon administration.

In this respect, compatible vaccines may include any molecule, organism or compound that results in the generation of B cell response, a T cell response or a combination thereof to the target antigen. As such, the agent actually presented to the host immune system (whether directly or following transformation of host cells) may be an analog, homologue or derivative of the naturally occurring target antigen or molecule comprising the target antigen. Moreover, the immunization may be local or systemic in nature depending on the type of target antigen presented and the form of delivery. For example, in particularly preferred embodiments the immunogenic response will be largely mucosal in nature (e.g. within the mucosa-associated lymphoid tissue [MALT] lymphoid system). As previously discussed, when foreign antigen is presented by local dendritic cells, there is a local amplification and maturation of T-cells and B-cells, which produce IgA and IgM antibodies in addition to the IgG antibodies typically induced by systemic delivery of antigen. Such localized immunization, particularly in the nasal passages and sinuses, has been found to be particularly effective in preventing infection by airborne pathogens such as influenza virus and respiratory syncytial virus. More generally, the vaccine compositions of the present invention may comprise one or more target antigens from a number of pathogens. For example, but not by way of limitation, the target antigen may be comprised in an influenza virus, a cytomegalovirus, a herpes virus (including HSV-I and HSV-II), a vaccinia virus, a hepatitis virus (including but not limited to hepatitis A, B, C, or D), a varicella virus, a rotavirus, a papilloma virus, a measles virus, an Epstein Barr virus, a coxsackie virus, a polio virus, an enterovirus, an adenovirus, a retrovirus (including, but not limited to, HIV1 or HIV2), a respiratory syncytial virus, a rubella virus, a Streptococcus bacterium (such as *Streptococcus pneumoniae*), a Staphylococcus bacterium (such as *Staphylococcus aureus*), a Hemophilus bacterium (such as *Hemophilus unfluenzae*), a Listeria bacterium (such as *Listeria monocytogenes*), a Kiebsiella bacterium, a Gram-negative bacillus bacterium, an Escherichia bacterium (such as *Escherichia coli*), a Salmonella bacterium (such as *Salmonella typhimurium*), a Vibrio bacterium (such as *Vibrio cholerae*), a Yersinia bacterium (such as *Yersinia pestis* or *Yersinia enterocoliticus*), an Enterococcus bacterium, a Neisseria bacterium (such as *Neisseria meningitidis*), a Corynebacterium bacterium (such as *Corynebacterium diphtheriae*), a Clostridium bacterium (such as *Clostridium tetani*), a Mycoplasma (such as *Mycoplasma tuberculosis*), a Candida yeast, an Aspergillus fungus, a Mucor fungus, a toxoplasma, an amoeba, a malarial parasite, a trypanosomal parasite, a leishmanial parasite, a helminth, etc. Specific nonlimiting examples of such target antigens include hemagglutinin, nucleoprotein, M protein, F protein, HBS protein, gp120 protein of HIV, nef protein of HIV, and listeriolysine.

Regardless of what type of antigen is selected to be the target antigen it will comprise at least one relevant epitope. The term "relevant epitope", as used herein, refers to an epitope comprised in the target antigen which is accessible to the immune system. For example, a relevant epitope may be processed after penetration of a microbe into a cell or recognized by antibodies on the surface of the microbe or microbial proteins. Preferably, an immune response directed toward the epitope confers a beneficial effect; for example, where the target antigen is a viral protein, an immune response toward a relevant epitope of the target antigen at least partially neutralizes the infectivity or pathogenicity of the virus. Those skilled in the art will appreciate that the relevant epitopes may be B-cell or T-cell epitopes.

The term "B cell epitope", as used herein, refers to a peptide, including a peptide sequence contained within a larger protein, which can elicit antibody production by B cells.

For example, and not by way of limitation, the hypervariable region 3 loop ("V3 loop") of the envelope protein of human immunodeficiency virus ("HIV") type 1 is known to be a B cell epitope. Other examples of known B cell epitopes which may be used according to the invention, include, but are not limited to, epitopes associated with influenza virus strains, such as site B of influenza HA 1 hemagglutinin, which has been shown to be an immunodominant B cell epitope (Li et al., 1992, J. Virol. 66:399–404); an epitope of F protein of measles virus (residues 404–414, Parlidos et al., 1992, Eur. J. Immunol. 22:2675–2680); an epitope of hepatitis virus pre-S1 region, from residues 132–145 (Leclerc, 1991, J. Immunol. 147:3545–3552); and an epitope of foot and mouth disease VP1 protein, (residues 141–160, Clarke et al., 1987, Nature 330381–384). Still further B cell epitopes which may be used are known or may be identified by methods known in the art, as set forth in Caton et al., 1982, Cell 31:417–427.

In additional embodiments of the invention, the peptides may comprise T cell epitopes. The term "T cell epitope", as used herein, refers to a peptide, including a peptide sequence within a larger protein, which when associated with MHC self antigens and recognized by a T cell, functionally activates the T cell. In this regard the present invention provides for the $T_h$ epitopes which, in the context of MHC class II self antigens, may be recognized by a helper T cell and thereby promote the facilitation of B cell antibody production via the $T_h$ cell.

For example, and not by way limitation, influenza A hemagglutinin (HA) protein of PR8 strain, bears, at amino acid residues 110–120, a $T_h$ epitope. Other examples of known T cell epitopes include, but are not limited to, two promiscuous epitopes of tetanus toxoid (Ho et al., 1990, Eur J. Immunol. 20:477–483); an epitope of cytochrome c, (residues 88–103); an epitope of Mycrobacteria heatshock protein, (residues 350–369, Vordermir et al., Eur. J. Immunol. 24:2061–2067); an epitope of hen egg white lysozyme, (residues 48–61, Neilsonet al., 1992, Proc. Natl. Acad. Sci. U.S.A. 89:7380–7383); an epitope of Streptococcus A M protein, (residues 308–319, Rossiter et al., 1994, Eur. J. Immunol. 24:1244–1247); and an epitope of Staphylococcus nuclease protein, (residues 81–100, de Magistris, 1992, Dell 68:1–20). Still further $T_h$ epitopes which may be used in conjunction with the instant invention are known or may be readily identified by methods known in the art.

As a further example, a relevant epitope may be a CTL epitope, which, in the context of MHC class I self antigens, may be recognized by a cytotoxic T cell and thereby promote CTL-mediated lysis of cells comprising the target antigen. Nonlimiting examples of such epitopes include epitopes of influenza virus nucleoproteins corresponding to amino acid residues 147–161 and 365–379, respectively (Taylor et al., 1989 Immunogenetics 26:267; Townsend et al., 1983, Nature 348:674); LSMV peptide, (amino acid residues 33–41; Zinkernagel et al., 1974, Nature 248:701–702); and ovalbumin peptide, corresponding to amino acid residues 257–264 (Cerbone et al., 1983, J. Exp. Med 163:603–612).

With regard to genetic vaccines, one or more target antigens will be expressed by the host following transfection or transformation of autologous cells with the administered genetic material. The expressed antigen(s) then elicit the desired immune response in the subject. Those skilled in the art will appreciate that genetic material may be associated with the powder in the form of naked molecules (e.g. DNA or RNA) or in a viral vector form. In either case, nucleic acids compatible with the invention will preferably encode one or more relevant epitopes, and may optionally further comprise elements that regulate the expression and/or stability and/or immunogenicity of the relevant epitope.

For example, elements that regulate the expression of the epitope encoded within the genetic construct include, but are not limited to, a promoter/enhancer element, a transcriptional initiation site, a polyadenylation site, a transcriptional termination site, a ribosome binding site, a translational start codon, a translational stop codon, a signal peptide, etc. Specific examples include, but are not limited to, a promoter and intron A sequence of the initial early gene of cytomegalovirus (CMV or SV40 virus ("SV40"); Montgomery et al., 1993, DNA and Cell Biology 12:777–783). Alternatively, more than one epitope may be expressed within the same open reading frame. Examples of genetic vaccines which may be used according to the invention, and methods for their production, are set forth in International Application Publication No. WO 94/21797, by Merck & Co. and Vical, Inc., International Application Publication No. WO 97/21687, by Mt. Sinai, U.S. Pat. Nos. 5,589,466 and 5,580,859 and in International Application Publication No. WO 90/11092, by Vical, Inc., the contents of which are incorporated by reference in their entireties.

To provide enhanced stability and/or immunogenicity of the relevant epitope, it may be desirable to present the epitope in the context of a larger peptide or protein. For example, the relevant epitope may be expressed in the variable region of a chimeric antibody or as a portion of a fusion protein. In other preferred embodiments, it may be advantageous to administer a full-length protein (e.g. a viral coat protein) comprising one or more relevant epitopes. Alternatively, it may be desirable to administer powders or perforated microstructures comprising combinations or cocktails of immunogenic peptides or proteins. In this regard it will be appreciated that the relevant epitopes may be derived from the same or different pathogens. With respect to the latter, opportunistic pathogens may be targeted along with the primary disease causing agent. In addition to the broad target range, the disclosed compositions may comprise various epitope combinations. For example, the compositions of the present invention may comprise nucleic acids or peptides or proteins comprising mixtures of B cell epitopes, mixtures of T cell epitopes, or combinations of B and T cell epitopes.

More particularly, the administration of compositions that comprise or express more than one relevant epitope may exhibit an unexpected synergistic effect. It will be appreciated that such combination vaccines may prove to be much more efficient at conferring the desired immunity with respect to the selected pathogen(s) than compositions comprising a single nucleic acid species encoding a single relevant epitope. Those skilled in the art will further appreciate that such synergism could allow for an effective immunoprophylactic or immunotherapeutic response to be generated with lower dosing and less frequent administration than single-epitope vaccines. Moreover, the use of such multiepitope vaccine compositions may provide more comprehensive protection as the induced multi-site immunity would tend to be more resistant to natural phenotypic variation within a species or rapid mutation of a target antigen by the selected pathogen. Of course, effective immunity may also be imparted by vaccines encoding a single B or T cell epitope and such compositions are clearly contemplated as being within the scope of the present invention.

In addition to the antigens themselves, the current invention permits manipulation of the excipient components of the particle shell itself to enhance or modify the immunogenicity of the formulated antigen. For example, efficient antigen capture by dendritic cells has been shown to be facilitated when the antigen uptake is facilitated by the mannose receptor and hence improves targeting to the lysosomal compartment (Salusto et al, J. Expt Med.

182:389–400, 1995). Therefore, incorporation of a low percent of mannans, or other polysaccharides that bind to receptors on cells, into the particulates would be predicted to enhance the immunogenicity. Furthermore, as will be discussed in more detail below, the use of cofactor or cytokines to promote APC responses might also serve to enhance or suppress an immune response as required. The current invention permits for co-formulation of antigen with cofactors that might augment stimulation local immune responses within the mucosa or other targeted sites of delivery (e.g. transdermal) directed to local dendritic cell or other APC. By facilitating APC activation and enhancing antigen uptake and presentation within a local environment, such combination formulations provided by the current invention could lead to increased efficiency of the resultant immune response.

More generally, the methods and compositions of the present invention provide for an enhanced immune response when used to immunize or vaccinate a subject. This "adjuvant effect" provided by the disclosed particulates may be used to elicit an immune response comparable to that elicited by an antigen administered with an adjuvant (i.e. alum or complete Freund's adjuvant). Unlike the present invention, those skilled in the art will appreciate that such traditional adjuvants are typically associated with undesirable side effects and, in many cases, are not available for use in humans. Conversely, the present invention can afford an enhanced immune response (i.e. an immune response greater than that generated by a comparable antigen presented using art recognized techniques such as CTL levels for antibody titers), without the administration of potentially toxic adjuvants. While not wishing to be bound by any particular theory, it is believed that the observed enhancement is, at least in part, a result of the particulate configuration or morphology, antigen release profile and possible antigen aggregation within the particulate. In any event, the effect allows the generation of a clinically useful immune response with lower levels of antigen and/or fewer inoculations.

By this adjuvant effect, the immune response provided by the compositions and methods of the instant invention is enhanced relative to prior art inoculation techniques. In particular, the immune response elicited by the compositions of present invention will generally be greater than the immune response provoked by intravenous or intraperitoneal administration of the same antigen solubilized or suspended in an aqueous carrier. Of course, the magnitude of the elicited immune response may be measured using any one of a variety of techniques well known to those in the art including compatible methods set forth in the Examples below. Using such comparisons, the preparations of the present invention will preferably provoke an immune response that is 25%, 50%, 75% or 100% greater than that provoked by administration of the same antigen using the prior art methods discussed above. More preferably, the present invention will provoke a response that is 2, 3, 4 or 5 times greater than the baseline response obtained using the antigen in an aqueous carrier. In even more preferred embodiments, the disclosed preparations and methods will elicit an immune response that is 6, 7, 8, 9 or even 10 times greater than the baseline response. Still other embodiments may produce responses that are 20, 30, 40, 50 times or even two orders of magnitude greater than baseline. Those skilled in the art will appreciate that these novel, and heretofore unexpected properties, of the disclosed particulates make them extremely effective in generating the desired immune response in a subject.

Besides the aforementioned adjuvant effect, other mechanisms may also contribute to an enhanced immune response in accordance with the teachings herein. For example, it has surprisingly been found that combinations of live and killed virus provoke a much stronger response than that provided by the killed virus alone. More particularly, in preferred embodiments the powders may be formulated using a live attenuated virus which is, to some extent, killed or inactivated during the particulate fabrication. As will be demonstrated in conjunction with the Examples below, this mixture of live and killed virus appears to elicit a surprisingly strong, or enhanced, immune response. Moreover, in keeping with the teachings herein, the selected virus or virus mixture may comprise a naturally occurring inactivated or attenuated virus or may be engineered to express one or more foreign antigens. An alternative method of formulating live virus provided for by the present invention involves the formulation of viral receptors within the particle matrix followed by binding the selected virus to the particles after fabrication (i.e. after spray drying). There are a wide variety of cellular viral receptors that have now been well defined, for example, the prolactin receptor which can function as a retrovirus receptor, CCR5, the cellular receptor for HIV, the Polio virus receptor, the IgG Fc region which binds HSV1 and receptors that bind influenza virus.

Regardless of the antigen selected or the form of the antigen (virus, peptide, genetic material, etc.), those skilled in the art will further appreciate that effective immunization of a subject may include more than one inoculation. As used herein, the terms "immunize" or "immunization" or related terms refer herein to conferring the ability to mount a substantial immune response (consisting of antibodies or cellular immunity such as effector CTL) against a target antigen or epitope. These terms do not require that completely protective immunity be created, but rather that a protective immune response be produced which is substantially greater than baseline. For example, a mammalian may be considered to be immunized against a target antigen if the cellular and/or humoral immune response to the target antigen is enhanced following the application of methods of the invention. Assays demonstrating the enhancement of both B cell or T cell responses are well known and could easily be performed by those skilled in the art. Preferably, immunization results in significant resistance to the disease caused or triggered by pathogens expressing target antigens.

Similarly, the term "inoculating", as used herein, refers to administering or introducing a composition comprising at least one vaccine comprising a relevant epitope, or capable of generating or expressing a relevant epitope, according to the instant disclosure. While an effective immune response may be induced with a single inoculation, effective immunization of a subject may comprise multiple inoculations or a subsequent booster or boosters. As such, the methods of the present invention may comprise one, two, three, four or even five inoculations in order to achieve the desired immunoprophylactic effect. Moreover, as previously alluded to the administered vaccine will preferably contact and/or be absorbed by a mucosal surface. In particularly preferred embodiments, the mucosal surface will be associated with oral or nasal passages or cavities or a pulmonary air passage. Those skilled in the art will further appreciate that the vaccine compositions of the present invention (i.e. powders or dispersions) may be used to inoculate neonates (0–6 mo), infants (6 mo–2 yr), children (2 yr–13 yr) or adults (13 yr+).

B(ii). Immunoglobulins (Passive Immunotherapy)

While the methods and compositions of the present invention provide effective means for inducing localized and systemic active immunity, they may also be used for the induction of localized or systemic passive immunity. In particular, the disclosed powders and microparticulates may be used to administer immunoglobulins, or fragments or portions thereof, to provide rapid prophylaxis or therapy with regard to infection or disease. The administered immunoglobulins, which may be monoclonal or polyclonal, will recognize at least one antigen on the target pathogen. Preferably, the recognized antigen or antigens will comprise one or more relatively conserved epitopes. For the purposes of the present invention, the administered compositions may comprise neutralizing, therapeutic or prophylactic antibodies or combinations thereof. In particularly preferred embodiments, the administered compositions will comprise one or more species of monoclonal antibodies or immunoreactive fragments.

Following administration, the active immunoglobulin or immunoglobulins can either function at the site of delivery or be taken up into the systemic circulation. Antibodies retained at the site of administration could rapidly bind to any target infectious agent (e.g. an airborne virus) coming in contact with the treated site (i.e. a mucosal surface) and prevent subsequent infection or clear the microbes. Alternatively, the relatively high levels of circulating antibodies provided by preferred embodiments of the instant invention will allow rapid clearance of the target pathogen from the bloodstream thereby preventing, or at least ameliorating, symptoms associated with infection. Of course it will be appreciated that, unlike active immunization which can last for the lifetime of the subject, passive immunization is relatively transitory, lasting as long as the delivered immunoglobulin dose remains in the circulation.

As alluded to above any immunoglobulin, or immunoreactive fragment thereof, that recognizes an antigen or antigens on a target pathogen, may be used to confer the desired immunity on a subject. The ability to provide both monoclonal and polyclonal antibodies to particular pathogens and/or antigens and/or epitopes is well known in the art. With respect to the form of antibody actually administered, it will be appreciated that both native and engineered antibodies are compatible with the teachings herein, as are different classes of antibodies including IgA, IgD, IgE, IgG and IgM. Similarly, any immunoreactive fragment or domain of an immunoglobulin, including $F(ab')_2$, Fab, or Fv can be used to provide the desired protection. Regarding engineered antibodies, humanized constructs (i.e. chimeric antibodies) are particularly preferred. While such immunoglobulins typically contain the antigen binding complementarity determining regions (CDRs) of murine antibodies, the remainder of the molecule is comprises human antibody sequences which are not recognized as foreign. See, for example, Jones et al., Nature, 321:522–525 (1986) which is incorporated herein by reference. As human polyclonal IgG is not typically recognized as foreign by the subject, these antibodies do not tend to produce undesirable side effects if infrequently administered and are not rapidly eliminated by the body.

Passive immunity is particularly effective in preventing or reducing the chances of infection by readily transmitted pathogens, particularly those that are air or water borne. As such, powders and dispersions of the present invention comprising the appropriate immunoglobulins are especially effective against respiratory viruses and pathogens such as influenza or respiratory syncytial virus. For example, a stabilized dispersion comprising immunoglobulin laden perforated microstructures in a liquid fluorocarbon medium could be administered to the nasal passages via an atomizer or spray bottle. The composition, which could easily be administered as needed, would provide both localized and systemic passive immunity with respect to a target pathogen such as a cold virus (Orthomyxovirus, Paramyxovirus, Rhinovirus). Similarly, readily administered compositions could be provided in accordance with the present invention to provide protection against water borne agents such as *Vibrio cholerae*. Passive immunity as disclosed herein could also be used to provide at least some protection with respect to various organisms including, but not limited to, Rabies virus, Hepatitis (A, B, C) viruses, HIV and *Clostridium tetanii*. Other infectious agents for which passive immunity may be imparted by the disclosed compositions may easily be identified by those skilled in the art.

B(iii). Tumor Antigens

In alternative embodiments, the target antigen may be a tumor antigen. Those skilled in the art will appreciate that tumor antigens are often peptide fragments derived from cell proteins that either are restricted to the type of tissue from which the tumor is derived or are mutated during the course of malignant transformation. Other tumor antigens are often aberrantly expressed by the tumor cell and/or represent "neo" antigens resulting from errors in transcription, RNA processing due to mutations that are idiosyncratic to the tumor cells. Alternatively, changes in post-translational modifications of a normal protein (e.g. glycosylation) may aid in revealing hitherto hidden (cryptic) epitopes not normally recognized by the immune system (e.g., as is the case with the mucin, MUC1). B cell epitopes associated with tumor antigens are expressed at the surface of tumor cells and are recognized by specific antibodies. In contrast, T cell epitopes are of two types: CTL epitopes that are MHC class I-restricted peptides derived from tumor associated antigens and Th epitopes that are MHC class II-restricted peptides derived from tumor antigens. Whereas Th epitopes are mostly presented by antigen presenting cells (APC) to $CD4^+$ T cells, CTL epitopes are presented by APC as well as tumor cells and are recognized by tumor-specific $CD8^+$ T cells. Exemplary tumor antigens include, but are not limited to, carcinoembryonic antigen ("CEA"), melanoma associated antigens, alpha fetoprotein, papilloma virus antigens, Epstein Barr antigens, MUC 1, p53, etc. Several other tumor antigens are reportedly recognized by autologous cytotoxic T lymphocytes as set forth in Boon, T., et al. J. Exp. Med., 183:725–729, 1996; Disis, M. L., et al. Curr. Opin. Immunol. 8:637–642, 1996; Robbins, P. F., et al. Curr. Opin. Immunol. 8:628–636, 1996, Salgaller et al., J. Surg. Oncol. 68:122–138, 1998, each of which is incorporated herein their entirety.

B(iv). Immune Modulation

Autoimmune diseases are mediated by autoreactive T and B cells as well as other immune cell subtypes that may exert regulatory or effector roles. It is thought that T cells recognizing organ-specific self epitopes are a key element in the pathogenesis of autoimmune diseases such as diabetes type 1, multiple sclerosis (MS) or rheumatoid arthritis (RA). CD4+ and in certain cases, CD8+T cells recognizing antigens presented in certain locations of the body may infiltrate the tissue and trigger destruction of various cell types and persisting inflammation. Whereas Cf4+ Th1 cells that produce IL-2, IFN-, TNF- and LT- are considered pathogenic, CD4+ Th2 cells that produce IL-4, IL10, IL-5, IL-13 and IL-9 are considered non-pathogenic relative to autoimmunity and in certain circumstances may suppress disease. Furthermore, Th3 cells induced by mucosal exposure to antigens, to secrete TGF- and IL-10, are thought to be crucial mediators of mucosal-induced tolerance.

As a strategy to prevent or suppress the autoimmune diseases, autoreactive T cells provide a good therapeutic target. There are several means of inactivating the pathogenic autoreactive T cells (general designation of "tolerance", which is not necessarily restricted to "deletion"), responsible for the autoimmune disease: (1) to directly turn-off or anergize the pathogenic cells by providing long-time exposure to high levels of antigen; (2) to anergize or switch the function of pathogenic T cells by exposing them to antigens in context of non-professional APC or certain modulating factors; and (3) to induce antigen-specific Th suppressor cells of Th2/Th3 phenotype that migrate to the site of disease and inhibits the function of pathogenic T cells.

Surprisingly, it has been found that tolerance may be induced in accordance with the present invention through the use of inhalation therapies. The advantage of the respiratory tract as the target site for immune tolerance induction is two-fold: first, it is a non-invasive route that allows local and systemic delivery of complex antigens; and secondly, mucosal immunity is likely to comprise Th2/Th3 suppressor cells to the administered antigens. Such antigens may be whole self antigens (recombinant or purified), antigen fragments (obtained by molecular biology or biochemical techniques well known in the art) or peptides limited to epitopes. In other embodiments they may be incorporated as virus components, phages, chimeric antibodies, fusion proteins, replicons, bacteria or delivered via nucleic acid-based or viral vectors. They may be incorporated in self molecules like immunoglobulins or any natural or synthetic ligand for receptors on body cells. They may be administered as isolated, individual components or in mixtures. Examples for diabetes type I include but are not limited to such peptides and antigens as: GAD65 (glutamic acid decarboxylase 65—Baekkeskov et al., Nature 1990, 347:151), insulin (Palmer et al., Science 1983, 222:1337), ICA512/IA-2 (islet cell antigen 512; Rabin et al., J. Immunol. 1994, 152:3183). In the case of MS, such proteins and peptides are: MBP (myelin basic protein, Steinman et al., 1995, Mol. Med. Today, 1:79; Warren et al., 1995, Proc. Natl. Acad. Sci. USA, 92:11061). PLP, transaldolase, 2',3' cyclic nucleotide 3' phosphodiesterases (CNP), MOG and MAG (Steinman L., 1995, Nature, 375:379). Besides autoimmune diseases, it will be appreciated that the compositions and methods of the present invention may also be used to down regulate immune responses provoked by allergens.

B(v). Active Peptides and Proteins

Certain peptides and proteins are known to have to ability to modulate, up-regulate or down-regulate immune responses to foreign or self antigens. Such peptides or proteins may act by engaging endogenous receptors leading to activation or inhibition of certain processes, or by interfering with the ligand-receptor binding of endogenous elements. Examples of such proteins or peptides are cytokines that exert immune modulatory function leading to suppression of autoimmunity: interferon-, IL4, IL-10, IL-13, IL-9, native or in the form of fragments attached, incorporated or complexed with other molecules. Other cytokines may act as immune activators, leading to increased immunity against microbes or tumor cells: IL-12, IL-2, interferon-, interferon-, TNF-, TNF-, lymphotoxins, and GM-CSF. For example, co-administration of GC-MSF, IFN-α, IL-2, IL-12 or TNF-α has been demonstrated to enhance an immune response and antigen presentation. However, systemic delivery of such agents in many cases has led to unacceptable side effects, leading to a concerted effort directed at targeted delivery of these pluripotent factors. The current invention advantageously permits for co-formulation of a selected antigen or antigens with cofactors that might augment stimulation local immune responses within the mucosa or other targeted sites of delivery (e.g. transdermal or intradermal) directed to local dendritic cell or other APC presentation. By facilitating APC activation and enhancing antigen uptake and presentation within a local environment such combination formulations of the current invention could provide for increased efficiency of the resultant immune response.

Other active proteins or peptides that may be used in accordance with the present invention comprise chemokines in native form or as fragments, constructs or complexes with other molecules which may increase, modulate or inhibit the recruitment of lymphocytes. For example, whereas eotaxin-1, eotaxin-2, TARC, MIP-3b, SLC are thought to mediate the recruitment of Th2 cells, MIG, IP-10, MIP-1, MIP-1 and RANTES are thought to mediate the recruitment of Th1 cells (Sallusto et al., 1998, J. Exp. Med., 187:875; Ward et al., 1998, Immunity, 9:1). Similarly, cytokine or chemokine receptors in native form, or as fragments, recombinant constructs or complexes with other molecules may inhibit the recruitment or activation of certain lymphocytes. Examples of cytokine and chemokine receptors that are likely to inhibit ongoing Th1 responses comprise the IL-12 receptor, IFN-receptor, IL-2 receptor, TNF-receptor, CXCR3 or CCR5. Examples of cytokine and chemokine receptors that are likely to inhibit ongoing Th2 responses are the IL4 receptor, IL-13 receptor, IL-9 receptor, IL-10 receptor, CCR3, CCR4 or CCR7. Of course, it will be appreciated that compatible compounds are not limited to cytokines, chemokines or their receptors, but may include other ligands or receptors (in native form, fragments, constructs or complexes with other molecules) like integrins and homing receptors. In preferred embodiments all these categories of compounds may be formulated and administered either locally or systemically via the respiratory tract in order to enhance, suppress, or modulate an immune response.

It will further be appreciated that the perforated microstructures according to the invention may, if desired, contain a combination of two or more active ingredients. The agents may be provided in combination in a single species of perforated microstructure or individually in separate species of perforated microstructures. For example, two or more active or bioactive agents may be incorporated in a single feed stock preparation and spray dried to provide a single microstructure species comprising a plurality of bioactive agents. Conversely, the individual agents could be added to separate stocks and spray dried separately to provide a plurality of microstructure species with different compositions. These individual species could be added to the suspension medium or dry powder dispensing compartment in any desired proportion and placed in the aerosol delivery system as described below.

Based on the foregoing, it will be appreciated by those skilled in the art that a wide variety of bioactive agents may be incorporated in the disclosed powders. Accordingly, the list of preferred bioactive agents above is exemplary only and not intended to be limiting. It will also be appreciated by those skilled in the art that the proper amount of bioactive agent and the timing of the dosages may be determined for the formulations in accordance with already existing information and without undue experimentation.

C. Powder Composition

As may be seen from the discussion above, the present invention may be used to effectively deliver a wide variety of bioactive agents. While the particulates may be formed exclusively by the bioactive agent, they will preferably comprise one or more additional materials which, in selected embodiments, may comprise absorption enhancers, potentiators, excipients or structural components. More generally, the particulates (i.e. the structural matrix) may be formed of or comprise any material which possesses physical and chemical characteristics that are compatible with any incorporated active agents. While a wide variety of materials may be used to form the powders, in particularly preferred pharmaceutical embodiments the particulate is associated with, or comprises, a surfactant such as phospholipid or fluorinated surfactant. Although not required, the incorporation of a compatible surfactant can improve powder flowability, increase aerosol efficiency, improve dispersion stability, and facilitate preparation of a suspension. Moreover, selected surfactants may also function as absorption enhancers thereby increasing uptake and improving bioactivity of the selected agent. Of course it will be appreciated that the powders of the present invention may also be formed using nothing more than traditional non-surfactant excipients and one or more incorporated bioactive agents.

As indicated, the disclosed powders may optionally be associated with, or comprise, one or more surfactants. In accordance with the teachings herein, these compounds may serve to stabilize any incorporated bioactive agent, assist in stabilizing particulates suspended in a nonaqueous media or potentiate the uptake of an agent at the target site. Besides those surfactants associated with the disclosed particulates, miscible surfactants may optionally be combined in the case where the microparticles are formulated in a suspension medium liquid phase. It will be appreciated by those skilled in the art that the use of surfactants, while not necessary to practice the instant invention, may further increase dispersion stability, powder flowability, simplify formulation procedures or increase efficiency of delivery. Of course combinations of surfactants, including the use of one or more in the liquid phase and one or more associated with the perforated microstructures are contemplated as being within the scope of the invention. By "associated with or comprise" it is meant that the particulate or perforated microstructure may incorporate, adsorb, absorb, be coated with or be formed by the surfactant.

In a broad sense, surfactants suitable for use in the present invention include any compound or composition that aids in the formation of perforated microparticles or provides enhanced suspension stability, improved powder dispersibility or decreased particle aggregation. The surfactant may comprise a single compound or any combination of compounds, such as in the case of co-surfactants. Particularly preferred surfactants are nonfluorinated and selected from the group consisting of saturated and unsaturated lipids, nonionic detergents, nonionic block copolymers, ionic surfactants and combinations thereof. In those embodiments comprising stabilized dispersions, such nonfluorinated surfactants will preferably be relatively insoluble in the suspension medium. It should be emphasized that, in addition to the aforementioned surfactants, suitable fluorinated surfactants are compatible with the teachings herein and may be used to provide the desired preparations.

Lipids, including phospholipids, from both natural and synthetic sources are particularly compatible with the present invention and may be used in varying concentrations to form the particulates or structural matrix. Generally compatible lipids comprise those that have a gel to liquid crystal phase transition greater than about 40° C. Preferably the incorporated lipids are relatively long chain (i.e. $C_{16}$–$C_{22}$) saturated lipids and more preferably comprise phospholipids. Exemplary phospholipids useful in the disclosed stabilized preparations comprise, dipalmitoylphosphatidylcholine, disteroylphosphatidylcholine, diarachidoylphosphatidylcholine dibehenoylphosphatidylcholine, short-chain phosphatidylcholines, long-chain saturated phosphatidylethanolamines, long-chain saturated phosphatidylserines, long-chain saturated phosphatidylglycerols, long-chain saturated phosphatidylinositols, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate.

Compatible nonionic detergents comprise: sorbitan esters including sorbitan trioleate (Span® 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.) which is incorporated herein in its entirety. Preferred block copolymers include diblock and triblock copolymers of polyoxyethylene and polyoxypropylene, including poloxamer 188 (Pluronic® F-68), poloxamer 407 (Pluronic® F-127), and poloxamer 338. Ionic surfactants such as sodium sulfosuccinate, and fatty acid soaps may also be utilized. In preferred embodiments the microstructures may comprise oleic acid or its alkali salt. Due to their excellent biocompatibility characteristics, phospholipids and combinations of phospholipids and poloxamers are particularly suitable for use in the pharmaceutical embodiments disclosed herein.

In addition to the aforementioned surfactants, cationic surfactants or lipids are preferred especially in the case of delivery or RNA or DNA. Examples of suitable cationic lipids include: DOTMA, N-[1-(2,3-dioleyloxy)propyl]-N,N,N-trimethylammonium chloride; DOTAP, 1,2-dioleyloxy-3-(trimethylammonio)propane; and DOTB, 1,2-dioleyl-3-(4'-trimethylammonio)butanoyl-sn-glycerol. Polycationic amino acids such as polylysine, and polyarginine are also contemplated.

Besides those surfactants enumerated above, it will further be appreciated that a wide range of surfactants may optionally be used in conjunction with the present invention. Moreover, the optimum surfactant or combination thereof for a given application can readily be determined by empirical studies that do not require undue experimentation. Finally, as discussed in more detail below, surfactants comprising the particulate or structural matrix may also be useful in the formation of precursor oil-in-water emulsions (i.e. spray drying feed stock) used during processing to form the perforated microstructures.

Unlike prior art formulations, it has surprisingly been found that the incorporation of relatively high levels of surfactants or biocompatible wall forming material (e.g., phospholipids) may be used to improve powder dispersibility, increase suspension stability and decrease powder aggregation of the disclosed applications. That is, on a weight to weight basis, the particulate or structural matrix of the perforated microstructures may comprise relatively high levels of surfactant. In this regard, the particulates will preferably comprise greater than about 1%, 5%, 10%, 15%, 18%, 20% w/w surfactant. More preferably, the microparticulates or microstructures will comprise greater than about 25%, 30%, 35%, 40%, 45%, or 50% w/w surfactant. Still other exemplary embodiments will comprise particulates wherein the surfactant or surfactants are present at greater than about 55%, 60%, 65%, 70%, 75%, 80%, 85%, 90% or even 95% w/w. In selected embodiments the powders will comprise essentially 100% w/w of a surfactant such as a phospholipid. Those skilled in the art will appreciate that, in such cases, the balance of the particulate or structural matrix (where applicable) will likely comprise a bioactive agent, excipients or other additives.

As will be discussed below, surfactants may be incorporated in any type of particulate. That is, while the aforementioned surfactant levels are preferably employed in perforated microstructures, they may be used to provide powders or stabilized dispersions comprising relatively nonporous, or substantially solid, particulates. While selected embodiments of the present invention will comprise perforated microstructures associated with high levels of surfactant, compatible powders may be formed using relatively low porosity particulates of equivalent surfactant concentrations. Preferably, such particulates will comprise relatively high levels of surfactant on the order of greater than about 5% w/w. In this respect, such embodiments are specifically contemplated as being within the scope of the present invention.

In other preferred embodiments of the invention, the particulates optionally comprise synthetic or natural polymers or combinations thereof. In this respect useful polymers comprise polylactides, polylactide-co-glycolides, cyclodextrins, polyacrylates, methylcellulose, carboxymethylcellulose, polyvinyl alcohols, polyanhydrides, polylactams, polyvinyl pyrrolidones, monosaccharides, disaccharides or polysaccharides (dextrans, starches, chitin, chitosan, etc.), hyaluronic acid, proteins, (albumin, collagen, gelatin, etc.). Examples of polymeric resins that might prove useful for the preparation of microparticles include: styrene-butadiene, styreneisoprene, styrene-acrylonitrile, ethylene-vinyl acetate, ethylene-acrylate, ethylene-acrylic acid, ethylene-methylacrylatate, ethylene-ethyl acrylate, vinyl-methyl methacrylate, acrylic acid-methyl methacrylate, and vinyl chloride-vinyl, acetate. Those skilled in the art will appreciate that, by selecting the appropriate polymers, the delivery efficiency of the particulates and/or the stability of the dispersions may be tailored to optimize the effectiveness of the active or bioactive agent.

Besides the aforementioned polymer materials and surfactants, various excipients may be incorporated in, or added to, the particulates to provide structure and, in preferred embodiments form perforated microstructures (i.e. microspheres such as latex particles). In this regard it will be appreciated that the rigidifying components can be removed using a post-production technique such as selective solvent extraction. Compatible excipients may include, but are not limited to, carbohydrates including monosaccharides, disaccharides and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins and maltodextrins. Amino acids are also suitable excipients with glycine preferred. Mixtures of carbohydrates and amino acids are further held to be within the scope of the present invention. The inclusion of both inorganic (e.g. sodium chloride, calcium chloride, etc.), organic salts (e.g. sodium citrate, sodium ascorbate, magnesium gluconate, sodium gluconate, tromethamine hydrochloride, etc.) and buffers is also contemplated. The inclusion of salts and organic solids such as ammonium carbonate, ammonium acetate, ammonium chloride or camphor are also contemplated.

Along with the compounds discussed above, it may be desirable to add other excipients to a microsphere formulation to improve particle rigidity, production yield, delivery efficiency and deposition, shelf-life and patient acceptance. Such optional excipients include, but are not limited to: coloring agents, taste masking agents, buffers, hygroscopic agents, antioxidants, and chemical stabilizers. Moreover, as discussed above, the particulates may comprise compounds that can potentiate, induce or modulate the uptake of the associated bioactive agent. Further, the particulates of the invention may comprise targeting molecules such as antibodies, cofactors, receptors, ligands and substrates that preferentially direct the particulates, or allow them to bind, to molecules associated with cells at the target site. For example, particulates could be formed comprising an antibody targeting a mucosal cell receptor and an immunoactive compound. Such targeting molecules would likely increase the concentration of bioactive particulates at the target mucosal site and further enhance any localized immune response. It will be appreciated that ligands directed to receptors preferentially expressed on the surface of mucosal or other target cells could also be used to increase the binding of particulates at the desired site.

Yet other preferred embodiments include perforated microstructures that may comprise, or may be coated with, charged species that prolong residence time at the point of contact or enhance penetration through mucosae. For example, anionic charges are known to favor mucoadhesion while cationic charges may be used to associate the formed microparticulate with negatively charged bioactive agents such as genetic material. The charges may be imparted through the association or incorporation of polyanionic or polycationic materials such as polyacrylic acids, polylysine, polylactic acid and chitosan.

D. Powder Morphology

Those skilled in the art will appreciate that powders or particulates of various compositions, configurations and morphologies may be used in accordance with the present invention as long as they provide desired stability and delivery characteristics. In this respect, it may be advantageous to use relatively dense, solid particulates or powders for some applications (e.g. for intradermal administration of a stabilized dispersion via a air gun or needleless injector) while in other embodiments (e.g. DPI administration) a relatively porous, aerodynamically light perforated microstructure may be preferred. Accordingly, while the present invention may be discussed below in terms of preferred embodiments, it must be emphasized that it is not limited to any particular particle composition, configuration or morphology. Rather, selection of particulate characteristics (charge, density, composition, etc.) is largely based on the form of administration, targeted delivery site and choice of bioactive agent.

While various particulate configurations, including micronized and milled particulates, may be used in accordance with the teachings herein, the present invention provides unique methods and compositions to reduce cohesive forces between dry particles, thereby minimizing particulate aggregation that can result in improved delivery efficiency. As such, selected disclosed preparations provide a highly flowable, dry powders that can be efficiently aerosolized, uniformly delivered and penetrate deeply in the lung or nasal passages. Moreover, selected powder configurations and morphologies have been found to provide relatively stable dispersions when combined with a nonaqueous suspension medium. In either case, the disclosed particulates may be fabricated so as to result in surprisingly low throat deposition upon administration.

As previously discussed, particularly preferred embodiments of the present invention incorporate powders or particulates in the form of porous or perforated microstructures comprising a structural matrix. It will be appreciated that, as used herein, the terms "structural matrix" or "microstructure matrix" are equivalent and shall be held to mean any solid material forming perforated microstructures which define a plurality of voids, apertures, hollows, defects, pores, holes, fissures, etc. that provide the desired characteristics. In selected embodiments, the perforated microstructures defined by the structural matrix comprise a spray dried hollow porous microsphere incorporating at least one surfactant. It will further be appreciated that, by altering the matrix components, the density of the structural matrix may be adjusted so as to further increase dispersion stability or delivery efficiency.

The absolute shape (as opposed to the morphology) of the particulates or perforated microstructures is generally not critical and any overall configuration that provides the desired characteristics is contemplated as being within the scope of the invention. Accordingly, preferred embodiments can comprise approximately microspherical shapes. However, collapsed, deformed or fractured particulates are also compatible. With this caveat, it will further be appreciated that, particularly preferred embodiments of the invention comprise spray dried hollow, porous microspheres. In any case the disclosed powders of perforated microstructures provide several advantages including, but not limited to, increases in suspension stability, improved dispersibility, superior sampling characteristics, elimination of carrier particles and enhanced aerodynamics.

To maximize dispersibility, dispersion stability and optimize distribution upon administration, the mean geometric particle size of the particulates or perforated microstructures is preferably about 0.5–50 $\mu$m, more preferably 1–30 $\mu$m. It will be appreciated that large particles (i.e. greater than 50 $\mu$m) may not be preferred in applications where a valve or small orifice is employed, since large particles tend to aggregate or separate from a suspension which could potentially clog the device. In especially preferred embodiments the mean geometric particle size (or diameter) of the perforated microstructures is less than 20 $\mu$m or less than 1 $\mu$m. More preferably the mean geometric diameter is less than about 7 $\mu$m or 5 $\mu$m, and even more preferably less than about 4 $\mu$m or even 2.5 $\mu$m. Other preferred embodiments will comprise preparations wherein the mean geometric diameter of the perforated microstructures is between about 1 $\mu$m and 5 $\mu$m. In especially preferred embodiments the perforated microstructures will comprise a powder of dry, hollow, porous microspherical shells of approximately 1 to 10 $\mu$m or 1 to 5 $\mu$m in diameter, with shell thicknesses of approximately 0.1 $\mu$m to approximately 0.5 $\mu$m. It is a particular advantage of the present invention that the particulate concentration of the dispersions and structural matrix components can be adjusted to optimize the delivery characteristics of the selected particle size.

As alluded to throughout the instant specification the porosity of the microstructures may play a significant part is establishing dispersibility (e.g. in DPIs) or dispersion stability (e.g. for MDIs, jet guns or nebulizers). In this respect, the mean porosity of the perforated microstructures may be determined through electron microscopy coupled with modern imaging techniques. More specifically, electron micrographs of representative samples of the perforated microstructures may be obtained and digitally analyzed to quantify the porosity of the preparation. Such methodology is well known in the art and may be accomplished without undue experimentation.

For the purposes of the present invention, the mean porosity (i.e. the percentage of the particle surface area that is open to the interior and/or a central void) of the particulates or perforated microstructures may range from approximately 0.5% to approximately 80%. In more preferred embodiments, the mean porosity will range from approximately 2% to approximately 40%. Based on selected production parameters, the mean porosity may be greater than approximately, 2%, 5%, 10%, 15%, 20%, 25% or 30% of the microstructure surface area. In other embodiments the mean porosity of the microstructures may be greater than about 40%, 50%, 60%, 70% or even 80%. As to the pore themselves, they typically range in size from about 5 nm to about 400 nm with mean pore sizes preferably in the range of from about 20 nm to about 200 nm. In particularly preferred embodiments the mean pore size will be in the range of from about 50 nm to about 100 nm. As will be discussed in more detail below, it is a significant advantage of the present invention that the pore size and porosity may be closely controlled by careful selection of the incorporated components and production parameters.

In this regard, the particle morphology and/or hollow design of the particulates or perforated microstructures also plays an important role on the dispersibility or cohesiveness of the dry powder formulations disclosed herein. That is, it has been surprisingly discovered that the inherent cohesive character of fine powders can be overcome by lowering the van der Waals, electrostatic attractive and liquid bridging forces that typically exist between dry particles. More specifically, in concordance with the teachings herein, improved powder dispersibility may be provided by engineering the particle morphology and density, as well as control of humidity and charge. To that end, preferred embodiments of the present invention comprise perforated microstructures having pores, voids, hollows, defects or other interstitial spaces which reduce the surface contact area between particles thereby minimizing interparticle forces. In addition, the use of surfactants such as phospholipids and fluorinated blowing agents in accordance with the teachings herein may contribute to improvements in the flow properties of the powders by tempering the charge and strength of the electrostatic forces as well as moisture content.

Most fine powders (e.g. <5 $\mu$m) exhibit poor dispersibility which can be problematic when attempting to deliver, aerosolize and/or package the powders. In this respect the major forces which control particle interactions can typically be divided into long and short range forces. Long range forces include gravitational attractive forces and electrostatics, where the interaction varies as a square of the separation distance or particle diameter. Important short range forces for dry powders include van der Waals interactions, hydrogen bonding and liquid bridges. The latter two short range forces differ from the others in that they occur where there is already contact between particles. It is a major advantage of the present invention that these attractive forces may be substantially attenuated or reduced through the use of perforated microstructures as described herein.

Those skilled in the art will appreciate that the van der Waals (VDW) attractive force occurs at short range and depends, at least in part, on the surface contact between the interacting particles. When two particles approach each other the VDW forces increase with an increase in contact area. For two dry particles, the magnitude of the VDW interaction force, $F^0_{vdw}$, can be calculated using the following equation:

$$F^0_{vdw} = \frac{\hbar\omega}{8\pi d_0^2}\left[\frac{r_1 r_2}{r_1 + r_2}\right]$$

where $\hbar$ is Planck's constant, $\omega$ is the angular frequency, $d_0$ is the distance at which the adhesional force is at a maximum, and $r_1$, and $r_2$ are the radii of the two interacting particles. Accordingly, i will be appreciated that one way to minimize the magnitude and strength of the VDW force for dry powders is to decrease the interparticle area of contact. It is important to note that the magnitude of do is a reflection of this area of contact. The minimal area of contact between two opposing bodies will occur if the particles are perfect spheres. In addition, the area of contact will be further minimized if the particles are highly porous. Accordingly, the perforated microstructures of the present invention act to reduce interparticle contact and corresponding VOW attractive forces. It is important to note that this reduction in VDW forces is largely a result of the unique particle morphology of the powders of the present invention rather than an increase in geometric particle diameter. In this regard, it will be appreciated that particularly preferred embodiments of the present invention provide powders having average or small particulates (e.g. mean geometric diameter<10 $\mu$m) exhibiting relatively low VDW attractive forces.

Further, as indicated above, the electrostatic force affecting powders occurs when either or both of the particles are electrically charged. This phenomenon will result with either an attraction or repulsion between particles depending on the similarity or dissimilarity of charge. In the simplest case, the electric charges can be described using Coulomb's Law. One way to modulate or decrease the electrostatic forces between particles is if either or both particles have non-conducting surfaces. Thus, if the perforated microstructure powders comprise excipients, surfactants or active agents that are relatively nonconducting, then any charge generated in the particle will be unevenly distributed over the surface. As a result, the charge half-life of powders comprising non-conducting components will be relatively short since the retention of elevated charges is dictated by the resistivity of the material. Resistive or non-conducting components are materials which will neither function as an efficient electron donor or acceptor.

Derjaguin et al. (Muller, V. M., Yushchenko, V. S., and Derjaguin, B. V., J. Colloid Interface Sci. 1980, 77, 115–119), which is incorporated herein by reference, provide a list ranking molecular groups for their ability to accept or donate an electron. In this regard exemplary groups may be ranked as follows:

Donor:—$NH_2$>—$OH$>—$OR$>—$COOR$>—$CH_3$>—$C_6H_5$>-halogen>—$COOH$>—$CO$>—$CN$ Acceptor:

The present invention provides for the reduction of electrostatic effects in the disclosed powders though the use of relatively non-conductive materials. Using the above rankings, preferred non-conductive materials would include halogenated and/or hydrogenated components. Materials such as phospholipids and fluorinated blowing agents (which may be retained to some extent in spray dried powders) are preferred since they can provide resistance to particle charging. It will be appreciated that the retention of residual blowing agent (e.g. fluorochemicals) in the particles, even at relatively low levels, may help minimize charging of particulates or perforated microstructures as is typically imparted during spray drying and cyclone separation. Based on general electrostatic principles and the teachings herein, one skilled in the art would be able to identify additional materials that serve to reduce the electrostatic forces of the disclosed powders without undue experimentation. In this regard, highly charged agents can be electrostatically modified and controlled through simple pH adjustments or chelation with oppositely charged compounds, e.g. associating nucleic acids with cationic lipids. Further, if needed, the electrostatic forces can also be manipulated and minimized using electrification and charging techniques.

In addition to the surprising advantages described above, the present invention further provides for the attenuation or reduction of hydrogen and liquid bonding. As known to those skilled in the art, both hydrogen bonding and liquid bridging can result from moisture that is absorbed by the powder. In general, higher humidities produce higher interparticle forces for hydrophilic surfaces. This is a substantial problem in prior art pharmaceutical formulations for inhalation therapies which tend to employ relatively hydrophilic compounds such as lactose. However, in accordance with the teachings herein, adhesion forces due to adsorbed water can be modulated or reduced by increasing the hydrophobicity of the contacting surfaces. One skilled in the art can appreciate that an increase in particle hydrophobicity can be achieved through excipient selection and/or use a post-production spray drying coating technique such as employed using a fluidized bed. Thus, preferred excipients include hydrophobic surfactants such as phospholipids, fatty acid soaps and cholesterol. In view of the teachings herein, it is submitted that a skilled artisan would be able to identify materials exhibiting similar desirable properties without undue experimentation.

Whether they are to be used as a dry powder or combined with a nonaqueous suspension medium, the particulates or perforated microstructures will preferably be provided in a "dry" state. That is the microparticles will possess a moisture content that allows the powder to remain chemically and physically stable during storage at ambient temperature and easily dispersible. As such, the moisture content of the microparticles is typically less than 6% by weight, and preferably less 3% by weight. In some instances the moisture content will be as low as 1% by weight. Of course it will be appreciated that the moisture content is, at least in part, dictated by the formulation and is controlled by the process conditions employed, e.g., inlet temperature, feed concentration, pump rate, and blowing agent type, concentration and post drying.

As known by those skilled in the art, methods such as angle of repose or shear index can be used to assess the flow properties of dry powders. The angle of repose is defined as the angle formed when a cone of powder is poured onto a flat surface. Powders having an angle of repose ranging from 45° to 20° are preferred and indicate suitable powder flow. More particularly, powders which possess an angle of repose between 33° and 20° flow with relatively low shear forces and are especially useful in pharmaceutical preparations for use in inhalation therapies (e.g. DPIs). The shear index, though more time consuming to measure than angle of repose, is considered more reliable and easy to determine.

Those skilled in the art will appreciate that the experimental procedure outlined by Amidon and Houghton (G. E. Amidon, and M. E. Houghton, Pharm. Manuf., 2, 20, 1985, incorporated herein by reference) can be used estimate the shear index for the purposes of the present invention. As described in S. Kocova and N. Pilpel, J. Pharm. Pharmacol. 8, 33–55, 1973, also incorporated herein by reference, the shear index is estimated from powder parameters such as, yield stress, effective angle of internal friction, tensile strength, and specific cohesion. In the present invention powders having a shear index less than about 0.98 are desirable. More preferably, powders used in the disclosed compositions, methods and systems will have shear indices less than about 1.1. In particularly preferred embodiments the shear index will be less than about 1.3 or even less than about 1.5. Of course powders having different shear indices may be used provided the result in the effective deposition of the active or bioactive agent at the site of interest.

It will also be appreciated that the flow properties of powders have been shown to correlate well with bulk density measurements. In this regard, conventional prior art thinking (C. F. Harwood, J. Pharm Sci., 60, 161–163, 1971) held that an increase in bulk density correlates with improved flow properties as predicted by the shear index of the material. Conversely, it has surprisingly been found that, for the perforated microstructures of the present invention, superior flow properties were exhibited by powders having relatively low bulk densities. That is, the hollow porous powders of the present invention exhibited superior flow properties over powders substantially devoid of pores. To that end, it has been found that it is possible to provide powders having bulk densities of less than 0.5 g/cm$^3$ that exhibit particularly favorable flow properties. More surprisingly, it has been found that it is possible to provide perforated microstructure powders having bulk densities of less than 0.3 g/cm$^3$, less than about 0.1 g/cm$^3$ or even on the order of 0.05 g/cm$^3$ that exhibit excellent flow properties. The ability to produce low bulk density powders having superior flowability further accentuates the novel and unexpected nature of the present invention.

These low bulk densities are particularly advantageous when using the disclosed powders in conjunction with DPIs. Specifically, by affording powder formulations having extraordinarily low bulk density, the present invention allows for reduction of the minimal filling weight that is commercially feasible for use in dry powder inhalation devices. That is, most unit dose containers designed for DPIs are filled using fixed volume or gravimetric techniques. Contrary to many prior art formulations, the present invention provides powders wherein bioactive agent and the incipients or bulking agents make-up the entire inhaled particle. By providing particles with very low bulk density, the minimum powder mass that can be filled into a unit dose container is reduced, which eliminates the need for carrier particles. That is, the relatively low density of the powders of the present invention provides for the reproducible administration of relatively low dose pharmaceutical compounds without the use of carrier particles. Moreover, the elimination of carrier particles acts to minimize throat deposition and any "gag" effect, since the large lactose particles of prior art formulations tend to impact the throat and upper airways due to their size.

It will be appreciated that the reduced attractive forces (e.g. van der Waals, electrostatic, hydrogen and liquid bridging, etc.) and excellent flowability provided by the perforated microstructure powders make them particularly useful in preparations for inhalation therapies (e.g. in inhalation devices such as DPIs, MDIs, nebulizers). Along with the superior flowability, the perforated or porous and/or hollow design of the microstructures also plays an important role in the resulting aerosol properties of the powder when discharged. This phenomenon holds true for particulates or perforated microstructures aerosolized as a suspension, as in the case of an MDI or a nebulizer, or delivery of perforated microstructures in dry form as in the case of a DPI. In this respect the perforated structure and relatively high surface area of the dispersed microparticles enables them to be carried along in the flow of gases during inhalation with greater ease for longer distances than non-perforated particles of comparable size.

More particularly, because of their high porosity, the density of the particles is significantly less than 1.0 g/cm$^3$, typically less than 0.5 g/cm$^3$, more often on the order of 0.1 g/cm$^3$, and as low as 0.01 g/cm$^3$. Unlike the geometric particle size, the aerodynamic particle size, $d_{aer}$, of the perforated microstructures depends substantially on the particle density, $\rho$: $d_{aer}=d_{geo}\sqrt{\rho}$, where $d_{geo}$ is the geometric diameter. For a particle density of 0.1 g/cm$^3$, $d_{aer}$ will be roughly three times smaller than $d_{geo}$, leading to increased particle deposition into the peripheral regions of the lung and correspondingly less deposition in the throat. In this regard, the mean aerodynamic diameter of the perforated microstructures is preferably less than about 5 μm, more preferably less than about 3 μm, and, in particularly preferred embodiments, less than about 2 μm. Such particle distributions will act to increase the deep lung deposition of the bioactive agent whether administered using a DPI, MDI or nebulizer.

As will be shown subsequently in the Examples, the particle size distribution of the aerosol formulations of the present invention are measurable by conventional techniques such as, for example, cascade impaction or by time of flight analytical methods. In addition, determination of the emitted dose from inhalation devices were done according to the proposed U.S. Pharmacopeia method (Pharmacopeial Previews, 22(1996) 3065) which is incorporated herein by reference. These and related techniques enable the "fine particle fraction" of the aerosol, which corresponds to those particulates that are likely to effectively deposited in the lung, to be calculated. As used herein the phrase "fine particle fraction" refers to the percentage of the total amount of active medicament delivered per actuation from the mouthpiece of a DPI, MDI or nebulizer onto plates 2–7 of an 8 stage Andersen cascade impactor. Based on such measurements the formulations of the present invention will preferably have a fine particle fraction of approximately 20% or more by weight of the perforated microstructures (w/w), more preferably they will exhibit a fine particle fraction of from about 25% to 90% w/w, and even more preferably from about 30 to 80% w/w. In selected embodiments the present invention will preferably comprise a fine particle fraction of greater than about 30%, 40%, 50%, 60%, 70%, 80% or even 90% by weight.

Further, it has also been found that the formulations of the present invention exhibit relatively low deposition rates, when compared with prior art preparations, on the induction port and onto plates 0 and 1 of the impactor. Deposition on these components is linked with deposition in the throat in humans. More specifically, most commercially available MDIs and DPIs have simulated throat depositions of approximately 40–70% (w/w) of the total dose, while the formulations of the present invention typically deposit less than about 20% w/w. Accordingly, preferred embodiments of the present invention have simulated throat depositions of less than about 40%, 35%, 30%, 25%, 20%, 15% or even 10% w/w. Those skilled in the art will appreciate that significant decrease in throat deposition provided by the present invention will result in a corresponding decrease in associated local side-effects such as throat irritation.

With respect to the advantageous deposition profile provided by the instant invention it is well known that MDI propellants typically force suspended particles out of the device at a high velocity towards the back of the throat. Since prior art formulations typically contain a significant percentage of large particles and/or aggregates, as much as two-thirds or more of the emitted dose may impact the throat. Moreover, the undesirable delivery profile of conventional powder preparations is also exhibited under conditions of low particle velocity, as occurs with DPI devices. In general, this problem is inherent when aerosolizing solid, dense, particulates which are subject to aggregation. Yet, as discussed above, the novel and unexpected properties of the stabilized dispersions of the present invention result in surprisingly low throat deposition upon administration from inhalation device such as a DPI, MDI atomizer or nebulizer.

While not wishing to be bound by any particular theory, it appears that the reduced throat deposition provided by the instant invention results from decreases in particle aggregation and from the hallow and/or porous morphology of the incorporated microstructures. That is, the hollow and porous nature of the dispersed microstructures slows the velocity of particles in the propellant stream (or gas stream in the case of DPIs), just as a hollow/porous whiffle ball decelerates faster than a baseball. Thus, rather than impacting and sticking to the back of the throat, the relatively slow traveling particles are subject to inhalation by the patient. Moreover, the highly porous nature of the particles allows the propellant within the perforated microstructure to rapidly leave and the particle density to drop before impacting the throat. Accordingly, a substantially higher percentage of the administered bioactive agent is deposited in the pulmonary air passages where it may be efficiently absorbed.

E. Powder Formation

As seen from the passages above, various components may be associated with, or incorporated in the microparticulates of the present invention. Similarly, several techniques may be used to provide particulates having the desired morphology (e.g. a perforated or hollow/porous configuration), dispersibility and density. Among other methods, particulates compatible with the instant invention may be formed by techniques including spray drying, vacuum drying, solvent extraction, emulsification, lyophilization and combinations thereof. It will further be appreciated that the basic concepts of many of these techniques are well known in the prior art and would not, in view of the teachings herein, require undue experimentation to adapt them so as to provide the desired particle configuration and/or density.

While several procedures are generally compatible with the present invention, particularly preferred embodiments typically comprise particulates or perforated microstructures formed by spray drying. As is well known, spray drying is a one-step process that converts a liquid feed to a dried particulate form. With respect to pharmaceutical applications, it will be appreciated that spray drying has been used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996, which is incorporated herein by reference.

In general, spray drying consists of bringing together a highly dispersed liquid, and a sufficient volume of hot air to produce evaporation and drying of the liquid droplets. The preparation to be spray dried or feed (or feed stock) can be any solution, course suspension, slurry, colloidal dispersion, or paste that may be atomized using the selected spray drying apparatus. In preferred embodiments the feed stock will comprise a colloidal system such as an emulsion, reverse emulsion, microemulsion, multiple emulsion, particulate dispersion, or slurry. Typically the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Buchi Ltd. or Niro Corp. will effectively produce particles of desired size, morphology and density.

It will further be appreciated that these spray dryers, and specifically their atomizers, may be modified or customized for specialized applications, i.e. the simultaneous spraying of two solutions using a double nozzle technique. More specifically, a water-in-oil emulsion can be atomized from one nozzle and a solution containing an anti-adherent such as mannitol can be co-atomized from a second nozzle. In other cases it may be desirable to push the feed solution though a custom designed nozzle using a high pressure liquid chromatography (HPLC) pump. Provided that microstructures comprising the desired morphology and/or composition are produced, the choice of apparatus is not critical and would readily be apparent to the skilled artisan in view of the teachings herein.

While the resulting spray-dried powders typically are approximately spherical in shape, nearly uniform in size and frequently are hollow, there may be some degree of irregularity in shape depending upon the incorporated medicament and the spray drying conditions. In many instances dispersion stability and dispersibility of particulates or perforated microstructures appears to be improved if an inflating agent (or blowing agent) is used in their production. Particularly preferred embodiments may comprise an emulsion with the inflating agent as the disperse or continuous phase. The inflating agent is preferably dispersed with a surfactant solution, using, for instance, a commercially available microfluidizer at a pressure of about 5000 to 15,000 psi. This process forms an emulsion, preferably stabilized by an incorporated surfactant, typically comprising submicron droplets of water immiscible blowing agent dispersed in an aqueous continuous phase. The formation of such emulsions using this and other techniques are common and well known to those in the art. The blowing agent is preferably a fluorinated compound (e.g. perfluorohexane, perfluorooctyl, bromide, perfluorodecalin, perfluorobutyl ethane) which vaporizes during the spray-drying process, leaving behind, in selected embodiments, relatively hollow, porous aerodynamically light microspheres. As will be discussed in more detail below, other suitable liquid blowing agents include nonfluorinated oils, chloroform, Freons, ethyl acetate, alcohols and hydrocarbons. Nitrogen and carbon dioxide gases are also contemplated as suitable blowing agents.

Besides the aforementioned compounds, inorganic and organic substances which can be removed under reduced pressure by sublimation in a post-production step are also compatible with the instant invention. These sublimating compounds can be dissolved or dispersed as micronized crystals in the spray drying feed solution and include ammonium carbonate and camphor. Other compounds compatible with the present invention comprise rigidifying solid structures which can be dispersed in the feed solution or prepared in-situ. These structures are then extracted after the initial particle generation using a post-production solvent extraction step. For example, latex particles can be dispersed and subsequently dried with other wall forming compounds, followed by extraction with a suitable solvent.

Although the particulates are preferably formed using a blowing agent as described above, it will be appreciated that, in some instances, no additional blowing agent is required and an aqueous dispersion of the medicament and/or excipients and surfactant(s) are spray dried directly. In such cases, the formulation may be amenable to process conditions (e.g., elevated temperatures) that may lead to the formation of hollow, relatively porous microparticles. Moreover, the medicament may possess special physicochemical properties (e.g., high crystallinity, elevated melting temperature, surface activity, etc.) that makes it particularly suitable for use in such techniques.

When a blowing agent is employed, the degree of porosity and dispersibility of the resulting particulates appears to depend, at least in part, on the nature of the blowing agent, its concentration in the feed stock (e.g. as an emulsion), and the spray drying conditions. With respect to controlling porosity and, in suspensions, dispersibility it has surprisingly been found that the use of compounds, heretofore unappreciated as blowing agents, may provide perforated microstructures having particularly desirable characteristics. More particularly, in this novel and unexpected aspect of the present invention it has been found that the use of fluorinated compounds having relatively high boiling points (i.e. greater than about 40° C.) may be used to produce particulates that are especially porous. Such perforated microstructures are especially suitable for inhalation therapies. In this regard it is possible to use fluorinated or partially fluorinated blowing agents having boiling points of greater than about 40° C., 50° C., 60° C., 70° C., 80° C., 90° C. or even 95° C. Particularly preferred blowing agents have boiling points greater than the boiling point of water, i.e. greater than 100° C.(e.g. perflubron, perfluorodecalin). In addition blowing agents with relatively low water solubility ($<10^{-6}$ M) are preferred since they facilitate the production of stable emulsion dispersions with mean weighted particle diameters less than 0.3 $\mu$m.

As previously described, these blowing agents will preferably be incorporated in an emulsified feed stock prior to spray drying. For the purposes of the present invention this feed stock will also preferably comprise one or more bioactive agents, one or more surfactants or one or more excipients. Of course, combinations of the aforementioned components are also within the scope of the invention. While high boiling (>100° C.) fluorinated blowing agents comprise one preferred aspect of the present invention, it will be appreciated that nonfluorinated blowing agents with similar boiling points (>100° C.) may be also be used to provide compatible particulates. Exemplary nonfluorinated blowing agents suitable for use in the present invention comprise the formula:

$$R^1—X—R^2 \text{ or } R^1—X$$

wherein: $R^1$ or $R^2$ is hydrogen, alkyl, alkenyl, alkynl, aromatic, cyclic or combinations thereof, X is any group containing carbon, sulfur, nitrogen, halogens, phosphorus, oxygen and combinations thereof.

While not limiting the invention in any way it is hypothesized that, as the aqueous feed component evaporates during spray drying it leaves a thin crust at the surface of the particle. The resulting particle wall or crust formed during the initial moments of spray drying appears to trap any high boiling blowing agents as hundreds of emulsion droplets (ca. 200–300 nm). As the drying process continues, the pressure inside the particulate increases thereby vaporizing at least part of the incorporated blowing agent and forcing it through the relatively thin crust. This venting or outgassing apparently leads to the formation of pores or other defects in the microstructure. At the same time remaining particulate components (possibly including some blowing agent) migrate from the interior to the surface as the particle solidifies. This migration apparently slows during the drying process as a result of increased resistance to mass transfer caused by an increased internal viscosity. Once the migration ceases the particle solidifies, leaving voids, pores, defects, hollows, spaces, interstitial spaces, apertures, perforations or holes. The number of pores or defects, their size, and the resulting wall thickness is largely dependent on the formulation and/or the nature of the selected blowing agent (e.g. boiling point), its concentration in the emulsion, total solids concentration, and the spray-drying conditions. As alluded to throughout the specification, this preferred particle morphology appears to contribute, at least in part, to the improved powder dispersibility, suspension stability and aerodynamics.

It has been surprisingly found that substantial amounts of these relatively high boiling blowing agents may be retained in the resulting spray dried product. That is, spray dried particulates as described herein may comprise as much as 1%, 3%, 5%, 10%, 20%, 30% or even 40% w/w of residual blowing agent. In such cases, higher production yields were obtained as a result an increased particle density caused by this retained blowing agent. It will be appreciated by those skilled in the art that retained fluorinated blowing agent may alter the surface characteristics of the particulates, thereby minimizing particle aggregation during processing and further increasing dispersion stability. Residual fluorinated blowing agent in the powders may also reduce the cohesive forces between particles by providing a barrier or by attenuating the attractive forces produced during manufacturing (e.g., electrostatics). This reduction in cohesive forces may be particularly advantageous when using the disclosed microstructures in conjunction with dry powder inhalers.

Furthermore, the amount of residual blowing agent can be controlled through the process conditions (such as outlet temperature), blowing agent concentration, or boiling point. If the outlet temperature is at or above the boiling point, the blowing agent escapes the particle and the production yield decreases. Preferred outlet temperature will generally be operated at 20, 30, 40, 50, 60, 70, 80, 90 or even 100° C. less than the blowing agent boiling point. More preferably the temperature differential between the outlet temperature and the boiling point will range from 50 to 150° C. It will be appreciated by those skilled in the art that particle porosity, production yield, electrostatics and dispersibility can be optimized by first identifying the range of process conditions (e.g., outlet temperature) that are suitable for the selected active agents and/or excipients. The preferred blowing agent can be then chosen using the maximum outlet temperature such that the temperature differential with be at least 20 and up to 150° C. In some cases, the temperature differential can be outside this range such as, for example, when producing the particulates under supercritical conditions or using lyophilization techniques. Those skilled in the art will further appreciate that the preferred concentration of blowing agent can be determined without undue experimentation using techniques similar to those described in the Examples herein.

While residual blowing agent may be advantageous in selected embodiments it may be desirable to substantially remove any blowing agent from the spray dried product. In this respect, the residual blowing agent can easily be removed with a post-production evaporation step in a vacuum oven. Moreover, such post production techniques may be used to provide perforations in the particulates. For example, pores may be formed by spray drying a bioactive agent and an excipient that can be removed from the formed particulates under a vacuum.

In any event, typical concentrations of blowing agent in the feed stock are between 2% and 50% v/v, and more preferably between about 10% to 45% v/v. In other embodiments blowing agent concentrations will preferably be greater than about 5%, 10%, 15%, 20%, 25% or even 30% v/v. Yet other feed stock emulsions may comprise 35%, 40%, 45% or even 50% v/v of the selected compound.

In preferred embodiments, another method of identifying the concentration of blowing agent used in the feed is to provide it as a ratio of the concentration of the blowing agent to that of the stabilizing surfactant (e.g. phosphatidylcholine or PC) in the precursor or feed emulsion. For fluorocarbon blowing agents (e.g. perfluorooctyl bromide), and for the purposes of explanation, this ratio has been termed the PFC/PC ratio. More generally, it will be appreciated that compatible blowing agents and/or surfactants may be substituted for the exemplary compounds without falling outside of the scope of the present invention. In any event, the typical PFC/PC ratio will range from about 1 to about 60 and, more preferably, from about 10 to about 50. For preferred embodiments the ratio will generally be greater than about 5, 10, 20, 25, 30, 40 or even 50. It should be appreciated that the use of higher PFC/PC ratios generally provides structures of a more hollow and porous nature. More particularly, those methods employing a PFC/PC ratio of greater than about 4.8 tended to provide structures that are particularly compatible with the dry power formulations and dispersions disclosed herein.

While relatively high boiling point blowing agents comprise one preferred aspect of the instant invention, it will be appreciated other blowing or inflating agents may also be used to provide compatible microstructures. As such, the blowing agent may comprise any volatile substance which can be incorporated into the feed solution for the purpose of producing the desired microstructures. The blowing agent may be removed during the initial drying process or during a post-production step such as vacuum drying or solvent extraction. Suitable agents include:

1. Dissolved low-boiling (below 100° C.) agents miscible with aqueous solutions, such as methylene chloride, acetone, ethyl acetate, and alcohols used to saturate the solution.
2. A gas, such as $CO_2$ or $N_2$, or liquid such as Freons, CFCs, HFAs, PFCs, HFCs, HFBs, fluoroalkanes and hydrocarbons, used at elevated pressure.
3. Emulsions of immiscible low-boiling (below 100° C.) liquids suitable for use with the present invention are generally of the formula:

$$R^1—X—R^2 \text{ or } R^1—X$$

wherein: $R^1$ or $R^2$ is hydrogen, alkyl, alkenyl, alkynl, aromatic, cyclic or combinations thereof, X is any groups containing carbon, sulfur, nitrogen, halogens, phosphorus, oxygen and combinations thereof.

4. Dissolved or dispersed salts or organic substances which can be removed under reduced pressure by sublimation in a post-production step, such as ammonium salts, camphor, etc.
5. Dispersed solids which can be extracted after the initial particle generation using a post-production solvent extraction step.

With respect to lower boiling point inflating agents, they are typically added to the feed stock in quantities of about 1% to 40% v/v of the surfactant solution. Approximately 15% v/v inflating agent has been found to produce a spray dried powder that may be used with the methods of the present invention.

Regardless of which blowing agent is ultimately selected, it has been found that compatible particulates may be produced using commercially available equipment such as a Büchi mini spray drier (model B-191, Switzerland). As will be appreciated by those skilled in the art, the inlet temperature and the outlet temperature of the spray drier may be adjusted to provide the desired particle size and to maintain the activity of the incorporated bioactive agent. In this regard, the inlet and outlet temperatures are adjusted depending on the melting characteristics of the formulation components and the composition of the feed stock. The inlet temperature may thus be between 60° C. and 170° C., with the outlet temperatures of about 40° C. to 120° C. depending on the composition of the feed and the desired particulate characteristics. Preferably these temperatures will be from 90° C. to 120° C. for the inlet and from 60° C. to 90° C. for the outlet. The flow rate which is used in the spray drying equipment will generally be about 3 ml per minute to about 15 ml per minute. The atomizer air flow rate will vary between values of 25 liters per minute to about 50 liters per minute. Commercially available spray dryers are well known to those in the art, and suitable settings for any particular dispersion can be readily determined through standard empirical testing, with due reference to the examples that follow.

Although the microparticulates are preferably formed using fluorinated blowing agents in the form of an emulsion, it will be appreciated that nonfluorinated oils may be used to increase the loading capacity of the bioactive agents without compromising the microstructure. In this case, selection of the nonfluorinated oil is based upon the solubility of the active or bioactive agent, water solubility, boiling point, and flash point. The bioactive agent will be dissolved in the oil and subsequently emulsified in the feed solution. Preferably the oil will have substantial solubilization capacity with respect to the selected agent, low water solubility (<$10^{31}$M), boiling point greater than water and a flash point greater than the drying outlet temperature. The addition of surfactants, and co-solvents to the nonfluorinated oil to increase the solubilization capacity is also within the scope of the present invention.

In particularly preferred embodiments nonfluorinated oils may be used to solubilize bioactive agents that have limited solubility in aqueous compositions. The use of nonfluorinated oils is of particular use for increasing the loading capacity of hydrophobic peptides and proteins. Preferably the oil or oil mixture for solubilizing these compounds will have a refractive index between 1.36 and 1.41 (e.g. ethyl butyrate, butyl carbonate, dibutyl ether). In addition, process conditions, such as temperature and pressure, may be adjusted in order to boost solubility of the selected agent. It will be appreciated that selection of an appropriate oil or oil mixtures and processing conditions to maximize the loading capacity of an agent are well within the purview of a skilled artisan in view of the teachings herein and may be accomplished without undue experimentation.

Particularly preferred embodiments of the present invention comprise spray drying preparations comprising a surfactant such as a phospholipid and at least one bioactive agent. Other embodiments include spray drying preparations that may further include an excipient comprising a hydrophilic moiety such as, for example, a carbohydrate (i.e. glucose, lactose, or starch) in addition to any selected surfactant. In this regard, various starches and derivatized starches are particularly suitable for use in the present invention. Other optional components may include conventional viscosity modifiers, buffers such as phosphate buffers or other conventional biocompatible buffers or pH adjusting agents such as acids or bases, and osmotic agents (to provide isotonicity, hyperosmolarity, or hyposmolarity). Examples of suitable salts include sodium phosphate (both monobasic and dibasic), sodium chloride, calcium phosphate, calcium chloride and other physiologically acceptable salts.

Whatever components are selected, the first step in particulate production typically comprises feed stock preparation. Preferably the selected drug is dissolved in water to produce a concentrated solution. The drug may also be dispersed directly in the emulsion, particularly in the case of water insoluble agents. Alternatively, the drug may be incorporated in the form of a solid particulate dispersion. The concentration of the active or bioactive agent used is dependent on the amount of agent required in the final powder and the performance of the delivery device employed (e.g., the fine particle dose for a MDI or DPI). As needed, cosurfactants such as poloxamer 188 or span 80 may be dispersed into this annex solution. Additionally, excipients such as sugars and starches can also be added.

In selected embodiments an oil-in-water emulsion is then formed in a separate vessel. The oil employed is preferably a fluorocarbon (e.g., perfluorooctyl bromide, perfluorodecalin) which is emulsified using a surfactant such as a long chain saturated phospholipid. For example, one gram of phospholipid may be homogenized in 150 g hot distilled water (e.g., 60° C.) using a suitable high shear mechanical mixer (e.g., Ultra-Turrax model T-25 mixer) at 8000 rpm for 2 to 5 minutes. Typically 5 to 25 g of fluorocarbon is added dropwise to the dispersed surfactant solution while mixing. The resulting perfluorocarbon in water emulsion is then processed using a high pressure homogenizer to reduce the particle size. For example, the emulsion may be processed at 12,000 to 18,000 psi, 5 discrete passes and kept at 50 to 80° C.

The bioactive agent solution and perfluorocarbon emulsion may then be combined and fed into the spray dryer. Typically the two preparations will be miscible as the emulsion will preferably comprise an aqueous continuous phase. While the bioactive agent is solubilized separately for the purposes of the instant discussion it will be appreciated that, in other embodiments, the active or bioactive agent may be solubilized (or dispersed) directly in the emulsion. In such cases, the active or bioactive emulsion is simply spray dried without combining a separate drug preparation.

In any event, operating conditions such as inlet and outlet temperature, feed rate, atomization pressure, flow rate of the drying air, and nozzle configuration can be adjusted in accordance with the manufacturer's guidelines in order to produce the required particle size, and production yield of the resulting dry microstructures. Exemplary settings are as follows: an air inlet temperature between 60° C. and 170° C.; an air outlet between 40° C. to 120° C.; a feed rate between 3 ml to about 15 ml per minute; and an aspiration air flow of 300 L/min. and an atomization air flow rate between 25 to 50 L/min. The selection of appropriate apparatus and processing conditions are well within the purview of a skilled artisan in view of the teachings herein and may be accomplished without undue experimentation. In any event, the use of these and substantially equivalent methods provide for the formation of hollow porous aerodynamically light microspheres with particle diameters appropriate for aerosol deposition into the lung, microstructures that are both hollow and porous, almost honeycombed or foam-like in appearance. In especially preferred embodiments the perforated microstructures comprise hollow, porous spray dried microspheres.

Along with spray drying, perforated microstructures useful in the present invention may be formed by lyophilization. Those skilled in the art will appreciate that lyophilization is a freeze-drying process in which water is sublimed from the composition after it is frozen. The particular advantage associated with the lyophilization process is that biologics and other pharmaceuticals that are relatively unstable in an aqueous solution can be dried without elevated temperatures (thereby eliminating the adverse thermal effects), and then stored in a dry state where there are few stability problems. With respect to the instant invention such techniques are particularly compatible with the incorporation of peptides, proteins, genetic material and other natural and synthetic macromolecules in particulates or perforated microstructures without compromising physiological activity. Methods for providing lyophilized particulates are known to those of skill in the art and it would clearly not require undue experimentation to provide compatible microstructures in accordance with the teachings herein. The lyophilized cake containing a fine foam-like structure can be micronized using techniques known in the art to provide particles having mean diameters under 5 $\mu$m or 10 $\mu$m. Accordingly, to the extent that lyophilization processes may be used to provide microstructures having the desired characteristics they are expressly contemplated as being within the scope of the instant invention.

Besides the aforementioned techniques, the particulates and perforated microstructures of the present invention may also be formed using a method where a feed solution (either emulsion or aqueous) containing wall forming agents is rapidly added to a reservoir of heated oil (e.g. perflubron or other high boiling FCs) under reduced pressure. The water and volatile solvents of the feed solution rapidly boils and are evaporated. This process may be used to provide a perforated structure from wall forming agents similar to puffed rice or popcorn. Preferably the wall forming agents are insoluble in the heated oil. The resulting particles can then separated from the heated oil using a filtering technique and subsequently dried under vacuum.

Additionally, the particles or perforated microstructures of the present invention may also be formed using a double emulsion method. In the double emulsion method the medicament is first dispersed in a polymer dissolved in an organic solvent (e.g. methylene chloride) by sonication or homogenization. This primary emulsion is then stabilized by forming a multiple emulsion in a continuous aqueous phase containing an emulsifier such as polyvinylalcohol. Evaporation or extraction using conventional techniques and apparatus then removes the organic solvent. The resulting microparticles are then washed, filtered and dried prior to use or combining them with an appropriate suspension medium in accordance with the present invention.

F. Administration

Whatever method is ultimately selected for production of the microparticulates, the resulting powders have a number of advantageous properties that allow them to be effectively used in either a powdered form or as a dispersion comprising a nonaqueous suspension medium. In particularly preferred embodiments the bioactive compositions, whether in the form of a dry powder or dispersion, will be administered to the mucosal surface of the respiratory tract (i.e., the pulmonary and/or the nasal tract) via inhalation therapy. Such administration may be effected using MDIs, DPIs, nebulizers, nasal pumps, atomizers, spray bottles or by direct instillation in the form of drops. However, while inhalation therapies are extremely compatible with the present invention, it will be appreciated that other forms and/or routes of administration are also useful.

In this regard, the powders and stabilized dispersions of the present invention may also be used for the localized or systemic administration of compounds to any location of the body. Accordingly, it should be emphasized that, in preferred embodiments, the preparations may be administered using a number of different routes including, but not limited to, topical, intramuscular, transdermal, intradermal, intraperitoneal, nasal, pulmonary, buccal, vaginal, rectal, aural, oral or ocular administration. Preferred target sites may be found in, for example, the gastrointestinal tract, urogenital tract or respiratory tract. More generally, the stabilized dispersions of the present invention may be used to deliver agents topically or by administration to any body cavity. In preferred embodiments the body cavity is selected from the group consisting of the peritoneum, sinus cavity, rectum, urethra, stomach, nasal cavity, vagina, auditory meatus, oral cavity, buccal pouch and pleura. Those skilled in the art will appreciate that the selected route of administration will largely be determined by the choice of bioactive agent and the desired response of the subject.

With regard to the delivery of the disclosed powders or stabilized dispersions, another aspect of the present invention is directed to systems for the administration of one or more bioactive agents or biologics to a patient. As alluded to above, exemplary inhalation devices compatible with the present invention may comprise an atomizer, nasal pump, a sprayer or spray bottle, a dry powder inhaler, a metered dose inhaler or a nebulizer. In preferred embodiments, these inhalation systems will deliver the bioactive agent to the desired physiological site (e.g. a mucosal surface) as an aerosol. For the purposes of the instant application the term "aerosolized" shall be held to mean a gaseous suspension of fine solid or liquid particles unless otherwise dictated by contextual restraints. That is, an aerosol or aerosolized medicament may be generated, for example, by a dry powder inhaler, a metered dose inhaler, an atomizer, a spray bottle or a nebulizer. Of course, as explained in more detail below, the compositions of the present invention may also be delivered directly (e.g. by conventional injection or needleless injection) or using such techniques as liquid dose instillation. As such, a further aspect of the present invention is directed to needleless injectors (e.g. pressurized gas guns) comprising the disclosed powders or dispersions.

F(i). Dry Powder Inhalers

With respect to inhalation therapies, those skilled in the art will appreciate that the powders of the present invention, particularly those comprising perforated microstructures, are particularly useful in DPIs. Conventional DPIs, or dry powder inhalers, comprise powdered formulations and devices where a predetermined dose of medicament, either alone or in a blend with lactose carrier particles, is delivered as a fine mist or aerosol of dry powder for inhalation. Useful DPI medicaments are typically formulated so that they readily disperse into discrete particles with a size rage between 0.5 to 20 $\mu$m. The powder is actuated either by inspiration or by some external delivery force, such as pressurized air. DPI formulations are typically packaged in single dose units or they employ reservoir systems capable of metering multiple doses with manual transfer of the dose to the device.

DPIs are generally classified based on the dose delivery system employed. In this respect, the two major types of DPIs comprise unit dose delivery devices and bulk reservoir delivery systems. As used herein, the term "reservoir" shall be used in a general sense and held to encompass both configurations unless otherwise dictated by contextual restraints. In any event, unit dose delivery systems require the dose of powder formulation presented to the device as a single unit. With this system, the formulation is prefilled into dosing wells which may be foil-packaged or presented in blister strips to prevent moisture ingress. Other unit dose packages include hard gelatin capsules. Most unit dose containers designed for DPIs are filled using a fixed volume technique. As a result, there are physical limitations (here density) to the minimal dose that can be metered into a unit package, which is dictated by the powder flowability and bulk density.

As previously alluded to, the powders of the present invention obviate many of the difficulties associated with prior art carrier preparations. That is, an improvement in DPI performance may be provided by adjusting the particle size, aerodynamics, morphology and density, humidity and charge as disclosed herein. In this respect the present invention provides for formulations wherein the medicament and the incipients or bulking agents are preferably associated with or comprise perforated microstructures. As set forth above, preferred compositions according to the present invention typically yield powders with bulk densities less than 0.1 g/cm$^3$ and often less than 0.05 g/cm$^3$. It will be appreciated that providing powders having bulk densities an order of a magnitude less than conventional DPI formulations allows for much lower doses of the selected bioactive agent to be filled into a unit dose container or metered via reservoir-based DPIs. The ability to effectively meter small quantities is significant for relatively potent bioactive agents such as hormones. Moreover, the ability to effectively deliver particulates without associated carrier particles simplifies product formulation, filling and reduces undesirable side effects.

It will be appreciated that the powders of the present invention are particularly effective at delivering relatively high doses of bioactive agent in a single actuation. Unlike prior art formulations, the powdered formulations do not require the use of bulking agents for effective filling and delivery and may therefore comprise higher levels of bioactive agent on a weight by weight basis. Significantly, the disclosed compositions may be used to deliver as much as approximately 10 mg of bioactive agent in a single actuation. Such advantages may be particularly important when delivering, for example, immunomodulators or antibodies for passive immunization, that may not be as potent as other compatible agents. Of course, while the instant discussion is specifically directed to the use of DPIs, this same advantage is equally applicable to dispersion formulations and other forms of administration such as MDIs, nasal pumps and needleless injectors.

In addition to the aforementioned advantages, preferred embodiments of the present invention exhibit favorable aerodynamic properties that make them particularly effective for use in DPIs. More specifically, the perforated structure and relatively high surface area of the microparticles enables them to be carried along in the flow of gases during inhalation with greater ease and for longer distances than relatively non-perforated particles of comparable size. Because of their high porosity and low density, administration of perforated microstructures with a DPI provides for increased particle deposition at target sites such as mucosal surfaces in the nasal passages and peripheral regions of the lung with correspondingly less deposition in the throat. Such particle distribution may be employed to increase the deep lung deposition of the administered agent that is preferable for systemic administration. Moreover, in a substantial improvement over prior art DPI preparations the low-density, highly porous powders of the present invention preferably eliminate the need for carrier particles cl F(ii).

Stabilized Dispersions

Along with their use in a dry powder configuration, it will be appreciated that the powders of the present invention may be incorporated in a suspension medium to provide stabilized dispersions. Preferably, the stabilized dispersions will comprise a nonaqueous suspension medium. Among other uses, the stabilized dispersions provide for the effective delivery of bioactive agents to the pulmonary air passages of a patient using MDIs, atomizers or spray bottles, nasal pumps, needleless injectors, nebulizers or liquid dose instillation (LDI techniques).

Those skilled in the art will appreciate the enhanced stability of the disclosed dispersions or suspensions is largely achieved by lowering the van der Waals attractive forces between the suspended particles, and by reducing the differences in density between the suspension medium and the particles. In accordance with the teachings herein, the increases in suspension stability may be imparted by engineering perforated microstructures which are then dispersed in a compatible suspension medium. As discussed above, the perforated microstructures comprise pores, voids, hollows, defects or other interstitial spaces that allow the fluid suspension medium to freely permeate or perfuse the particulate boundary. Particularly preferred embodiments comprise perforated microstructures that are both hollow and porous, almost honeycombed or foam-like in appearance. In especially preferred embodiments the perforated microstructures comprise hollow, porous spray dried microspheres. Of course, in other embodiments, including those comprising relatively nonporous, solid particulates, enhanced stability may be imparted through the selection of particulate components (e.g. surfactants).

When perforated microstructures are placed in the suspension medium (i.e. a hydrofluoroalkane propellant or liquid fluorocarbon), the suspension medium is able to permeate the particles, thereby creating a "homodispersion", wherein both the continuous and dispersed phases are indistinguishable. Since the defined or "virtual" particles (i.e. comprising the volume circumscribed by the microparticulate matrix) are made up almost entirely of the medium in which they are suspended, the forces driving particle aggregation (flocculation) are minimized. Additionally, the differences in density between the defined particles and the continuous phase are minimized by having the microstructures filled with the medium, thereby effectively slowing particle creaming or sedimentation. As such, the particulates and stabilized suspensions of the present invention are particularly compatible with many aerosolization techniques, such as MDI, atomization via a spray bottle, nasal pumps, nebulization and the like. Moreover, the stabilized dispersions are compatible with other routes of administration including, but not limited to, liquid dose instillation, needleless injection, conventional injection and topical applications.

Unlike prior art compositions, preferred suspensions of the instant invention are designed not to increase repulsion between particles, but rather to decrease the attractive forces between particles. In this respect it should be appreciated that the principal forces driving flocculation in nonaqueous media are van der Waals attractive forces. As discussed above, VDW forces are quantum mechanical in origin, and can be visualized as attractions between fluctuating dipoles (i.e. induced dipole-induced dipole interactions). Dispersion forces are extremely short-range and scale as the sixth power of the distance between atoms. When two macroscopic bodies approach one another the dispersion attractions between the atoms sums up. The resulting force is of considerably longer range, and depends on the geometry of the interacting bodies.

More specifically, for two spherical particles, the magnitude of the VDW potential, $V_A$, can be approximated by $$V_A = \frac{-A_{\mathit{eff}}}{6H_0} \frac{R_1 R_2}{(R_1 + R_2)},$$

where $A_{\mathit{eff}}$ is the effective Hamaker constant which accounts for the nature of the particles and the medium, $H_0$ is the distance between particles, and $R_1$ and $R_2$ are the radii of spherical particles 1 and 2. The effective Hamaker constant is proportional to the difference in the polarizabilities of the dispersed particles and the suspension medium: $A_{\mathit{eff}} = (\sqrt{A_{SM}} - \sqrt{A_{PART}})^2$, where $A_{SM}$ and $A_{PART}$ are the Hamaker constants for the suspension medium and the particles, respectively. As the suspended particles and the dispersion medium become similar in nature, $A_{SM}$ and $A_{PART}$ become closer in magnitude, and $A_{\mathit{eff}}$ and $V_A$ become smaller. That is, by reducing the differences between the Hamaker constant associated with suspension medium and the Hamaker constant associated with the dispersed particles, the effective Hamaker constant (and corresponding van der Waals attractive forces) may be reduced.

One way to minimize the differences in the Hamaker constants is to create a "homodispersion", that is make both the continuous and dispersed phases essentially indistinguishable as discussed above. Besides exploiting the morphology of the particles to reduce the effective Hamaker constant, the components of the structural matrix (defining the perforated microstructures) will preferably be chosen so as to exhibit a Hamaker constant relatively close to that of the selected suspension medium. In this respect, one may use the actual values of the Hamaker constants of the suspension medium and the particulate components to determine the compatibility of the dispersion ingredients and provide a good indication as to the stability of the preparation. Alternatively, one could select relatively compatible particulate or perforated microstructure components and suspension mediums using characteristic physical values that coincide with measurable Hamaker constants but are more readily discernible.

In this respect, it has been found that the refractive index values of many compounds tend to scale with the corresponding Hamaker constant. Accordingly, easily measurable refractive index values may be used to provide a fairly good indication as to which combination of suspension medium and particle excipients will provide a dispersion having a relatively low effective Hamaker constant and associated stability. It will be appreciated that, since refractive indices of compounds are widely available or easily derived, the use of such values allows for the formation of stabilized dispersions in accordance with the present invention without undue experimentation. For the purpose of illustration only, the refractive indices of several compounds compatible with the disclosed dispersions are provided in Table I immediately below:

TABLE I

| Compound | Refractive Index |
| --- | --- |
| HFA-134a | 1.172 |
| HFA-227 | 1.223 |
| CFC-12 | 1.287 |
| CFC-114 | 1.288 |
| PFOB | 1.305 |
| Mannitol | 1.333 |
| Ethanol | 1.361 |
| n-octane | 1.397 |
| DMPC | 1.43 |
| Pluronic F-68 | 1.43 |
| Sucrose | 1.538 |
| Hydroxyethylstarch | 1.54 |
| Sodium chloride | 1.544 |

Consistent with the compatible dispersion components set forth above, those skilled in the art will appreciate that, the formation of dispersions wherein the components have a refractive index differential of less than about 0.5 is preferred. That is, the refractive index of the suspension medium will preferably be within about 0.5 of the refractive index associated with the particles or perforated microstructures. It will further be appreciated that, the refractive index of the suspension medium and the particles may be measured directly or approximated using the refractive indices of the major component in each respective phase. For the particulates or perforated microstructures, the major component may be determined on a weight percent basis. For the suspension medium, the major component will typically be derived on a volume percentage basis. In selected embodiments of the present invention the refractive index differential value will preferably be less than about 0.45, about 0.4, about 0.35 or even less than about 0.3. Given that lower refractive index differentials imply greater dispersion stability, particularly preferred embodiments comprise index differentials of less than about 0.28, about 0.25, about 0.2, about 0.15 or even less than about 0.1. It is submitted that a skilled artisan will be able to determine which excipients are particularly compatible without undue experimentation given the instant disclosure. The ultimate choice of preferred excipients will also be influenced by other factors, including biocompatibility, regulatory status, ease of manufacture, cost.

As discussed above, minimization of density differences between the particles and the continuous phase may be achieved by using perforated and/or hollow microstructures, such that the suspension medium constitutes most of the particle volume. As used herein, the term "particle volume" corresponds to the volume of suspension medium that would be displaced by incorporated hollow/porous particles if they were solid, i.e. the volume defined by the particle boundary. For the purposes of explanation, and as discussed above, these fluid filled particulate volumes may be referred to as "virtual particles." Preferably, the average volume of the bioactive agent/excipient shell or matrix (i.e. the volume of medium actually displaced by the perforated microstructure) comprises less than 80% of the average particle volume (or less than 80% of the virtual particle). More preferably, the volume of the microparticulate matrix comprises less than about 50%, 40%, 30% or even 20% of the average particle volume. Even more preferably, the average volume of the shell/matrix comprises less than about 10%, 5%, 3% or 1% of the average particle volume. Those skilled in the art will appreciate that such matrix or shell volumes typically contribute little to the virtual particle density which is overwhelmingly dictated by the suspension medium found therein.

It will further be appreciated that, the use of such microstructures will allow the apparent density of the virtual particles to approach that of the suspension medium substantially eliminating the attractive van der Waals forces. Moreover, as previously discussed, the components of the microparticulate matrix are preferably selected, as much as possible given other considerations, to approximate the density of suspension medium. Accordingly, in preferred embodiments of the present invention, the virtual particles and the suspension medium will have a density differential of less than about 0.6 g/cm$^3$. That is, the mean density of the virtual particles (as defined by the matrix boundary) will be within approximately 0.6 g/cm$^3$ of the suspension medium. More preferably, the mean density of the virtual particles will be within 0.5, 0.4, 0.3 or 0.2 g/cm$^3$ of the selected suspension medium. In even more preferable embodiments the density differential will be less than about 0.1, 0.05, 0.01, or even less than 0.005 g/cm$^3$.

In addition to the aforementioned advantages, the use of the disclosed particulates allows for the formation of dispersions comprising much higher volume fractions of particles in suspension. It should be appreciated that, the formulation of prior art dispersions at volume fractions approaching close-packing generally results in dramatic increases in dispersion viscoelastic behavior. Rheological behavior of this type is not appropriate for MDI or nebulizer applications. Those skilled in the art will appreciate that, the volume fraction of the particles may be defined as the ratio of the apparent volume of the particles (i.e. the particle volume) to the total volume of the system. Each system has a maximum volume fraction or packing fraction. For example, particles in a simple cubic arrangement reach a maximum packing fraction of 0.52 while those in a face centered cubic/hexagonal close packed configuration reach a maximum packing fraction of approximately 0.74. For non-spherical particles or polydisperse systems, the derived values are different. Accordingly, the maximum packing fraction is often considered to be an empirical parameter for a given system.

Here, it was surprisingly found that the preferred particulates of the present invention do not exhibit undesirable viscoelastic behavior even at high volume fractions, approaching close packing. To the contrary, they remain as free flowing, low viscosity suspensions having little or no yield stress when compared with analogous suspensions comprising solid particulates. The low viscosity of the disclosed suspensions is thought to be due, at least in large part, to the relatively low van der Waals attraction between the fluid-filled hollow, porous particles. As such, in selected embodiments the volume fraction of the disclosed dispersions is greater than approximately 0.3. Other embodiments may have packing values on the order of 0.3 to about 0.5 or on the order of 0.5 to about 0.8, with the higher values approaching a close packing condition. Moreover, as particle sedimentation tends to naturally decrease when the volume fraction approaches close packing, the formation of relatively concentrated dispersions may further increase formulation stability.

Although the methods and compositions of the present invention may be used to form relatively concentrated suspensions, the stabilizing factors work equally well at much lower packing volumes and such dispersions are contemplated as being within the scope of the instant disclosure. In this regard, it will be appreciated that, dispersions comprising low volume fractions are extremely difficult to stabilize using prior art techniques. Conversely, dispersions incorporating particulates comprising a bioactive agent as described herein are particularly stable even at low volume fractions. Accordingly, the present invention allows for stabilized dispersions, and particularly respiratory dispersions, to be formed and used at volume fractions less than 0.3. In some preferred embodiments, the volume fraction is approximately 0.0001–0.3, more preferably 0.001–0.01. Yet other preferred embodiments comprise stabilized suspensions having volume fractions from approximately 0.01 to approximately 0.1.

The perforated microstructures of the present invention may also be used to stabilize dilute suspensions of micronized bioactive agents. In such embodiments the perforated microstructures may be added to increase the volume fraction of particles in the suspension, thereby increasing suspension stability to creaming or sedimentation. Further, in these embodiments the incorporated microstructures may also act in preventing close approach (aggregation) of the micronized drug particles. It should be appreciated that, the perforated microstructures incorporated in such embodiments do not necessarily comprise a bioactive agent. Rather, they may be formed exclusively of various excipients, including surfactants.

Those skilled in the art will further appreciate that the stabilized suspensions or dispersions of the present invention may be prepared by dispersal of the microstructures in the selected suspension medium which may then be placed in a container or reservoir. In this regard, the stabilized preparations of the present invention can be made by simply combining the components in sufficient quantity to produce the final desired dispersion concentration. Although the microstructures readily disperse without mechanical energy, the application of mechanical energy to aid in dispersion (e.g. with the aid of sonication) is contemplated. Alternatively, the components may be mixed by simple shaking or other type of agitation. The process is preferably carried out under anhydrous conditions to obviate any adverse effects of moisture on suspension stability. Once formed, the dispersion has a reduced susceptibility to flocculation and sedimentation.

As indicated throughout the instant specification, the dispersions of the present invention are preferably stabilized. In a broad sense, the term "stabilized dispersion" will be held to mean any dispersion that resists aggregation, flocculation or creaming to the extent required to provide for the effective delivery of a bioactive agent. Moreover, it is a significant advantage of the instant invention that the disclosed dispersions and powders are stable at room temperature and do not require refrigeration or freezing to effectively maintain their activity. Besides prolonging shelf life, this remarkable temperature stability greatly simplifies shipping and administration.

While those skilled in the art will appreciate that there are several methods that may be used to assess the stability of a given dispersion, a preferred method for the purposes of the present invention comprises determination of creaming or sedimentation time using a dynamic photosedimentation method. A preferred method comprises subjecting suspended particles to a centrifugal force and measuring absorbance of the suspension as a function of time. A rapid decrease in the absorbance identifies a suspension with poor stability. It is submitted that those skilled in the art will be able to adapt the procedure to specific suspensions without undue experimentation.

For the purposes of the present invention the creaming time shall be defined as the time for the suspended drug particulates to cream to ½ the volume of the suspension medium. Similarly, the sedimentation time may be defined as the time it takes for the particulates to sediment in ½ the volume of the liquid medium. Besides the photosedimentation technique described above, a relatively simple way to determine the creaming time of a preparation is to provide the particulate suspension in a sealed glass vial. The vials are agitated or shaken to provide relatively homogeneous dispersions which are then set aside and observed using appropriate instrumentation or by visual inspection. The time necessary for the suspended particulates to cream to ½ the volume of the suspension medium (i.e., to rise to the top half of the suspension medium), or to sediment within ½ the volume (i.e., to settle in the bottom ½ of the medium), is then noted. Suspension formulations having a creaming time greater than 1 minute are preferred and indicate suitable stability. More preferably, the stabilized dispersions comprise creaming times of greater than 1, 2, 5, 10, 15, 20 or 30 minutes. In particularly preferred embodiments, the stabilized dispersions exhibit creaming times of greater than about 1, 1.5, 2, 2.5, or 3 hours. Substantially equivalent periods for sedimentation times are indicative of compatible dispersions.

It will also be understood that other components can be included in the stabilized dispersions of the present invention. For example, osmotic agents, stabilizers, chelators, buffers, viscosity modulators, salts, and sugars can be added to fine tune the stabilized dispersions for maximum life and ease of administration. Such components may be added directly to the suspension medium or associated with, or incorporated in, the perforated microstructures. Considerations such as sterility, isotonicity, and biocompatibility may govern the use of conventional additives to the disclosed compositions. The use of such agents will be understood to those of ordinary skill in the art and, the specific quantities, ratios, and types of agents can be determined empirically without undue experimentation.

F(iii). Metered Dose Inhalers

As discussed, the stabilized dispersions may preferably be administered to the nasal or pulmonary air passages of a patient via aerosolization, such as with a metered dose inhaler. The use of such stabilized preparations provides for superior dose reproducibility and improved deposition at the target site as described above. MDIs are well known in the art and could easily be employed for administration of the claimed dispersions without undue experimentation. Breath activated MDIs, as well as those comprising other types of improvements which have been, or will be, developed are also compatible with the stabilized dispersions and present invention and, as such, are contemplated as being with in the scope thereof.

MDI canisters generally comprise a container or reservoir capable of withstanding the vapor pressure of the propellant used such as, a plastic or plastic-coated glass bottle, or preferably, a metal can or, for example, an aluminum can which may optionally be anodized, lacquer-coated and/or plastic-coated, wherein the container is closed with a metering valve. The metering valves are designed to deliver a metered amount of the formulation per actuation. The valves incorporate a gasket to prevent leakage of propellant through the valve. The gasket may comprise any suitable elastomeric material such as, for example, low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DFIO, DF30, OF 31/50 ACT, DF60), Bespak plc, LTK (e.g. BK300, BK356) and 3M-Neotechnic Ltd., LIK (e.g. Spraymiser).

Each filled canister is conveniently fitted into a suitable channeling device or actuator prior to use to form a metered dose inhaler for administration of the medicament into the lungs or oral or nasal cavity of a patient. Suitable channeling devices comprise for example a valve actuator and a cylindrical or cone-like passage through which medicament may be delivered from the filled canister via the metering valve, to the nose or mouth of a patient e.g., a mouthpiece actuator. Metered dose inhalers are designed to deliver a fixed unit dosage of medicament per actuation such as, for example, in the range of 10 to 5000 micrograms of bioactive agent per actuation. Typically, a single charged canister will provide for tens or even hundreds of shots or doses.

With respect to MDIs, it is an advantage of the present invention that any biocompatible suspension medium having adequate vapor pressure to act as a propellant may be used. Particularly preferred suspension media are compatible with use in a metered dose inhaler. That is, they will be able to form aerosols upon the activation of the metering valve and associated release of pressure. In general, the selected suspension medium should be biocompatible (i.e. relatively non-toxic) and non-reactive with respect to the suspended perforated microstructures comprising the bioactive agent. Preferably, the suspension medium will not act as a substantial solvent for any components incorporated in the perforated microspheres. Selected embodiments of the invention comprise suspension media selected from the group consisting of fluorocarbons (including those substituted with other halogens), hydrofluoroalkanes, perfluorocarbons, hydrocarbons, alcohols, ethers or combinations thereof. It will be appreciated that, the suspension medium may comprise a mixture of various compounds selected to impart specific characteristics.

Particularly suitable propellants for use in the MDI suspension mediums of the present invention are those propellant gases that can be liquefied under pressure at room temperature and, upon inhalation or topical use, are safe, toxicologically innocuous and free of side effects. In this regard, compatible propellants may comprise any hydrocarbon, fluorocarbon, hydrogen-containing fluorocarbon or mixtures thereof having a sufficient vapor pressure to efficiently form aerosols upon activation of a metered dose inhaler. Those propellants, typically termed hydrofluoroalkanes or HFAs, are especially compatible. Suitable propellants include, for example, short chain hydrocarbons, $C_{1-4}$ hydrogen-containing chlorofluorocarbons such as $CH_2ClF$, $CCl_2F_2CHClF$, $CF_3CHClF$, $CHF_2CClF_2$, $CHClFCHF_2$, $CF_3CH_2Cl$, and $CClF_2CH_3$; $C_{1-4}$ hydrogen-containing fluorocarbons (e.g. HFAs) such as $CHF_2CHF_2$, $CF_3CH_2F$, $CHF_2CH_3$, and $CF_3CHFCF_3$; and perfluorocarbons such as $CF_3CF_3$ and $CF_3CF_2CF_3$. Preferably, a single perfluorocarbon or hydrogen-containing fluorocarbon is employed as the propellant. Particularly preferred as propellants are 1,1,1,2-tetrafluoroethane ($CF_3CH_2F$) (HFA-134a) and 1,1,1,2,3,3,3-heptafluoro-n-propane ($CF_3CHFCF_3$) (HFA-227), perfluoroethane, monochlorodifluoromethane, 1,1-difluoroethane, and combinations thereof. It is desirable that the formulations contain no components that deplete stratospheric ozone. In particular it is desirable that the formulations are substantially free of chlorofluorocarbons such as $CCl_3F$, $CCl_2F_2$, and $CF_3CCl_3$.

While preferred embodiments of the invention comprise ecologically benign suspension media, traditional chlorofluorocarbons and substituted fluorinated compounds may also be used as suspension mediums in accordance with the teachings herein. In this respect, FC-11 (CCL3F), FC-11B1 (CBrCl2F), FC-11B2 (CBr2ClF), FC12B2 (CF2Br2), FC21 (CHCl2F), FC21B1 (CHBrClF), FC-21B2 (CHBr2F), FC-31B1 (CH2BrF), FC113A (CCl3CF3), FC-122 (CClF2CHCl2), FC-123 (CF3CHCl2), FC-132 (CHClFCHClF), FC-133 (CHClFCHF2), FC-141 (CH2ClCHClF), FC-141B (CCl2FCH3), FC-142 (CHF2CH2Cl), FC-151 (CH2FCH2Cl), FC-152 (CH2FCH2F), FC-1112 (CClF=CClF), FC-1121 (CHCl=CFCl) and FC-1131 (CHCl=CHF) are all compatible with the teachings herein despite possible attendant environmental concerns. As such, each of these compounds may be used, alone or in combination with other compounds (i.e. less volatile fluorocarbons) to form stabilized respiratory dispersions in accordance with the present invention.

F(iv). Nebulizers

Along with the aforementioned embodiments, the stabilized dispersions of the present invention may also be used in conjunction with nebulizers to provide an aerosolized medicament that may be administered to the pulmonary air passages of a patient in need thereof. Nebulizers are well known in the art and could easily be employed for administration of the claimed dispersions without undue experimentation. Breath activated nebulizers, as well as those comprising other types of improvements which have been, or will be, developed are also compatible with the stabilized dispersions and present invention and are contemplated as being with in the scope thereof.

Nebulizers work by forming aerosols, that is converting a bulk liquid into small droplets suspended in a breathable gas. Here, the aerosolized medicament to be administered (preferably to the pulmonary air passages) will comprise small droplets of suspension medium associated with perforated microstructures comprising a bioactive agent. In such embodiments, the stabilized dispersions of the present invention will typically be placed in a fluid reservoir operably associated with a nebulizer. The specific volumes of preparation provided, means of filling the reservoir, etc., will largely be dependent on the selection of the individual nebulizer and is well within the purview of the skilled artisan. Of course, the present invention is entirely compatible with single-dose nebulizers and multiple dose nebulizers.

The present invention overcomes these and other difficulties by providing stabilized dispersions with a suspension medium that preferably comprises a fluorinated compound (i.e. a fluorochemical, fluorocarbon or perfluorocarbon). Particularly preferred embodiments of the present invention comprise fluorochemicals that are liquid at room temperature. As indicated above, the use of such compounds, whether as a continuous phase or, as a suspension medium, provides several advantages over prior art liquid inhalation preparations. In this regard, it is well established that many fluorochemicals have a proven history of safety and biocompatibility in the lung. Further, in contrast to aqueous solutions, fluorochemicals do not negatively impact gas exchange following pulmonary administration. To the contrary, they may actually be able to improve gas exchange and, due to their unique wettability characteristics, are able to carry an aerosolized stream of particles deeper into the lung, thereby improving systemic delivery of the desired pharmaceutical compound. In addition, the relatively non-reactive nature of fluorochemicals acts to retard any degradation (by proteolysis or hydrolysis) of an incorporated bioactive agent.

In any event, nebulizer mediated aerosolization typically requires an input of energy in order to produce the increased surface area of the droplets and, in some cases, to provide transportation of the atomized or aerosolized medicament. One common mode of aerosolization is forcing a stream of fluid to be ejected from a nozzle, whereby droplets are formed. With respect to nebulized administration, additional energy is usually imparted to provide droplets that will be sufficiently small to be transported deep into the lungs. Thus, additional energy is needed, such as that provided by a high velocity gas stream or a piezoelectric crystal. Two popular types of nebulizers, jet nebulizers and ultrasonic nebulizers, rely on the aforementioned methods of applying additional energy to the fluid during atomization.

In terms of pulmonary delivery of bioactive agents to the systemic circulation via nebulization, recent research has focused on the use of portable hand-held ultrasonic nebulizers, also referred to as metered solutions. These devices, generally known as single-bolus nebulizers, aerosolize a single bolus of medication in an aqueous solution with a particle size efficient for deep lung delivery in one or two breaths. These devices fall into three broad categories. The first category comprises pure piezoelectric single-bolus nebulizers such as those described by Mütterlein, et. al., (J. Aerosol Med. 1988; 1:231). In another category, the desired aerosol cloud may be generated by microchannel extrusion single-bolus nebulizers such as those described in U.S. Pat. No. 3,812,854. Finally, a third category comprises devices exemplified by Robertson, et. al., (WO 92/11050) which describes cyclic pressurization single-bolus nebulizers. Each of the aforementioned references is incorporated herein in their entirety. Most devices are manually actuated, but some devices exist which are breath actuated. Breath actuated devices work by releasing aerosol when the device senses the patient inhaling through a circuit. Breath actuated nebulizers may also be placed in-line on a ventilator circuit to release aerosol into the air flow which comprises the inspiration gases for a patient.

Regardless of which type of nebulizer is employed, it is an advantage of the present invention that biocompatible nonaqueous compounds may be used as suspension mediums. Preferably, they will be able to form aerosols upon the application of energy thereto. In general, the selected suspension medium should be biocompatible (i.e. relatively non-toxic) and non-reactive with respect to the suspended perforated microstructures comprising the bioactive agent. Preferred embodiments comprise suspension media selected from the group consisting of fluorochemicals, fluorocarbons (including those substituted with other halogens), perfluorocarbons, fluorocarbon/hydrocarbon diblocks, hydrocarbons, alcohols, ethers, or combinations thereof. It will be appreciated that, the suspension medium may comprise a mixture of various compounds selected to impart specific characteristics.

In accordance with the teachings herein, the suspension media may comprise any one of a number of different compounds including hydrocarbons, fluorocarbons or hydrocarbon/fluorocarbon diblocks. In general, the contemplated hydrocarbons or highly fluorinated or perfluorinated compounds may be linear, branched or cyclic, saturated or unsaturated compounds. Conventional structural derivatives of these fluorochemicals and hydrocarbons are also contemplated as being within the scope of the present invention as well. Selected embodiments comprising these totally or partially fluorinated compounds may contain one or more hetero-atoms and/or atoms of bromine or chlorine. Preferably, these fluorochemicals comprise from 2 to 16 carbon atoms and include, but are not limited to, linear, cyclic or polycyclic perfluoroalkanes, bis(perfluoroalkyl) alkenes, perfluoroethers, perfluoroamines, perfluoroalkyl bromides and perfluoroalkyl chlorides such as dichlorooctane. Particularly preferred fluorinated compounds for use in the suspension medium may comprise perfluorooctyl bromide $C_8F_{17}Br$ (PFOB or perflubron), dichlorofluorooctane $C_8F_{16}Cl_2$, and the hydrofluoroalkane perfluorooctyl ethane $C_8F_{17}C_2H_5$ (PFOE). With respect to other embodiments, the use of perfluorohexane or perfluoropentane as the suspension medium is especially preferred.

More generally, exemplary fluorochemicals which are contemplated for use in the present invention generally include halogenated fluorochemicals (i.e. $C_nF_{2n+1}X$, $XC_nF_{2n}X$, where n=2–10, X=Br, Cl or I) and, in particular, 1-bromo-F-butane n-$C_4F_9Br$, 1-bromo-F-hexane (n-$C_6F_{13}Br$), 1-bromo-F-heptane (n-$C_7F_{15}Br$), 1,4-dibromo-F-butane and 1,6-dibromo-F-hexane. Other useful brominated fluorochemicals are disclosed in U.S. Pat. No. 3,975,512 to Long and are incorporated herein by reference. Specific fluorochemicals having chloride substituents, such as perfluorooctyl chloride (n-$C_8F_{17}Cl$), 1,8-dichloro-F-octane (n-$ClC_8F_{16}Cl$), 1,6-dichloro-F-hexane (n-$ClC_6F_{12}Cl$), and 1,4-dichloro-F-butane (n-$ClC_4F_8Cl$) are also preferred.

Fluorocarbons, fluorocarbon-hydrocarbon compounds and halogenated fluorochemicals containing other linkage groups, such as esters, thioethers and amines are also suitable for use as suspension media in the present invention. For instance, compounds having the general formula, $C_nF_{2n+1}OC_mF_{2m+1}$, or $C_nF_{2n+1}CH=CHC_mF_{2m+1}$, (as for example $C_4F_9CH=CHC_4F_9$ (F-44E), i-$C_3F_9CH=CHC_6F_{13}$ (F-i36E), and $C_6F_{13}CH=CHC_6F_{13}$ (F-66E)) where n and m are the same or different and n and m are integers from about 2 to about 12 are compatible with teachings herein. Useful fluorochemical-hydrocarbon diblock and triblock compounds include those with the general formulas $C_nF_{2n+1}$—$C_mH_{2m+1}$ and $C_nF_{2n+1}C_mH_{2m+1}$, where n=2–12; m=2–16 or $C_pH_{2p+1}$—$C_nF_{2n}$—$C_mH_{2m+1}$, where p=1–12, m=1–12 and n=2–12. Preferred compounds of this type include $C_8F_{17}C_2H_5$, $C_6F_{13}C_{10}H_{21}$, $C_8F_{17}C_8H_{17}$, $C_6F_{13}CH=CHC_6H_{13}$ and $C_8F_{17}CH=CHC_{10}H_{21}$. Substituted ethers or polyethers (i.e. $XC_nF_{2n}OC_mF_{2m}X$, $XCFOC_nF_{2n}OCF_2X$, where n and m=1–4, X=Br, Cl or I) and fluorochemical-hydrocarbon ether diblocks or triblocks (i.e. $C_nF_{2n+1}$—O—$C_mH_{2m+1}$, where n=2–10; m=2–16 or $C_pH_{2p+1}$—O—$C_nF_{2n}$—O—$C_mH_{2m+1}$, where p=2–12, m=1–12 and n=2–12) may also used as well as $C_nF_{2n+1}O$—$C_mF_{2m}OC_pH_{2p+1}$, wherein n, m and p are from 1–12. Furthermore, depending on the application, perfluoroalkylated ethers or polyethers may be compatible with the claimed dispersions.

Polycyclic and cyclic fluorochemicals, such as $C_{10}F_{18}$ (F-decalin or perfluorodecalin), perfluoroperhydrophenanthrene, perfluorotetramethylcyclohexane (AP-144) and perfluoro n-butyldecalin are also within the scope of the invention. Additional useful fluorochemicals include perfluorinated amines, such as F-tripropylamine ("FTPA") and F-tributylamine ("FTBA"). F4-methyloctahydroquinolizine ("FMOQ"), F-N-methyl-decahydroisoquinoline ("FMIQ"), F-N-methyldecahydroquinoline ("FHQ"), F-N-cyclohexylpyrrolidine ("FCHP") and F-2-butyltetrahydrofuran ("FC-75" or "FC-77"). Still other useful fluorinated compounds include perfluorophenanthrene, perfluoromethyldecalin, perfluorodimethylethylcyclohexane, perfluorodimethyldecalin, perfluorodiethyldecalin, perfluoromethyladamantane, perfluorodimethyladamantane. Other contemplated fluorochemicals having nonfluorine substituents, such as, perfluorooctyl hydride, and similar compounds having different numbers of carbon atoms are also useful. Those skilled in the art will further appreciate that other variously modified fluorochemicals are encompassed within the broad definition of fluorochemical as used in the instant application and suitable for use in the present invention. As such, each of the foregoing compounds may be used, alone or in combination with other compounds to form the stabilized dispersions of the present invention.

Additional exemplarly fluorocarbons, or classes of fluorinated compounds, that may be useful as suspension media include, but are not limited to, fluoroheptane, fluorocycloheptane fluoromethylcycloheptane, fluorohexane, fluorocyclohexane, fluoropentane, fluorocyclopentane, fluoromethylcyclopentane, fluorodimethylcyclopentanes, fluoromethylcyclobutane, fluorodimethylcyclobutane, fluorotrimethylcyclobutane, fluorobutane, fluorocyclobutane, fluoropropane, fluoroethers, fluoropolyethers and fluorotriethylamines. Such compounds are generally environmentally sound and are biologically non-reactive.

While any liquid capable of producing an aerosol upon the application of energy may be used in conjunction with a nebulizer, the selected suspension medium will preferably have a vapor pressure less than about 5 atmospheres and more preferably less than about 2 atmospheres. Unless otherwise specified, all vapor pressures recited herein are measured at 25° C. In other embodiments, preferred suspension media compounds will have vapor pressures on the order of about 5 torr to about 760 torr, with more preferable compounds having vapor pressures on the order of from about 8 torr to about 600 torr, while still more preferable compounds will have vapor pressures on the order of from about 10 torr to about 350 torr. Such suspension media may be used in conjunction with compressed air nebulizers, ultrasonic nebulizers or with mechanical atomizers to provide effective ventilation therapy. Moreover, more volatile compounds may be mixed with lower vapor pressure components to provide suspension media having specified physical characteristics selected to further improve stability or enhance the bioavailability of the dispersed bioactive agent.

Other embodiments of the present invention directed to nebulizers will comprise suspension media that boil at selected temperatures under ambient conditions (i.e. 1 atm). For example, preferred embodiments will comprise suspension media compounds that boil above 0° C., above 5° C., above 10° C., above 15°, or above 20° C. In other embodiments, the suspension media compound may boil at or above 25° C. or at or above 30° C. In yet other embodiments, the selected suspension media compound may boil at or above human body temperature (i.e. 37° C.), above 45° C., 55° C., 65° C., 75° C., 85° C. or above 100° C.

F(v). Direct Administration

Along with MDIs and nebulizers, it will be appreciated that the stabilized dispersions of the present invention may be used to administer bioactive agents to a variety of target sites using various routes of administration. For example, the disclosed compositions may be delivered directly to the lungs in conjunction with liquid dose instillation (LDI) techniques. Alternatively, the stabilized dispersions could be effectively delivered to mucosal surfaces in the nasal passages using a nasal pump, spray bottle or atomizer. In yet other embodiments, the disclosed dispersions could be administered to a target site (e.g. intramuscularly or intradermally) using conventional injections or through the use of needleless injectors employing compressed gases. The latter are particularly preferred in the case of needleless inoculation. Still other embodiments are directed to the topical delivery of the dispersions to target sites such as the eye or the ear or, more preferably, mucosal surfaces such as those in the urogenital tract or the gastrointestinal tract. Such techniques may further employ ionophoresis to enhance penetration of the incorporated bioactive agent. In any event, the stabilized dispersions provide for excellent dose reproducibility while preserving the activity of the incorporated agent.

Those skilled in the art will appreciate that suspension media compatible with the aforementioned delivery techniques are similar to those set forth above for use in conjunction with nebulizers. That is, the stabilized dispersions will preferably comprise suspension media selected from the group consisting of fluorochemicals, fluorocarbons (including those substituted with other halogens), perfluorocarbons, fluorocarbon/hydrocarbon diblocks, hydrocarbons, alcohols, ethers, or combinations thereof. More particularly, for the purposes of the present application, compatible suspension media for such delivery techniques shall be equivalent to those enumerated above in conjunction with use in nebulizers. In particularly preferred embodiments the selected suspension medium shall comprise a fluorochemical that is liquid under ambient conditions.

It should be further be appreciated that liquid dose instillation involves the direct administration of a stabilized dispersion to the lung. In this regard, direct pulmonary administration of bioactive compounds is particularly effective in the treatment of disorders especially where poor vascular circulation of diseased portions of a lung reduces the effectiveness of intravenous drug delivery. With respect to LDI the stabilized dispersions are preferably used in conjunction with partial liquid ventilation or total liquid ventilation. Moreover, the present invention may further comprise introducing a therapeutically beneficial amount of a physiologically acceptable gas (such as nitric oxide or oxygen) into the pharmaceutical microdispersion prior to, during or following administration.

For LDI, the dispersions of the present invention may be administered to the lung using a pulmonary delivery conduit. Those skilled in the art will appreciate the term "pulmonary delivery conduit", as used herein, shall be construed in a broad sense to comprise any device or apparatus, or component thereof, that provides for the instillation or administration of a liquid in the lungs. In this respect a pulmonary delivery conduit or delivery conduit shall be held to mean any bore, lumen, catheter, tube, conduit, syringe, actuator, mouthpiece, endotracheal tube or bronchoscope that provides for the administration or instillation of the disclosed dispersions to at least a portion of the pulmonary air passages of a patient in need thereof. It will be appreciated that the delivery conduit may or may not be associated with a liquid ventilator or gas ventilator. In particularly preferred embodiments the delivery conduit will comprise an endotracheal tube or bronchoscope.

While the stabilized dispersions may be administered up to the functional residual capacity of the lungs of a patient, it will be appreciated that selected embodiments will comprise the pulmonary administration of much smaller volumes (e.g. on the order of a milliliter or less). For example, depending on the disorder to be treated, the volume administered may be on the order of 1, 3, 5, 10, 20, 50, 100, 200 or 500 milliliters. In preferred embodiments the liquid volume is less than 0.25 or 0.5 percent FRC. For particularly preferred embodiments, the liquid volume is 0.1 percent FRC or less. With respect to the administration of relatively low volumes of stabilized dispersions it will be appreciated that the wettability and spreading characteristics of the suspension media (particularly fluorochemicals) will facilitate the even distribution of the bioactive agent in the lung. However, in other embodiments it may be preferable to administer the suspensions a volumes of greater than 0.5, 0.75 or 0.9 percent FRC. Of course the extraordinary wetting and spreading characteristics associated with at least some fluorochemicals makes them particularly compatible for administration to other mucosal surfaces such as the nasal passages.

With regard to the powders and stabilized dispersions disclosed herein those skilled in the art will appreciate that they may be advantageously supplied to the physician or other health care professional, in a sterile, prepackaged or kit form. More particularly, the formulations may be supplied as stable powders or preformed dispersions ready for administration to the patient. Conversely, they may be provided as separate, ready to mix components. When provided in a ready to use form, the powders or dispersions may be packaged in single use containers or reservoirs, as well as in multi-use containers or reservoirs. In either case, the container or reservoir may be associated with the selected inhalation or administration device and used as described herein. When provided as individual components (e.g., as powdered microspheres and as neat suspension medium) the stabilized preparations may then be formed at any time prior to use by simply combining the contents of the containers as directed. Additionally, such kits may contain a number of ready to mix, or prepackaged dosing units so that the user can then administer them as needed.

G. EXAMPLES

The foregoing description will be more fully understood with reference to the following Examples. Such Examples, are, however, merely representative of preferred methods of practicing the present invention and should not be read or interpreted as limiting the scope of the invention in any manner.

I

Preparation of Hollow Porous Particles of HA Peptide by Spray-Drying

Hollow porous HA 110–120 peptide (amino acid residues 110–120 of the hemagglutinin of the influenza virus) particles (PulmoSpheres™) were prepared by a spray drying technique with a B-191 Mini Spray-Drier (Büchi, Flawil, Switzerland) under the following conditions: aspiration: 100%, inlet temperature: 85° C.; outlet temperature: 51° C.; feed pump: 10%; $N_2$ flow: 800 L/hr. The feed was prepared by mixing two preparations, A and B, immediately prior to spray drying. A 150 mesh stainless steel screen was placed in the cyclone exit port to aid with the collection particles.

Preparation A: 5 g of deionized water was used to dissolve 18 mg of HA 110–120 peptide (Chiron Corp., Emeryville, Calif.) and 1 mg of hydroxyethyl starch (Ajinomoto, Japan).

Preparation B: A fluorocarbon-in-water emulsion stabilized by phospholipid was prepared in the following way. The phospholipid, 0.3 g EPC-100-3 (Lipoid KG, Ludwigshafen, Germany), was homogenized in 33 g of hot deionized water (T=50 to 60° C.) using an Ultra-Turrax mixer (model T-25) at 8000 rpm for 2 to 5 minutes (T=60–70° C.). Eight grams of Perflubron (perfluorooctyl bromide: Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for passes.

One eighth of preparation B was separated and added to preparation A. The resulting HA peptide/perflubron emulsion feed solution was fed into the spray dryer under the conditions described above. The powder collected in the cyclone, and sieving screen was washed into the collection jar using perflubron. The HA suspension in perflubron was subsequently frozen at −60° C. and lyophilized. A free flowing white powder was obtained.

II

In Vitro Activity of Hollow Porous Particles Containing HA Peptide

The functionality of HA peptide in PulmoSpheres (HA-Pul) to activate antigen presenting cells was compared with neat HA peptide. HA peptide PulmoSpheres from Example I were incubated with sterile PBS at a concentration of 5 mg/ml (weight of formulation/volume). Serial dilutions of the resultant HA-Pul-PBS solution were added to microwells containing M12 antigen presenting cells ($1 \times 10^4$/well) and HA specific TcH ($2 \times 10^4$/well) in complete RPMI-10% FCS. The TcH cell line bears a reporter gene controlled by IL-2 promoter (IL-2/-gal).

After 12 hours incubation at 37° C., the microwell plate was centrifuged, cells were fixed with paraformaldehyde-glutaraldehyde for 5 minutes at 4° C., washed with PBS and X-gal substrate was added overnight. The number of activated TcH per 500 cells per well were counted using light microscopy. The total number of activated TcH per well was estimated by multiplying the total number of cells with the percentage of blue cells. The results, shown in FIG. 1, demonstrate the presence of active peptide in the formulation. Comparison with a standard activation curve (HA saline) showed that the concentration of active peptide was approximately 50% (wt/wt), which was in agreement with reverse phase-HPLC measurements.

III

HA Peptide PulmoSpheres Mechanism of Action

The requirement for internalization and processing of PulmoSphere microparticles containing T cell epitope HA 110–120 (HA-Pul) was examined. HA-Pul suspended in perflubron (500 nM/well HA 110–120 peptide) were air-dried and incubated with non-fixed or paraformaldehyde fixed M12 antigen presenting cells (APC) cells in the presence of specific TcH cells in complete RPMI-10% FCS, and compared with HA-Pul suspended in PBS and neat HA peptide at similar concentrations. Sucrose-purified A/PR/8/34 (H1N1) virus (15 g/ml) was used as the positive control, since it does that require intracellular processing. Negative controls comprised a formulation of NP 147–155 peptide, non-formulated NP peptide and an irrelevant virus. The number of cells and culture conditions described in Example II were followed. The cells were fixed and exposed to an X-gal substrate. The results were expressed as % of activated TcH.

Figure 2:
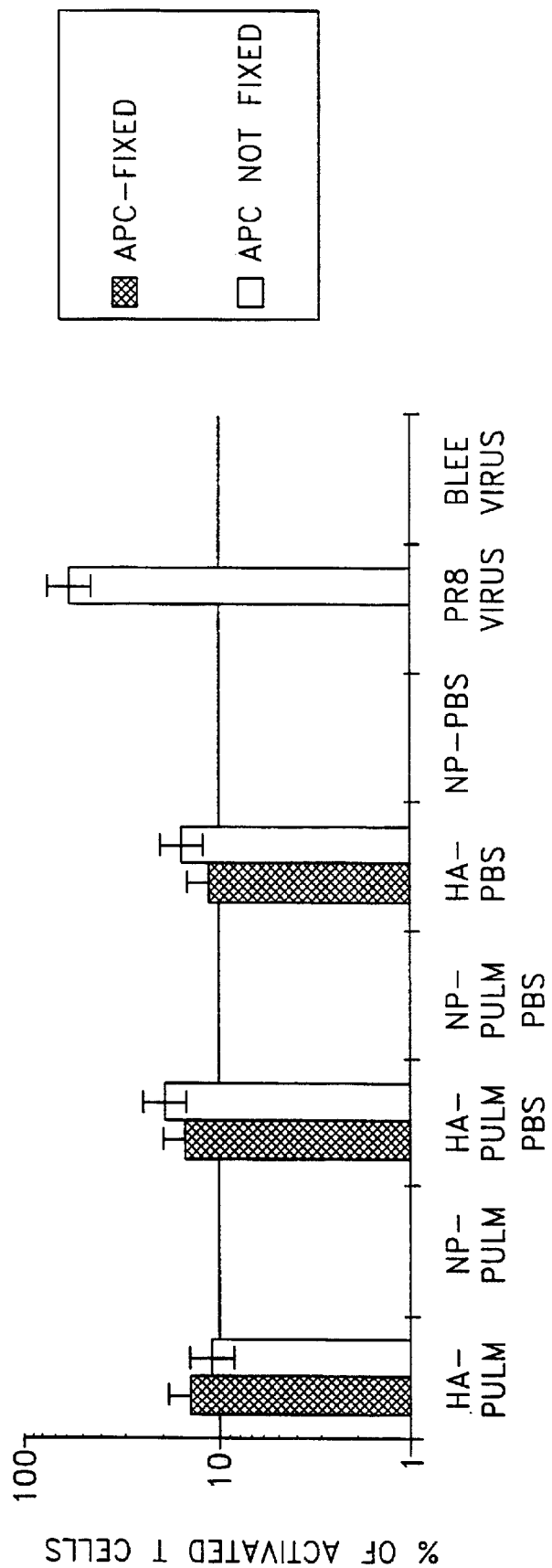
FIG. 2 illustrates the fact that antigens formulated in microstructures do not require intracellular processing to activate T cells.

FIG. 2 shows that both fixed and non-fixed APC were able to present neat HA peptide and HA-Pul. In contrast, only live APC were able to present HA peptide from the viral context. Furthermore, formulated or neat NP peptide as well as B/Lee virus did not activate the specific TcH. The results indicate that internalization and processing of HA-Pul is not a prerequisite for the activation of TcH. Rather, the HA-peptide is readily released from the PulmoSpheres and binds to MHC class II molecules (I-$E^d$) on M12 APC, resulting in the engagement of TCR and activation of TcH. This processing step was observed for neat HA peptide as well as HA-Pul delivered in PBS or perflubron. Moreover, these results demonstrate that HA 110–120 peptide formulated in PulmoSpheres and stabilized in perflubron retains its immunogenicity.

IV

Preparation of Fluorescent-Labeled Hollow Porous HA Peptide Particles by Spray-Drying Hollow porous HA-fluoroscein 110–120 peptide/Texas Red DHPE particles were prepared by a spray drying technique with a B-191 Mini Spray-Drier (Büchi, Flawil, Switzerland) under the following conditions: aspiration: 100%, inlet temperature: 85° C.; outlet temperature: 51° C.; feed pump: 10%; $N_2$ flow: 800 L/hr. The feed was prepared by mixing two solutions A and B immediately prior to spray drying. A 150 mesh stainless steel screen was placed in the cyclone exit port to aid with the collection particles.

Preparation A: 5 g of deionized water was used to dissolve 20 mg of HA-fluoroscein 110–120 peptide (Chiron Corp., Emeryville, Calif.) and 1 mg of hydroxyethyl starch (Ajinomoto, Japan).

Preparation B: A fluorocarbon-in-water emulsion stabilized by phospholipid was prepared in the following way. The phospholipid, 0.3 g EPC-100-3 (Lipoid KG, Ludwigshafen, Germany), and 0.3 mg fluorescent dye, Texas Red DHPE, (Molecular Probes, Eugene, Oreg., 3 mg) were first dissolved in chloroform. The chloroform was then removed using a Buchi RotoVap. The E100-3/Texas Red DHPE thin film was then dispersed into 33 ml hot deionized water (60 to 70° C.). The surfactants were then further processed in the aqueous phase using an Ultra-Turrax mixer (model T-25) at 10,000 rpm for approximately 2 minutes (T=50 to 60 C). 8 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

One eighth of preparation B was separated and added to preparation A. The resulting HA-fluoroscein peptide/Texas Red DHPE/Perflubron emulsion feed solution was fed into the spray dryer under the conditions described above. The powder collected in the cyclone, and sieving screen was washed into the collection jar using Perflubron. The HA suspension in Perflubron was subsequently frozen at −60° C. and lyophilized. A free flowing fluorescent fuschsia-colored powder was obtained.

V

Bioavailability of Fluorescent-Labeled HA PulmoSpheres

A formulation comprising fluoroscein-HA peptide (20% wt/wt) PulmoSpheres (f-HA-Pul) prepared as in Example IV was suspended in perflubron. Metofane anesthetized mice were inoculated intranasally (i.n.) with a 70 l volume of f-HA-Pul in perflubron, corresponding to 70 g of peptide dose. Blood samples were collected by ocular bleeding in heparin-treated tubes, the plasma was separated and the concentration of the peptide was measured by fluorometry. As a control, an intravenous i.v.) inoculation of 70 g of f-HA peptide in 70 l of sterile saline (n=4 for all groups) was used.

Figure 3:
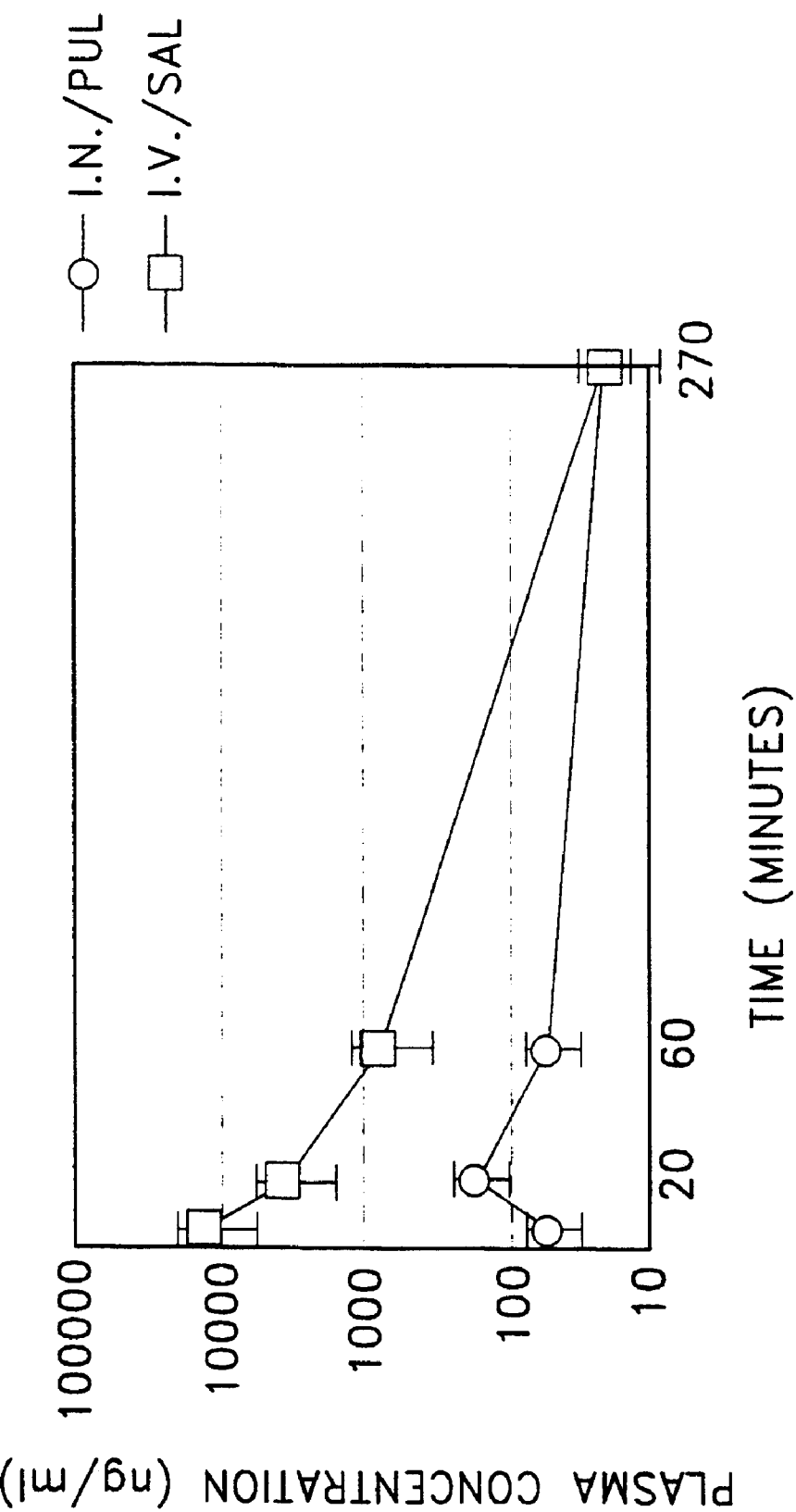
FIG. 3 graphically compares the plasma concentration of HA peptide delivered using nasally administered microparticulates and intravenous injection.

FIG. 3 depicts the serum concentration of f-HA peptide over time. The absolute bioavailability for the i.n. delivered f-HA peptide was approximately 5%, with $T_{max}$ occurring at 20 minutes. The pharmacokinetic profile differed between the two routes of administration, with a continuous logarithmic decay for the i.v. administration and a transient increase followed by an exponential decay in the case of i.n. administration. Elimination of f-HA occurs via urine (not shown), with total clearance by 6 hours.

This Example shows that i.n. administration of T cell epitopes (having a molecular weight of approximately 1.4 kDa) formulated in Pul is compatible with systemic delivery.

VI

Preparation of Hollow Porous Particles of Human IgG by Spray-Drying

Hollow porous Human IgG particles were prepared by a spray drying technique with a B-191 Mini Spray-Drier (Büchi, Flawil, Switzerland) under the following conditions: aspiration: 100%, inlet temperature: 85° C.; outlet temperature: 61° C.; feed pump: 10%; $N_2$ flow: 800 L/hr. The feed was prepared by mixing two solutions A and B immediately prior to spray drying.

Preparation A: 2 g of normal saline (Baxter, Chicago, Ill.) was used to dissolve 55 mg of human IgG (Sigma Chemicals. St. Louis, Mo.) and 3.2 mg of hydroxyethyl starch (Ajinomoto, Japan).

Preparation B: A fluorocarbon-in-water emulsion stabilized by phospholipid was prepared in the following way. The phospholipid, 0.415 g EPC-100-3 (Lipoid KG, Ludwigshafen, Germany), was homogenized in 40.3 g of hot deionized water (T=50 to 60° C.) using an Ultra-Turrax mixer (model T-25) at 8000 rpm for 2 to 5 minutes (T=60–70° C.). 5.2 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

One eighth of preparation B by volume was separated and added to preparation A. The resulting IgG/perflubron emulsion feed solution was fed into the spray dryer under the conditions described above. The powder collected in the cyclone, and sieving screen was washed into the collection jar using perflubron. The IgG suspension in perflubron was subsequently frozen at −60° C. and lyophilized. A free flowing white powder was obtained. The hollow porous IgG particles had a volume-weighted mean aerodynamic diameter of 2.373±1.88 μm as determined by a time-of-flight analytical method (Aerosizer, Amherst Process Instruments, Amherst, Mass.).

VII

In Vitro Activity of Polyclonal Human IgG PulmoSpheres

A formulation of polyclonal human IgG PulmoSpheres (hIgG-Pul) from Example VI was characterized for activity using a capture hIgG ELISA. A 5 mg/mL hIgG-Pul suspension in perflubron was prepared, pipetted into the wells and air dried. PBS was added to the dried hIgG-Pul and allowed to incubate overnight. The hydrated hIgG-Pul solution was diluted and transferred to an ELISA plate coated with mouse anti-human k chain monoclonal antibody in coating buffer (dil. 1:1000, Sigma Immunochemical), and subsequently blocked with PBS containing 15% goat serum for 2 hours at room temperature. The wells were washed and the assay was developed using goat anti-human IgG alkaline phosphatase conjugate (1:1000 in PBS-15% goat serum 0.05% Tween), followed by addition of pNPP substrate. The optical density (OD) was read using at an automatic plate reader set at –405 nm. hIgG in saline (standard) and hIgG mixed with blank PulmoSpheres were employed as controls to rule out an effect of the lipid on the assay. The blank PulmoSpheres were comprised of only phospholipid and starch.

Figure 4:
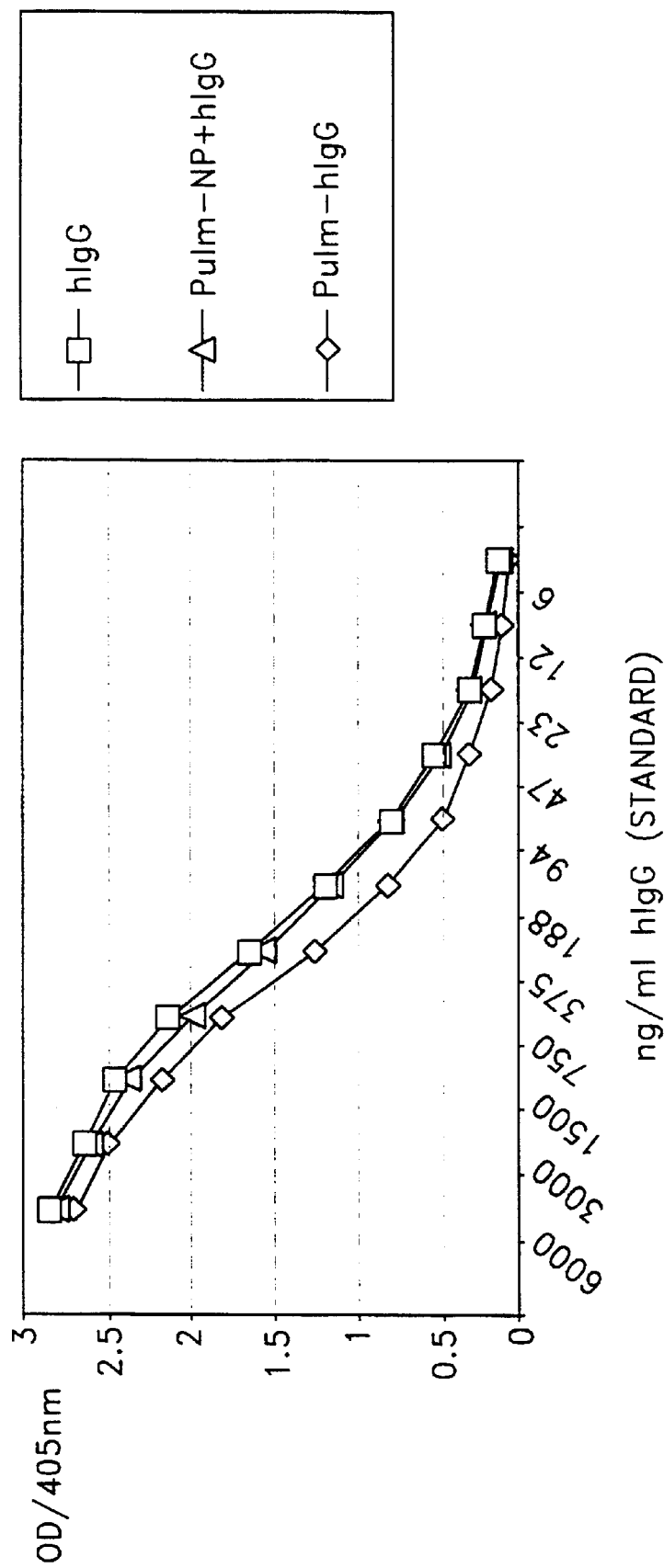
FIG. 4 depicts calibration curves for human IgG formulated in microparticulates as described in the instant application along with selected controls.
Figure 6A:
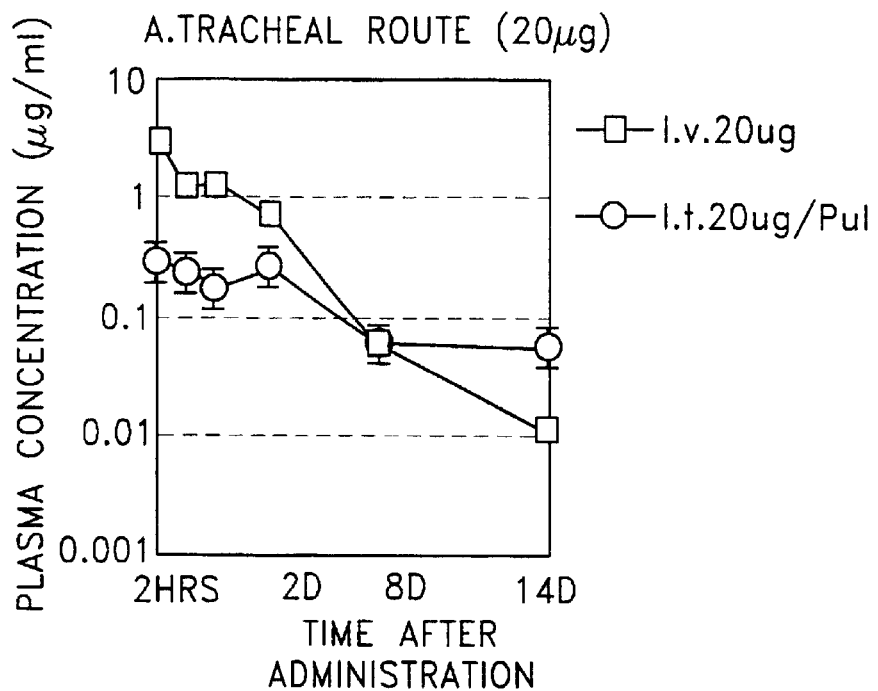
FIGS. 6A and 6B show the persistence of IgG in the plasma following intratracheal and nasal administration using formulated microparticulates.
Figure 6B:
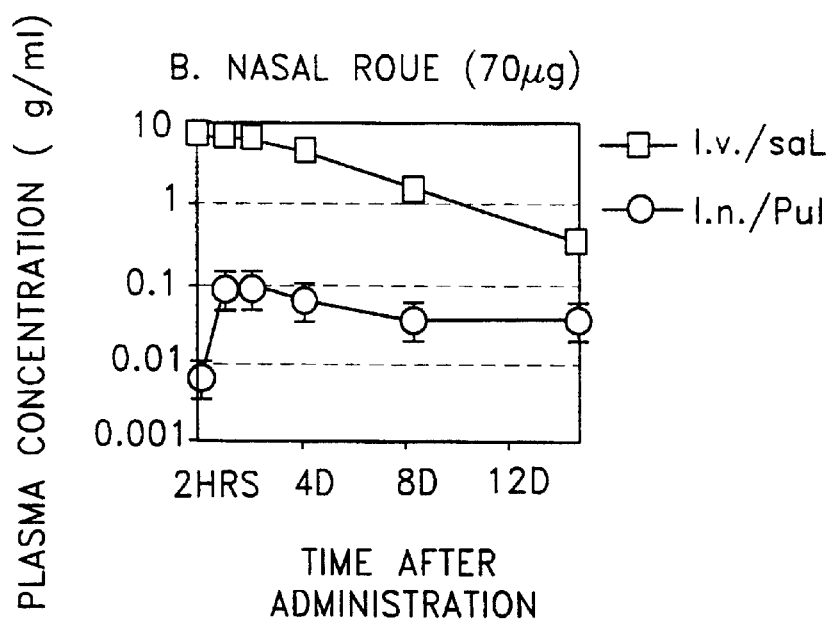

FIG. 4 depicts the calibration curves for the hIgG-Pul, hIgG and hIgG +blank PulmoSpheres. The hIgG-Pul formulation was determined to comprise approximately 20% hIgG by weight. In addition, the hIgG-Pul retained the expression of k light chain and heavy chain epitopes.

VIII

Dissolution Kinetics of HA 110–120 Peptide and Human IqG From PulmoSphere Formulations The kinetics of antigen and hIgG release from PulmoSpheres was measured using dissolution chambers equipped with 0.2 $\mu$m diameter filters, and adapted in 24-well flat bottom cell culture plates. Approximately 3 mg of PulmoSphere powder from Examples I and VI were placed in the lower compartment of the dissolution chamber and exposed simultaneously to sterile PBS (1.3 ml/well). The plates were placed on a horizontal shaker (30 RPM) at 37° C., to simulate the breathing pattern. 25 $\mu$l samples were collected from the upper compartment and analyzed by capture ELISA in the case of hIgG (FIG. 5A) or bioassay in the case of fluoroscein-labeled HA peptide formulation (f-HA) (FIG. 5B). The results for f-HA were independently confirmed by fluorometry (not shown). The dissolution kinetics of the hIgG and HA peptide PulmoSphere formulations were compared with their respective aqueous controls.

The results depicted in FIGS. 5A and 5B and were expressed as percent release. A rapid diffusion-controlled release was observed for HA peptide formulation, with no difference between the aqueous control. Complete dissolution occurred within 2 hours. In contrast, a slower erosion-controlled kinetics was observed for the hIgG formulation. Complete dissolution required more than 6 hours as compared with 1 hour for the aqueous IgG control. The results described herein demonstrate that the dissolution kinetics from PulmoSpheres depends, at least in part, on the molecular weight of the formulated compound (1.4 kDa and 150 kDa, respectively). It will also be appreciated that differences in hydrophilicity or hydrophobicity may have similar effects.

IX

Bioavailability of hIgG PulmoSpheres

Human IgG PulmoSpheres (hIgG-Pul) from Example VI were administered either intratracheally (20 g hIgG in 20 l of perflubron) to mice anesthetized with ketamine/xylazine, or via the nasal route (70 g hIgG in 70 $\mu$l of perflubron) to mice anesthetized with metofane. An identical volume of hIgG in sterile PBS was administered intravenously in the control group. The mice were bled at various time intervals and the serum concentration of hIgG was assessed by capture ELISA in all groups (n=3). Absolute bioavailability was determined from the areas under the serum concentration-time curve (AUC) as compared with the i.v. control. AUC values were calculated using the trapezoid rule.

The plamsa hIgG concentration curves are depicted in FIGS. 6A (i.t.), and 6B (i.n.). The absolute bioavailability for the intratracheal delivery of hIgG-Pul was 27%, and 1.5% for intranasal inoculation. In both cases, the $T_{max}$ occurred at approximately 2 days. Western blotting showed that the molecular weight for the circulating hIgG after delivery via the respiratory tract was indistinguishable from the neat material. The hIgG was observed to persist in the circulation more than 14 days.

X

Antibody Response to hIgG PulmoSpheres Delivered via the Tracheal Route

The humoral response in the blood and bronchoalveolar lavage (BAL) in mice treated with hIgG-PulmoSpheres (hIgG-Pul) from Example VI suspended in perflubron via intratracheal administration (20 g dose of hIgG). Mice were also treated with the following controls: 20 $\mu$g hIgG in saline i.t., 100 $\mu$g hIgG in saline i.v. and i.t., 100 $\mu$l g in complete Freund's Adjuvant (CFA) subcutaneous and saline it. Each group was done in triplicate. Blood and BAL were collected 2 weeks after immunization.

The titer of anti-hIgG mouse IgG was measured using ELISA plates coated with hIgG or with 0.1% BSA. The wells were blocked with PBS-15% goat serum and incubated for two hours using various dilutions of sera or BAL. After washing, the assay was developed with goat anti-mouse IgG alkaline phosphatase conjugate, followed by the addition of pNPP substrate. The optical density (OD) of the plates were analyzed at 550 nm using an automatic plate reader and the results were expressed as endpoint dilution titers in the case of serum IgG (FIG. 7A) or mean OD for BAL IgG (FIG. 7B).

The results show an increased systemic and local humoral responses in mice treated with hIgG-Pul via the intratracheal route, as compared with the dose/route matched group that received hIgG in saline. Moreover, the response was enhanced as compared with mice that received higher doses of hIgG in saline, via intratracheal or intravenous routes. The titer of serum antibodies was similar to that measured in mice immunized s.c. with hIgG in CFA. Interestingly, the humoral response did not correlate with the systemic bioavailability (data not shown), implying the participation of local immunity.

XI

T Cell Response to hIgG PulmoSpheres Delivered via Tracheal Route

The level of T cell immunity induced in the spleens of mice immunized with hIgG-PulmoSpheres (hIgG-Pul) from Example VI suspended in perflubron by the tracheal route. The spleens were dissociated into single cell suspensions that were treated with hypotonic buffer to remove the red blood cells. The splenocytes were resuspended in complete RPMI-10% FCS at $4 \times 10^6$ cells/ml and incubated in 24-well flat bottom plates (1 ml/well), in the presence of 6 g/ml of hIgG. After 72 hours incubation, the supernatants were collected and the concentration of IL2, IFN- and IL-4 determined by ELISA (Biosource International, Camarillo, Calif.).

Figure 8:
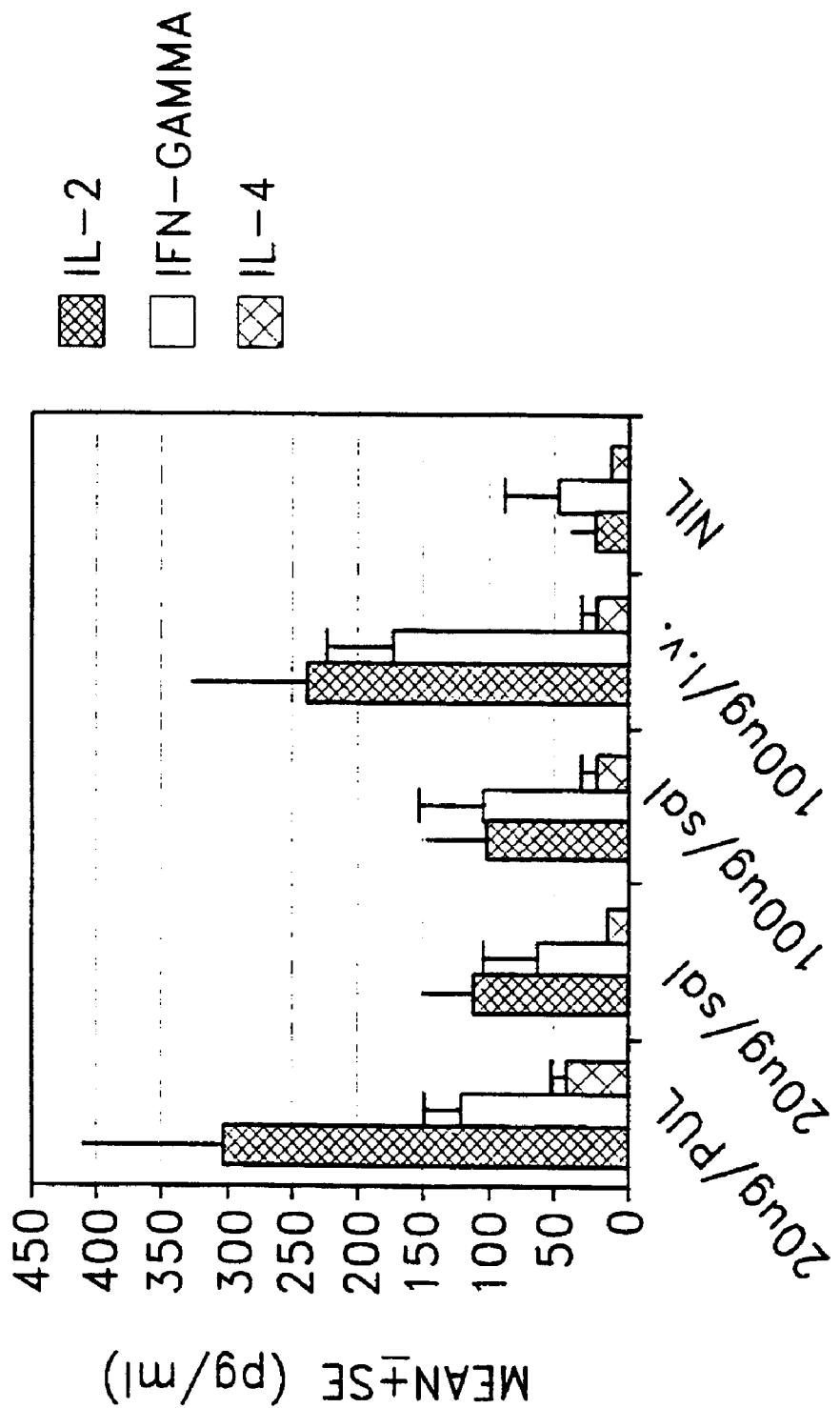
FIG. 8 graphically illustrates levels of cytokines indicative of a T cell response following intratracheal administration of IgG microparticulates to mice.

The results (FIG. 8) were expressed as mean values of cytokine concentration among individual mice in each group, and showed enhanced production of all three cytokines in mice immunized with hIgG-Pul as compared with the hIgG saline controls. The production of cytokines by splenic T cells for the hIgG-Pul treated group was comparable with that observed for the i.v. hIgG in saline group. These results strongly suggest systemic migration of memory T cells primed in the lung.

XII

Antibody Response to hIgG PulmoSpheres Delivered Via the Nasal Route

Figure 9:
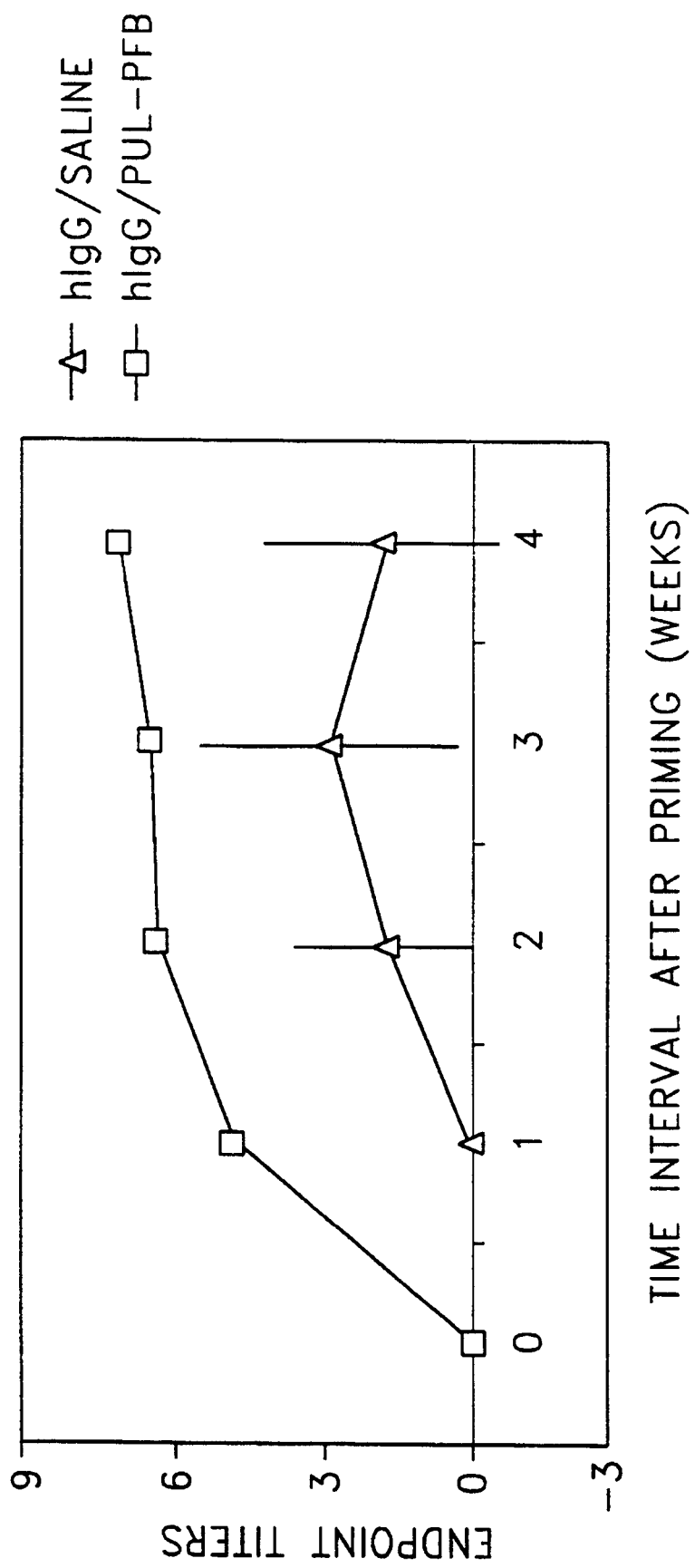
FIG. 9 depicts murine antibody response to IgG microparticulates administered intranasally.

The humoral response of mice that received hIgG via intranasal instillation (20 g) either formulated as PulmoSpheres (hIgG-Pul) from Example VI suspended in perflubron or dissolved in saline was characterized. Sera was obtained at various time intervals after immunization and the titer of specific mouse IgG raised against the hIgG was measured using the ELISA procedure described at Example X. The results (FIG. 9) were expressed as mean endpoint titers (n=3), and showed that the kinetics of onset was faster, the magnitude was higher and the intersubject reproducibility of immune responses was lower in mice treated with hIgG-Pul as compared to saline.

XIII

Antibody Response to hIgG PulmoSpheres Delivered Via Peritoneal Route

The humoral response of mice treated with hIgG-Pulmospheres (hIgG-Pul) from Example VI suspended in perflubron via the peritoneal (i.p.) route (100 g dose of hIgG). Mice were also treated i.p. with 100 μg hIgG in the following controls: in saline, in a multilamellar dipalmitoylphospahtidylcholine (DPPC) liposome saline solution (+ml lip), in a unilamellar DPPC liposome saline solution (+ul lip) and in a blank PulmoSphere saline solution (+empty Pul). An additional control group of blank PulmoSphere solution devoid of hIgG was also tested. The particle median diameter of ml lip (>10 μm) and ul lip (90 nm) were determined using a laser light scattering technique. Each group was done in triplicate. The IgG humoral immune response in sera, at 7 and 14 days was measured using the same ELISA technique described in Example X.

Figure 10A:
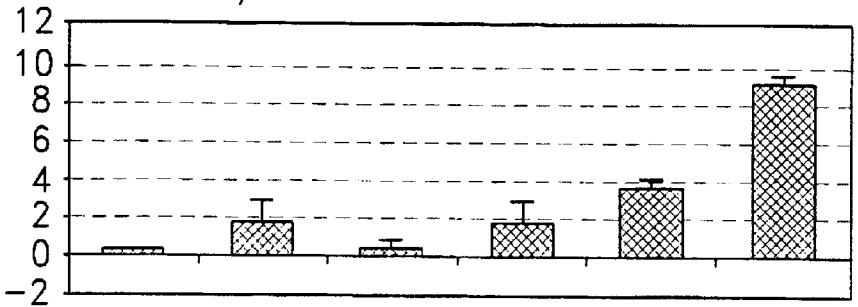
FIGS. 10A and 10B present murine antibody titers at 7 and 14 days respectively following intraperitoneal administration of IgG microparticulates.
Figure 10B:
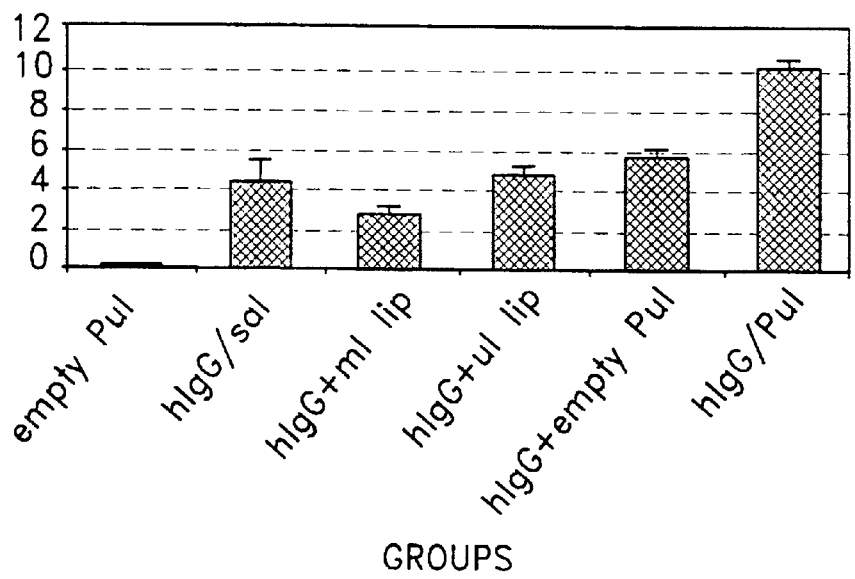

The results were expressed as means of endpoint titers and showed a consistent increase in antibody titers for animals that were inoculated with hIgG-Pul. More particularly FIGS. 10A and 10B show endpoint titers at 7 and 14 days respectively. hIgG added to empty Pul induced titers similar to hIgG in saline. Furthermore, addition of either DPPC liposome preparation to hIgG did not restore the increased immunity observed with hIgG-Pul. Thus, these results demonstrate that an: (1) enhanced immunity hIgG-Pul is not a route dependent phenomenon (see Examples X and XII); (2) formulation of hIgG-Pul is a prerequisite for the enhanced immunogenicity of hIgG; and (3) DPPC or other components of Pul do not have an independent adjuvant effect. Moreover, these results elucidate the importance of the route of delivery as well as other factors responsible for the enhanced immunity elicited by hIgG-Pul.

XIV

Preparation of Hollow Porous Particles of Influenza Virus A/WSN/32 (H1N1) by Spray-Drying Hollow porous Influenza Virus (A/WSN/32 H1N1), which comprises a relatively complex enveloped virus comprising 8 structural protein complexes and 8 negatively charged RNA segments, were successfully incorporated in microparticles prepared by a spray drying technique with a B-191 Mini Spray-Drier (Büchi, Flawil, Switzerland) under the following conditions: aspiration: 100%, inlet temperature: 85° C.; outlet temperature: 61° C.; feed pump: 10%; $N_2$ flow: 800 L/hr. The feed was prepared by mixing two preparations A and B immediately prior to spray drying. Prior to formulation, the virus was live and had been purified by sucrose-gradient centrifugation.

Preparation A: Weighed 1 mg hydroxyethyl starch (Ajinomoto, Japan) and transferred to tube containing 0.6 mg Influenza Virus in saline.

Preparation B: A fluorocarbon-in-water emulsion stabilized by phospholipid was prepared in the following way. The phospholipid, 0.111 g EPC-100-3 (Lipoid KG, Ludwigshafen, Germany), was homogenized in 20 g of hot deionized water (T=50 to 60° C.) using an Ultra-Turrax mixer (model T-25) at 8000 rpm for 2 to 5 minutes (T=60–70° C.). 4.4 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

One eighth of preparation B by volume was separated and added to preparation A. The resulting Influenza Virus/perflubron emulsion feed solution was fed into the spray dryer under the conditions described above. The powder collected in the cyclone, and the sieving screen was washed into the collection jar using perflubron. The Influenza Virus suspension in perflubron was subsequently frozen at −60° C. and lyophilized. A free flowing white powder was obtained.

XV

In Vitro Activity of Influenza Virus A/WSN/32 (H1N1) PulmoSpheres

The incorporation of live viral antigen into spray-dried particles was characterized using the following technique: Influenza Virus A/WSN/32 (H1N1) PulmoSpheres (WSN-Pul) from Example XIV were dissolved in sterile PBS at a concentration of 5 mg/ml for 6 hours at 40° C. The hydrated WSN-Pul was then incubated at various dilutions with non-fixed or paraformaldehyde-fixed M12 antigen presenting cells (APC) for 1 hour at 37° C., in 96-well plates. After antigen pulsing, the APCs were washed and incubated for four hours with TcH. The formaldehyde-glutaraldehyde fixed cells were incubated with X-gal substrate, and positive cells were counted.

Figures 11A, 11B, 11C:
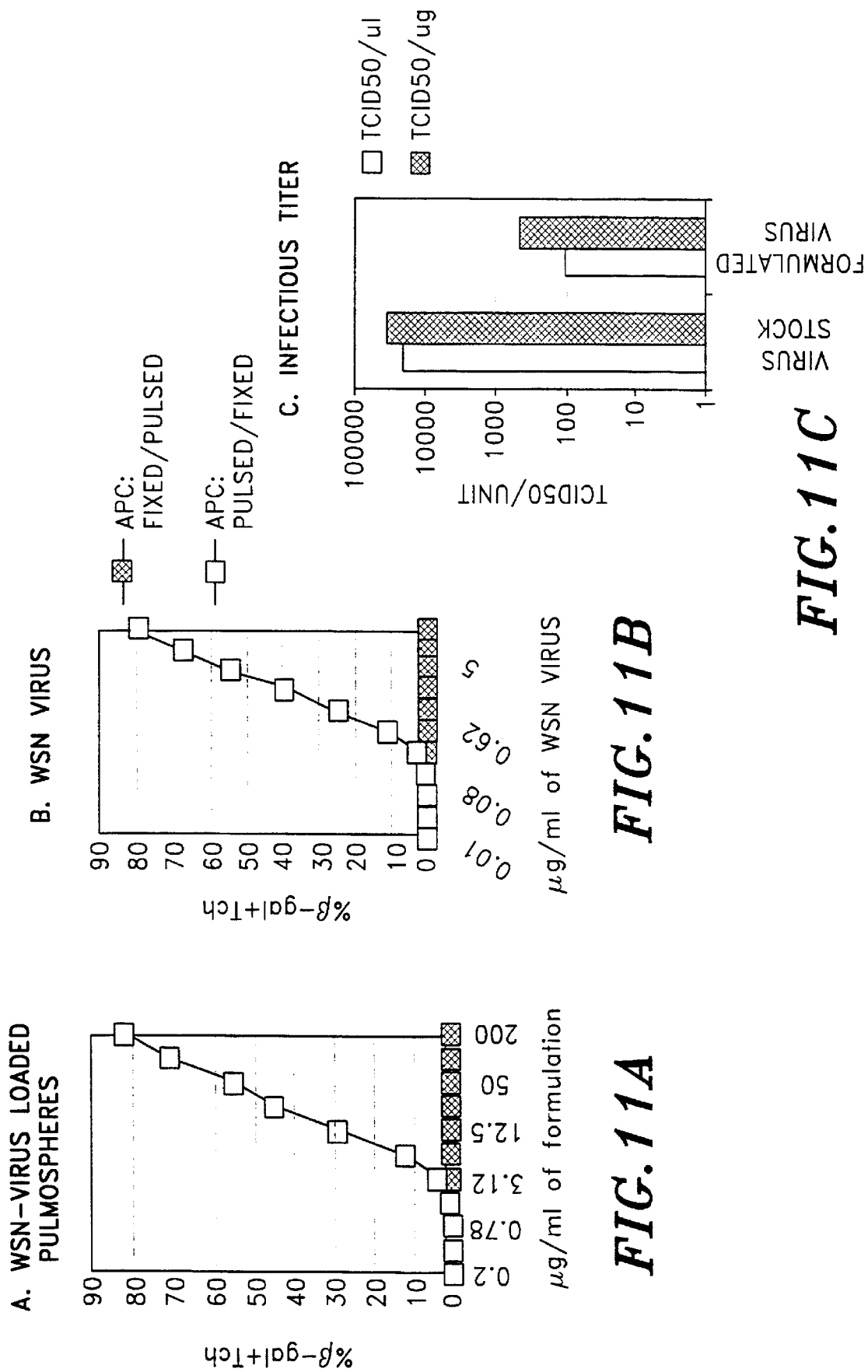
FIGS. 11A, 11B and 11C respectively illustrate T cell responses to microparticulate formulated virus, viral control and infectious titer of both formulated and unformulated virus.

Results were expressed as percent activated TcH (FIG. 11A). Various concentrations of sucrose-purified live WSN virus were used as controls (FIG. 11B). The WSN-Pul formulation was determined to contain approximately 5% influenza virus by weight. Only the unfixed APC's could activate the virus, indicating that the antigens had not degraded. Titration of infectious virus was determined by MDCK (Madine Darby kidney carcinoma cells) assay (FIG. 11C), and showed that approximately 1% of the total virus was still able to infect and replicate in the permissive cells. Together, these results demonstrate successful incorporation of relatively large influenza virus antigens in PulmoSphere powders.

XVI

Antibody Response to Influenza Virus A/WSN/32 (H1N1) PulmoSpheres Delivered Via Nasal Route The induction of virus-specific IgG antibody response against WSN virus after intranasal inoculation of BALB/c mice with an Influenza Virus A/WSN/32 (H1N1) Pulmo-Sphere (WSN-Pul) formulation containing 5 g of virus and $2 \times 10^3$ TCID$_{50}$ of live virus (1% of the total antigen load corresponding to the amount of live virus) was measured. Control mice were immunized mice with $2 \times 10^3$ TCID$_{50}$ live virus (corresponding to 0.05 g of total virus) or UV-killed WSN virus (5 g). Sera from mice treated with hIgG was used as negative control. The antibody response was measured in sera using the following ELISA technique: wells were coated with sucrose purified WSN virus in coating buffer, blocked with non-mammalian proteins (SeraBlock) and incubated with serial dilutions of serum samples. The samples were washed, and the assay was developed with biotin conjugated rat anti-mouse mAb followed by strptavidin-alkaline phosphatase and pNPP substrate. The results were expressed as geometrical means of reciprocal endpoint titers. The number of mice per inoculation group was three.

Figure 12:
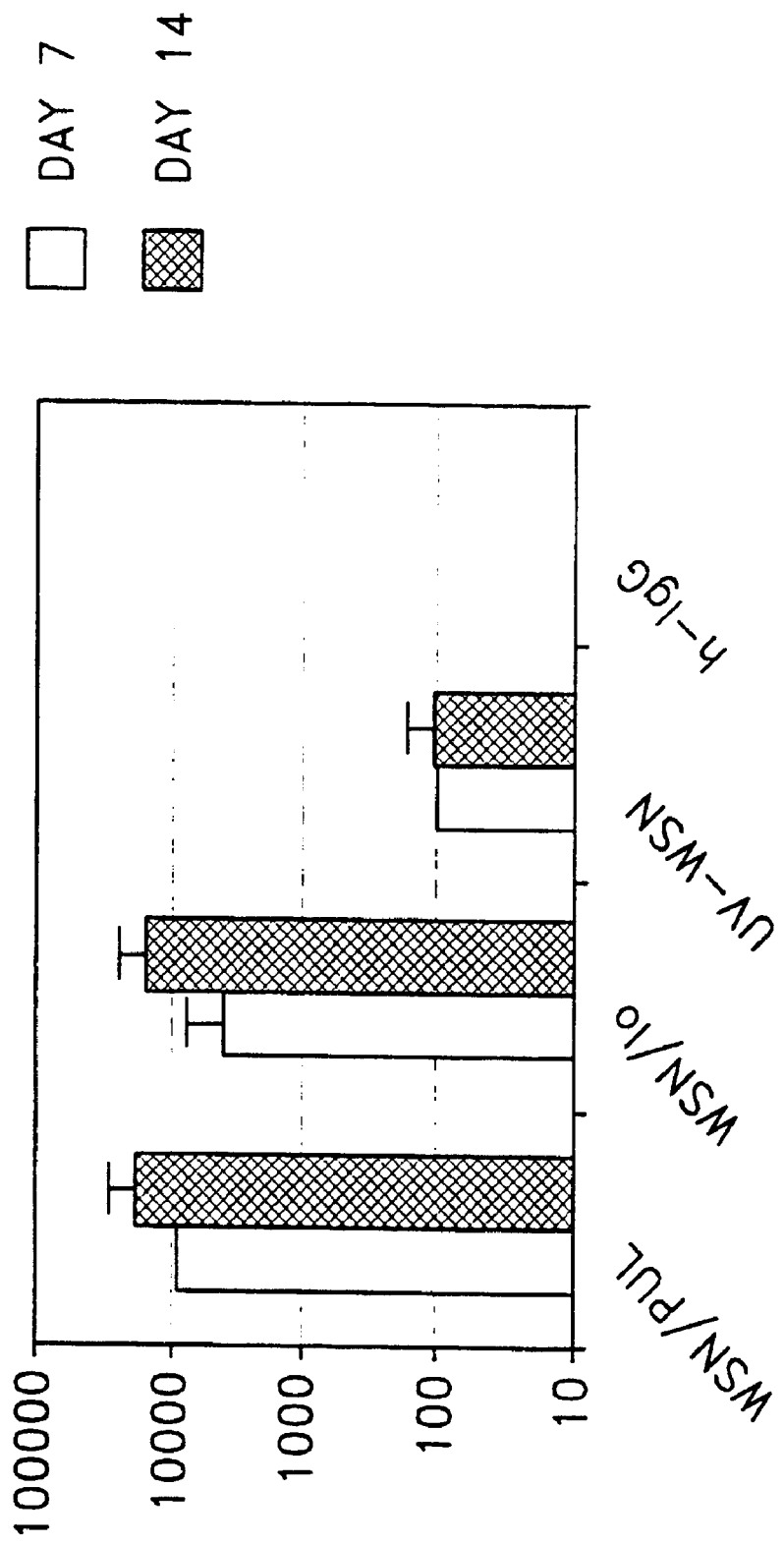
FIG. 12 depicts murine antibody responses to microparticulate formulated live and killed influenza virus at 7 and 14 days following intranasal administration.

The results depicted in FIG. 12 show the induction of high titers of IgG antibodies in mice immunized with WSN-Pul or live WSN virus in saline (WSN/lo) at 7 and 14 days. In contrast, only small titers of specific IgG were detected in mice immunized with killed virus in saline.

XVII

T Cell Response to Influenza Virus A/WSN/32 (H1N1) PulmoSpheres Delivered Via Nasal Route The T cell response was defined in terms of virus and epitope-specific cytokine production of lymphocytes from mice immunized as described above (Example XVI). The induction of T-cell response after intranasal inoculation of BALB/c mice with a Influenza Virus A/WSN/32 (H1N1) PulmoSpheres (WSN-Pul) formulation containing 5 g of virus and $2 \times 10^3$ TCID$_{50}$ of live virus (1% of the total antigen load corresponding to the amount of live virus) was measured. Control mice were immunized mice with $2 \times 10^3$ TCID$_{50}$ live virus (corresponding to 0.05 g of total virus) or UV-killed WSN virus (5 g). The antigens examined were sucrose-purified WSN virus, HA 110–120 peptide and NP 147–155 peptide. An untreated saline group was included as control.

Peripheral blood mononuclear cells (PBMC) were isolated from blood at day 10 after immunization, by Ficoll gradient centrifugation. Various numbers of responder cells were incubated in nitrocellulose/anti-IFN or anti-IL-4 (PharMingen) ELISPOT plates (Millipore) at $3 \times 10^5$ cells/well in complete RPMI-10% FCS. Stimulator cells (mytomicin treated splenocytes, $5 \times 10^5$/well), antigens and human rIL-2 (20 U/ml) were added and the plates were co-incubated for 48 hours. The cells were then washed with PBS-0.05% Tween, anti-cytokine antibodies (PharMingen) were incubated overnight and the assay was developed using HRP-streptavidin conjugate followed by insoluble substrate (Vector Laboratories). The assay was stopped with water, the wells were air-dried and the spots were counted using a stereomicroscope.

Figure 13A:
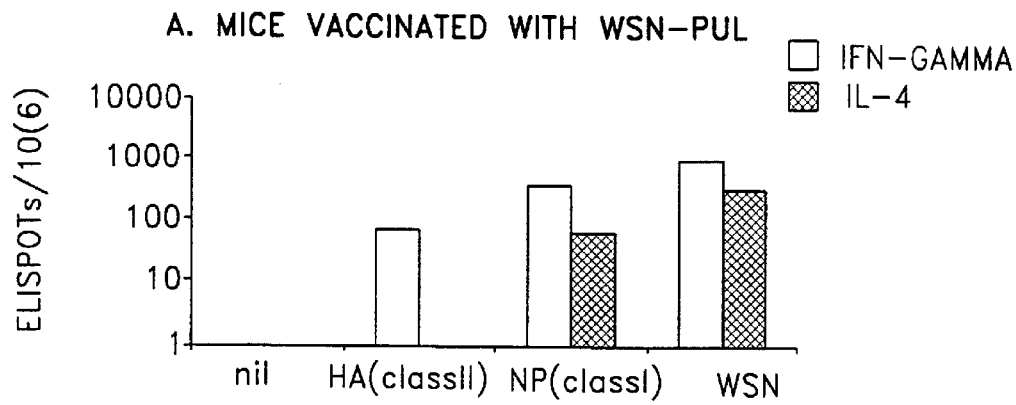
FIGS. 13A, 13B and 13C show, respectively, murine levels of factors indicative of a T cell response following intranasal inoculation of viral microparticulates or live virus or killed virus along with control antigens.
Figure 13B:
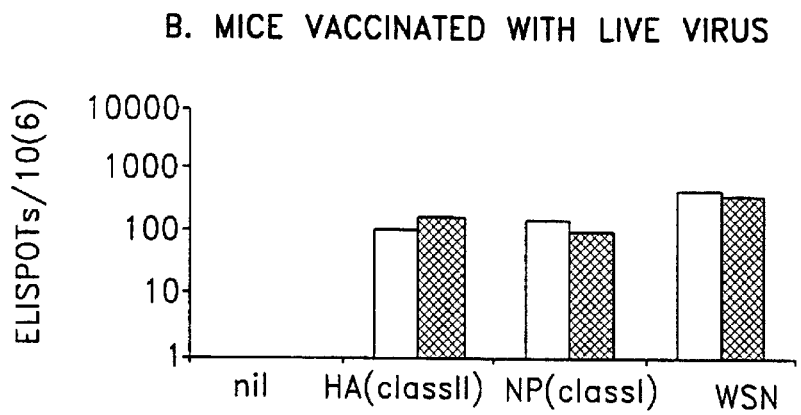
Figure 13C:
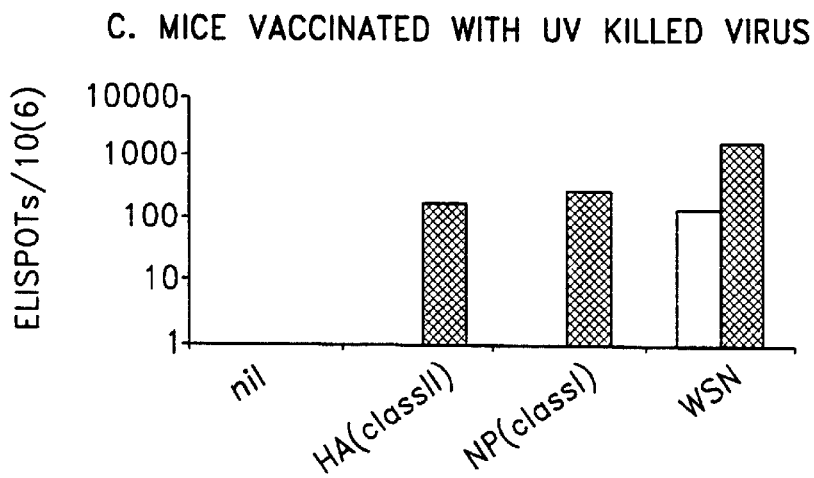

The results were expressed as the frequency of specific cells that produce IFN- or IL-4/$10^6$ PBMC, after subtracting the background signal. The background was reproducibly below $6/10^6$. PBMC were pooled from the mice in each group. The results in FIGS. 13A, 13B and 13C show that vaccination with WSN-Pul and WSN virus generally induced HA-, NP- and WSN-specific T cells producing IFN- and IL-4. In contrast, immunization with killed virus induced predominantly IL-4 producing T cells. Moreover, the immunization with killed virus induced an enhanced subpopulation of IL-4 producing Tc2 cells, specific for the NP 147–155 peptide. These data indicate that the T cell response provoked by the live control and formulated virus (i.e. comprising live and killed virus) was more effective the response provoked by the killed virus control corresponding to typical conventional vaccines.

XVIII

Figure 14A:
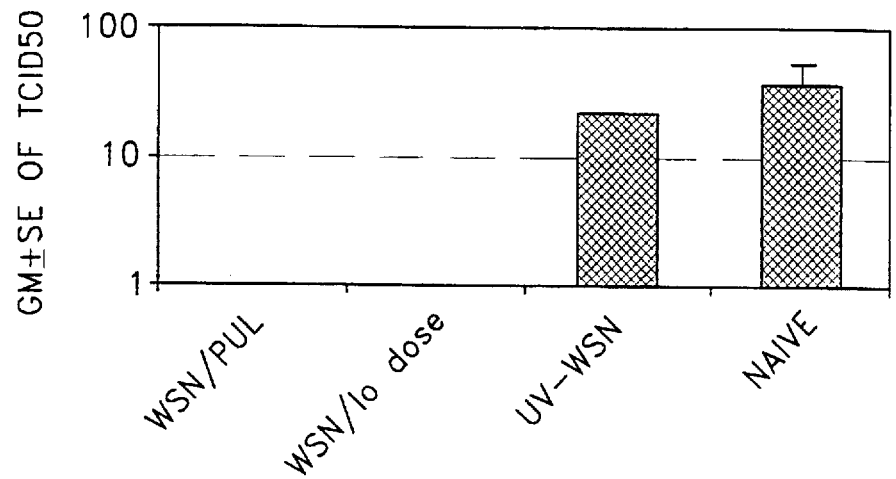
FIGS. 14A and 14B respectively illustrate viral shedding and body weight variation in mice intranasally inoculated with microparticulates comprising both live and killed virus.
Figure 14B:
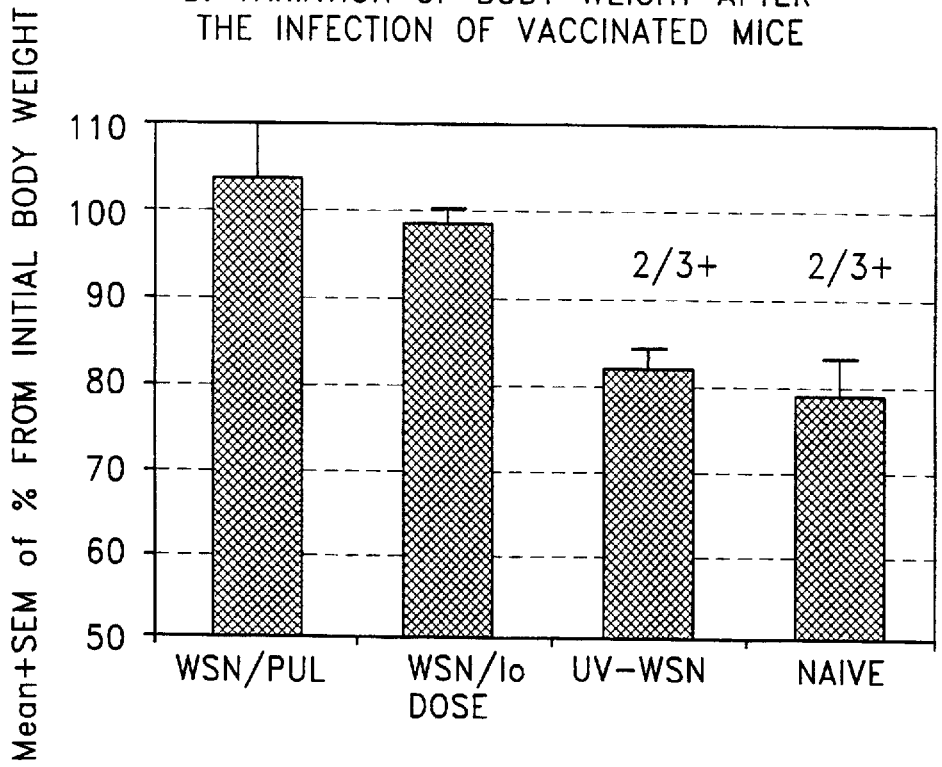

Protection Against Infectious Challenge of Mice Immunized With Influenza Virus A/WSN/32 (H1N1) PulmoSpheres Delivered Via Nasal Route Mice immunized as described in Example XVII were challenged at three weeks after immunization with $1.2 \times 10^6$ influenza virus delivered via the nasal route. The protection in terms of virus shedding and variation of body weight were defined at day 4 after the challenge. The results are shown in FIGS. 14A and 14B.

Measurement of virus titers in the nasal wash was determined by titrating the live virus in the MDCK assays. Results showed the absence of infectious virus in mice previously immunized with Influenza Virus A/WSN/32 (H1N1) PulmoSpheres (WSN-Pul) or control live WSN virus (FIG. 14A). Mice immunized with UV killed WSN virus or naive mice displayed significant titers of influenza virus in the nasal wash. In addition, the mice immunized with WSN-Pul or WSN virus (low dose of live virus) retained their body weight following the challenge (FIG. 14B). Whereas the non-immunized mice and those immunized with UV killed WSN virus displayed significant reduction of body weight followed by death (⅔ in each group by day 7). These results demonstrated that the WSN-Pul can provide effective vaccination efficiency upon mucosal delivery.

XIX

Preparation of Hollow Porous Particles of TA7 Retrovirus by Spray-Drying

Hollow porous TA7 Retrovirus particles were prepared by a spray drying technique with a B-191 Mini Spray-Drier (Büchi, Flawil, Switzerland) under the following conditions: aspiration: 100%, inlet temperature: 85° C.; outlet temperature: 61° C.; feed pump: 10%; $N_2$ flow: 800 L/hr. The feed was prepared by mixing two solutions A and B immediately prior to spray drying.

Preparation A: 2 g of deionized water was used to dissolve 1 mg of TA7 Retrovirus.

Preparation B: A fluorocarbon-in-water emulsion stabilized by phospholipid was prepared in the following way. The phospholipid, 0.3 g EPC-100-3 (Lipoid KG, Ludwigshafen, Germany), was homogenized in 16.5 g of hot deionized water (T=50 to 60° C.) using an Ultra-Turrax mixer (model T-25) at 8000 rpm for 2 to 5 minutes (T=60–70° C.). 8.0 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

One eighth of preparation B by volume was separated and added to preparation A. The resulting TA7 Retrovirus/ perflubron emulsion feed solution was fed into the spray dryer under the conditions described above. The powder collected in the cyclone, and sieving screen was washed into the collection jar using Perflubron. The TA7 Retrovirus suspension in perflubron was subsequently frozen at −60° C. and lyophilized. A free flowing white powder was obtained.

XX

In Vitro Activity of TA7 Retrovirus Spray-Dried Particles

The activity of TA7 Retrovirus following incorporation into the spray-dried particles prepared in Example XIX was examined. Spray-dried TA7 Retrovirus particles were dissolved in saline and applied to Hela cells for 1 hour. 24 h hours post inoculation, the cells were then assayed for transgenic expression using β-gal. No difference was observed between the neat and spray-dried TA7 Retrovirus I particles. These results demonstrate that the TA7 Retrovirus, a relatively large and complex entity, can be effectively incorporated in spray-dried particles with no apparent loss of activity.

XXI

Preparation of Hollow Porous Particles of Bovine Gamma Globulin by Spray-Drying

Hollow porous bovine gamma globulin (BGG) particles were prepared by a spray drying technique with a B-191 Mini Spray-Brier (Büchi, Flawil, Switzerland) under the following conditions: aspiration: 100%, inlet temperature: 85° C.; outlet temperature: 61° C.; feed pump: 10%; $N_2$ flow: 800 L/hr. The feed was prepared by mixing two solutions A and B immediately prior to spray drying.

Preparation A: 21 g of 0.2% saline solution was used to dissolve 0.6 g of BGG (CalBiochem San Diego, Calif.), 0.42 g Lactose (Sigma Chemicals, St. Louis, Mo.) and 25 mg of Pluronic F-68, NF grade (BASF, Parsippany, N.Y.).

Preparation B: A fluorocarbon-in-water emulsion stabilized by phospholipid was prepared in the following way. The phospholipid, 1.02 g EPC-100-3 (Lipoid KG, Ludwigshafen, Germany), was homogenized in 30 g of hot deionized water (T=50 to 60° C.) using an Ultra-Turrax mixer (model T-25) at 8000 rpm for 2 to 5 minutes (T=60–70° C.). 35 g of F-decalin (Air Products, Allentown, Pa.) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

Preparations A and B were combined and fed into the spray-dryer under the conditions described above. A free flowing white powder was collected at the cyclone separator. The hollow porous particles had a volume-weighted mean aerodynamic diameter of 1.27±1.42 μm as determined by a time-of-light analytical method (Aerosizer, Amherst Process Instruments, Amherst, Mass.).

XXII

Andersen Cascade Impactor Results for Bovine Gamma Globulin MDI Formulations

The inhalation properties of a metered dose inhaler (MDI) formulated with hollow porous particles of BGG was prepared according to Example XXI was assessed using an Andersen Cascade impactor. 83 mg of the hollow porous BGG particles was weighed a into 10 ml aluminum can, and dried in a vacuum oven under the flow of nitrogen for 3–4 hours at 40° C. The can was crimp sealed using a DF31/ 50act 50 I valve (Valois of America, Greenwich, Conn.) and filled with 9.64 g HFA-134a (DuPont, Wilmington, Del.) propellant by overpressure through the stem.

Figure 15:
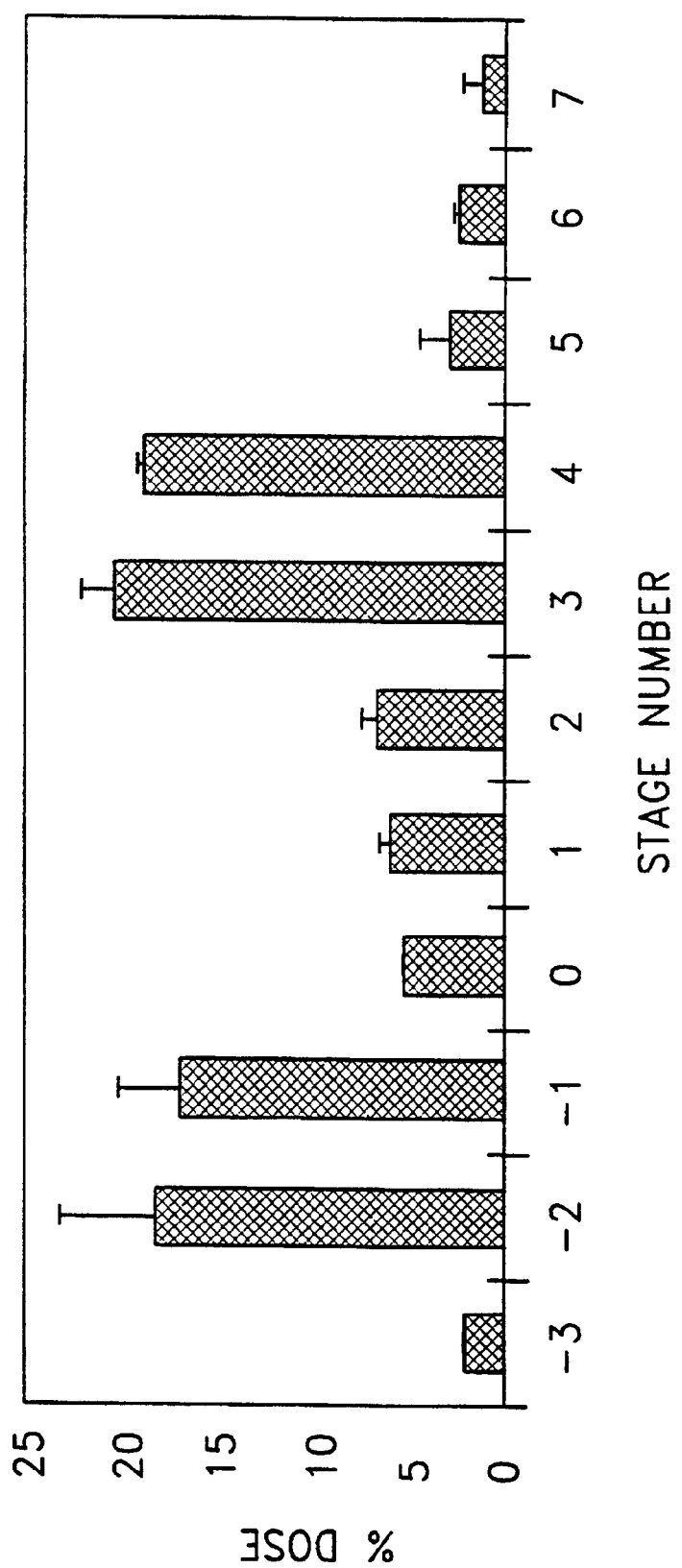
FIG. 15 presents results of an in vitro Andersen cascade impactor study showing efficient delivery of formulated microspheres comprising bovine gamma globulin from a metered dose inhaler.

Upon actuation of the apparatus, a fine particle fraction of 61% and fine particle dose of 68 μg were observed (FIG. 15). The instant example illustrates that a relatively large bioactive agent such as BGG can be formulated and effectively delivered from a MDI.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

What is claimed is:

1. A medicament for the modulation of the immune system of a subject comprising a plurality of microstructures associated with one or more immunoactive agents, wherein said microstructures comprise at least about 5% w/w of a biocompatible surfactant selected from the group consisting of saturated and unsaturated lipids, nonionic detergents, nonionic block copolymers, ionic surfactants, cationic surfactants, biocompatible fluorinated surfactants, and combinations thereof; and wherein the immune response elicited by the composition of the present invention is greater than the immune response provoked by intravenous or intraperitoneal administration of the same antigen solubilized or suspended in an aqueous carrier.

2. The medicament of claim 1, wherein said microstructures further comprise at least one penetration enhancing excipient selected from the group consisting of:
chelating agents, surfactants, fatty acids, bile salts, and combinations thereof.

3. The medicament of claim 2, wherein said at least one penetration enhancing excipient is a short-chain phospholipid with a chain length of 10 carbons or less.

4. The medicament of claim 1, wherein said biocompatible surfactant is selected from the group consisting of phospholipids, poloxamers, and combinations thereof.

5. The medicament of claim 4, wherein said phospholipid is selected from the group consisting of dilauroylphosphatidylcholine, dioleylphosphatidylcholine, dipalmitoylphosphatidylcholine, disteroylphosphatidylcholine, dibehenoylphosphatidylcholine, diarachidoylphosphatidylcholine, and combinations thereof.

6. The medicament of claim 1, wherein said microstructures comprise at least about 25% w/w of said biocompatible surfactant.

7. The medicament of claim 1, wherein said microstructures are dispersed in a nonaqueous suspension medium.

8. The medicament of claim 7, wherein said nonaqueous suspension medium comprises a compound selected from the group consisting of hydrofluoroalkanes, fluorocarbons, perfluorocarbons, fluorocarbon/hydrocarbon diblocks, hydrocarbons, alcohols, ethers, and combinations thereof.

9. The medicament of claim 7, wherein said nonaqueous suspension medium comprises a compound selected from the group consisting of liquid fluorochemicals and hydrofluoroalkane propellants.

10. The medicament of claim 1, wherein the mean aerodynamic diameter of said microstructures is between about 0.5 and about 5 μm.

11. The medicament of claim 1, wherein said microstructures have a mean geometric diameter of between about 1 and about 30 μm.

12. The medicament of claim 1, wherein said microstructures have a mean geometric diameter of less than about 5 μm.

13. The medicament of claim 1, wherein said microstructures are selected from the group consisting of particulates, microparticulates, perforated microstructures, and combinations thereof.

14. The medicament of claim 1, wherein said microstructures are perforated microstructures.

15. The medicament of claim 14, wherein said perforated microstructures comprise hollow porous microstructures.

16. The medicament of claim 1, wherein said immunoactive agent is selected from the group consisting of immunoactive peptides, polypeptides, proteins, carbohydrates, genetic material, and microbes.

17. The medicament of claim 1, wherein said immunoactive agent comprises a vaccine.

18. The medicament of claim 17, wherein said vaccine is selected from the group consisting of inactivated microbes, live attenuated microbes, phages, subunit vaccine proteins, subunit vaccine peptides, subunit vaccine carbohydrates, replicons, viral vectors, plasmids, and combinations thereof.

19. The medicament of claim 1, wherein said modulation of the immune system of a subject comprises an immune response selected from the group consisting of:
eliciting an immune response to a foreign antigen or pathogenic particle; inducing localized or systemic passive immunity; stimulating an immune response; and down regulating an immune reaction.

20. The medicament of claim 1, wherein said modulation of the immune system of a subject comprises mucosal immunity.

21. The medicament of claim 1, wherein said medicament is formulated so as to be capable of being administered to said subject using a delivery methodology selected from the group consisting of topical, intramuscular, transdermal, intradermal, intraperitoneal, nasal, pulmonary, vaginal, rectal, aural, oral or ocular administration.

22. A vaccine for eliciting an enhanced immune response in a subject comprising a plurality of microstructures associated with one or more immunoactive agents, wherein said microstructures comprise at least 5% w/w of a biocompatible surfactant selected from the group consisting of saturated and unsaturated lipids, nonionic detergents, nonionic block copolymers, ionic surfactants, cationic surfactants, biocompatible fluorinated surfactants, and combinations thereof,
wherein said vaccine is formulated so as to be capable of being administered to the respiratory tract of said subject; and
wherein said enhanced immune response is enhanced relative to the immune response elicited by a comparable immunoactive agent delivered via an aqueous carrier in the substantial absence of said microstructures.

23. The vaccine of claim 22, wherein said biocompatible surfactant is selected from the group consisting of phospholipids, poloxamers, and combinations thereof.

24. The vaccine of claim 23, wherein said phospholipid is selected from the group consisting of dilauroylphosphatidylcholine, dioleylphosphatidylcholine, dipalmitoylphosphatidylcholine, disteroylphosphatidylcholine, dibehenoylphosphatidylcholine, diarachidoylphosphatidylcholine, and combinations thereof.

25. The vaccine of claim 22, wherein said immunoactive agent is selected from the group consisting of inactivated microbes, live attenuated microbes, phages, subunit vaccine proteins, subunit vaccine peptides, subunit vaccine carbohydrates, replicons, viral vectors, plasmids, other immunoactive genetic and recombinant materials, and combinations thereof.

26. The vaccine of claim 22, wherein said vaccine is compatible with administration via a dry powder inhaler.

27. The vaccine of claim 22, wherein said microstructures are dispersed in a nonaqueous suspension medium.

28. The vaccine of claim 27, wherein said nonaqueous suspension medium comprises a compound selected from the group consisting of liquid fluorochemicals and hydrofluoroalkane propellants.

29. The vaccine of claim 27, wherein said vaccine is administered using a metered dose inhaler, a nebulizer, an atomizer, a nasal pump, or a spray bottle.

30. The vaccine of claim 22, wherein said microstructures are selected from the group consisting of: particulates, microparticulates, and perforated microstructures.

31. The vaccine of claim 22, wherein said microstructures comprise perforated microstructures.

32. The vaccine of claim 31, wherein said perforated microstructures comprise hollow porous microstructures.

33. The vaccine of claim 22, wherein the mean aerodynamic diameter of said microstructures is between about 0.5 and about 5 μm.

34. The vaccine of claim 22, wherein said microstructures have a mean geometric diameter of between about 1 and about 30 μm.

35. The vaccine of claim 22, wherein said microstructures have a mean geometric diameter of less than about 5 μm.

36. The vaccine of claim 22, wherein said elicited immune response comprises mucosal and/or systemic immunity.

37. The vaccine of claim 22, wherein said microstructures further comprise an immunogenicity modifying excipient.

38. The vaccine of claim 37, wherein said immunogenicity modifying excipient is selected from the group consisting of mannans, cell-binding polysaccharides, cofactors, cytokines, and combinations thereof.

39. The vaccine of claim 22, wherein said immune response is enhanced by at least about 25% relative to the immune response elicited by a comparable immunoactive agent delivered via an aqueous carrier in the substantial absence of said microstructures.

40. A method for providing enhanced active immunization comprising administering to a patient a therapeutically or prophylactically effective amount of a medicament that comprises a plurality of microstructures associated with one or more vaccines, wherein said microstructures comprise at least about 5% w/w of a biocompatible surfactant selected from the group consisting of saturated and unsaturated lipids, nonionic detergents, nonionic block copolymers, ionic surfactants, cationic surfactants, biocompatible fluorinated surfactants, and combinations thereof; and wherein said enhanced active immunization is enhanced relative to the immune response elicited by comparable vaccines delivered via an aqueous carrier in the substantial absence of said microstructures.

41. The method of claim 40, wherein said biocompatible surfactant is selected from the group consisting of phospholipids, poloxamers, and combinations thereof.

42. The method of claim 40, wherein said vaccine is selected from the group consisting of inactivated microbes, live attenuated microbes, phages, subunit vaccine proteins, subunit vaccine peptides, subunit vaccine carbohydrates, replicons, viral vectors, plasmids, other immunoactive genetic and recombinant materials, and combinations thereof.

43. The method of claim 40, wherein said medicament is formulated so as to be capable of being delivered to or via the respiratory tract.

44. The method of claim 40, wherein said microstructures further comprise an immunogenicity modifying excipient.

45. The method of claim 44, wherein said immunogenicity modifying excipient is selected from the group consisting of mannans, cell-binding polysaccharides, cofactors, cytokines, and combinations thereof.

46. A method for providing enhanced passive immunization comprising administering to a patient a therapeutically or prophylactically effective amount of a medicament that comprises a plurality of microstructures associated with one or more immunoglobulins or immunoglobulin-like molecules, wherein said microstructures comprise at least about 5% w/w of a biocompatible surfactant selected from the group consisting of saturated and unsaturated lipids, nonionic detergents, nonionic block copolymers, ionic surfactants, cationic surfactants, biocompatible fluorinated surfactants, and combinations thereof; and wherein said enhanced passive immunization is enhanced relative to the immune response elicited by comparable immunoglobulins or immunoglobulin-like molecules delivered via an aqueous carrier in the substantial absence of said microstructures.

47. The method of claim 46, wherein said biocompatible surfactant is selected from the group consisting of phospholipids, poloxamers, and combinations thereof.

48. The method of claim 46, wherein said medicament is formulated so as to be delivered to or via the respiratory tract.

49. A method for treating an autoimmune disease or disorder comprising administering to a patient a therapeutically or prophylactically effective amount of a medicament that comprises a plurality of microstructures associated with one or more immunomodulators, wherein said microstructures comprise at least about 5% w/w of a biocompatible surfactant selected from the group consisting of saturated and unsaturated lipids, nonionic detergents, nonionic block copolymers, ionic surfactants, cationic surfactants, biocompatible fluorinated surfactants, and combinations thereof; and wherein said treatment for an autoimmune disease or disorder is enhanced relative to the treatment elicited by comparable immunomodulators delivered via an aqueous carrier in the substantial absence of said microstructures.

50. The method of claim 49, wherein said immunomodulators are selected from the group consisting of: foreign antigens, self-antigens, antigen epitope peptides, immunoglobulins, autoimmune related-ligands, cytokines, and combinations thereof.

51. The method of claim 49, wherein said biocompatible surfactant is selected from the group consisting of phospholipids, poloxamers, and combinations thereof.

52. The method of claim 49, wherein said medicament is formulated so as to be capable of being delivered to or via the respiratory tract.

* * * * *

UNITED STATES PATENT AND TRADEMARK OFFICE
CERTIFICATE OF CORRECTION

PATENT NO. : 6,630,169 B1
APPLICATION NO. : 09/720536
DATED : October 7, 2003
INVENTOR(S) : Bot et al.

It is certified that error appears in the above-identified patent and that said Letters Patent is hereby corrected as shown below:

Claim 5: column 65, line 3 and 5 change the spelling of "dioleyphosphatidylcholine, disteroylphosphatidylcholine" to read as --dioleoylphosphatidylcholine, distearoylphosphatidylcholine--

Claim 24: column 66, line 21, 23 change the spelling of "dioleylphosphatidylcholine, disteroylphosphatidylcholine" to read as --dioleoylphosphatidylcholine, distearoylphosphatidylcholine--

Specification, Column 22, Line 6: change the spelling of "disteroylphosphatidylcholine" to read as --distearoylphosphatidylcholine--

Specification, Column 22, Line 6: after the comma, add the omitted phospholipid --dioleoylphosphatidylcholine-- to the listing of exemplary phospholipids.

Signed and Sealed this

Sixth Day of February, 2007

JON W. DUDAS
*Director of the United States Patent and Trademark Office*